(12) United States Patent
Wang et al.

(10) Patent No.: US 9,815,833 B2
(45) Date of Patent: Nov. 14, 2017

(54) PYRIDINE DERIVATIVE AND MEDICAL USE THEREOF

(71) Applicant: Chengdu Easton Biopharmaceuticals Co., Ltd., Chengdu (CN)

(72) Inventors: Ying Wang, Chengdu (CN); Yongzhe Xiang, Chengdu (CN); Guodong Cen, Chengdu (CN); Jibing Zhang, Chengdu (CN); Long Huang, Chengdu (CN); Ning Zhou, Chengdu (CN); Jian Liu, Chengdu (CN); Hui Qiao, Chengdu (CN)

(73) Assignee: Chengdu Easton Biopharmaceuticals Co., Ltd., Chengdu (CN)

( * ) Notice: Subject to any disclaimer, the term of this patent is extended or adjusted under 35 U.S.C. 154(b) by 0 days.

(21) Appl. No.: 14/908,902

(22) PCT Filed: Nov. 17, 2014

(86) PCT No.: PCT/CN2014/091235
§ 371 (c)(1),
(2) Date: Jan. 29, 2016

(87) PCT Pub. No.: WO2015/070809
PCT Pub. Date: May 21, 2015

(65) Prior Publication Data
US 2016/0244440 A1    Aug. 25, 2016

(30) Foreign Application Priority Data
Nov. 18, 2013  (CN) .......................... 2013 1 0576837

(51) Int. Cl.
| | |
|---|---|
| C07D 471/02 | (2006.01) |
| A61K 31/44 | (2006.01) |
| C07D 471/04 | (2006.01) |
| A61K 31/437 | (2006.01) |

(52) U.S. Cl.
CPC .......... *C07D 471/04* (2013.01); *A61K 31/437* (2013.01)

(58) Field of Classification Search
CPC .......................... C07D 471/04; A61K 31/437
USPC .................................. 514/303; 546/120, 119
See application file for complete search history.

(56) References Cited

U.S. PATENT DOCUMENTS

2003/0191115 A1* 10/2003 Pinto .................... C07D 211/40
514/224.2

FOREIGN PATENT DOCUMENTS

| CN | 103342704 A | 10/2013 |
| WO | WO 03/026652 A1 | 4/2003 |
| WO | WO03/048081 A2 | 6/2003 |
| WO | WO2013/119328 A1 | 8/2013 |

OTHER PUBLICATIONS

Extended European Search Report, Application No. 14862759.9 (dated Aug. 5, 2016) 7 pages.

* cited by examiner

*Primary Examiner* — Shengjun Wang
(74) *Attorney, Agent, or Firm* — Nixon Peabody LLP

(57) ABSTRACT

The present invention relates to the field of pharmaceutical chemistry, specifically to a class of compounds containing lactam and derivative thereof, and especially to a pyridine derivative as shown in general formula (I), preparation method and the use thereof as a Factor Xa inhibitor. The present invention further relates to the medical use of the compound and derivative thereof in preparation of anticoagulant drugs, particularly to the use in preparation of drugs for preventing or treating thrombosis or embolism.

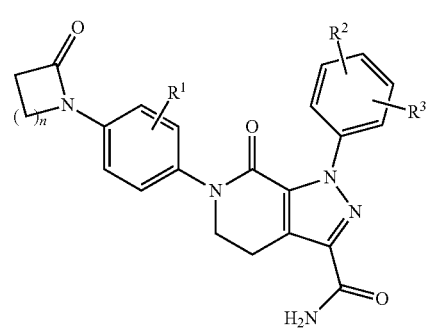

9 Claims, No Drawings

PYRIDINE DERIVATIVE AND MEDICAL USE THEREOF

CROSS-REFERENCE TO RELATED APPLICATIONS

This application is an U.S. national stage of PCT/CN2014/091235, filed on Nov. 17, 2014, which claims priority to Chinese Patent Application No. 201310576837.6, filed on Nov. 18, 2013, the contents of which are each incorporated herein by reference in its entirety.

FIELD OF THE INVENTION

The present invention relates to the field of pharmaceutical chemistry, specifically to a class of compounds containing lactam and derivatives thereof as Factor Xa (hereinafter also abbreviated as FXa) inhibitors, and further to the medical use of the above compounds and derivatives thereof in preparing anticoagulant. The present invention in particular relates to pyridine derivatives, preparation method and the use thereof in preparing a medicament for preventing or treating thrombosis or embolism.

BACKGROUND OF THE INVENTION

Thrombotic disease is a disease seriously harmful to human health. According to the site, conditions and nature of thrombosis, thrombotic disease is mainly categorized into venous thrombosis and arterial thrombosis. Arterial thrombosis starts from the arterial wall atherosclerotic lesions and platelet activation, and causes severe clinical reactions which are mainly acute myocardial infarction, stroke; venous thrombosis is induced by a variety of causes in veins, which can lead to venous thromboembolism (VTE), wherein the main clinical manifestations thereof is deep venous thrombosis (DVT) and pulmonary embolism (PE). VTE is the third largest cardiovascular disease after acute coronary syndrome and stroke. VTE accounts for 10% of all death cases in the hospital, and the number of symptomatic VTE occurring in six countries in European Union is 1 million per year, while the death cases thereof exceed the sum of those caused by AIDS, breast cancer, prostate cancer and traffic accidents. The death cases in USA are more than 296,000 per year, while less than 50% of fatal PE were confirmed before death. The prevention of VTE has been listed as one of the most important strategies to reduce the mortality in hospitalized patients in relevant international guidelines.

Evidence of large-scale clinical trial shows that the spread and recurrence of thrombosis can be prevented by anticoagulation therapy, and incidence and mortality of stroke, PE, etc. can be further reduced. Therefore, anticoagulation therapy has become the core and foundation in clinical prevention and treatment of thromboembolic diseases, and the development of anticoagulants is always a hot research and development of new medicaments, especially in the development of medicaments targeting Factor Xa.

SUMMARY OF THE INVENTION

The present invention relates to a class of compounds containing lactam and derivatives thereof as Factor Xa inhibitors, in particular to pyridine derivatives, preparation method and the medical use thereof, especially the pyridine derivatives as represented by the general formula (I) and the use thereof in preparing anticoagulant. More specifically, said use is in preparing a medicament for preventing and treating thrombosis or embolism.

One object of the present invention is to provide a pyridine derivative having the structure as shown in the following general formula (I):

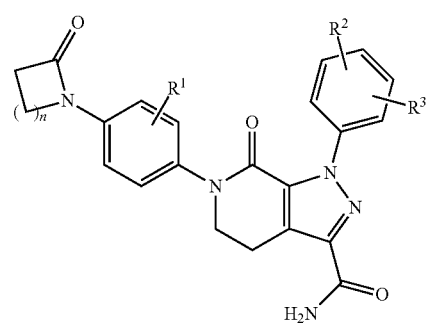

Wherein: $R^1$ is selected from hydrogen atom, $C_1$-$C_{10}$ alkyl or $C_1$-$C_{10}$ alkoxy, wherein any hydrogen atom on $C_1$-$C_{10}$ alkyl or alkoxy can be further replaced by hydroxy or amino;

$R^2$ is selected from hydrogen atom, $C_1$-$C_{10}$ alkyl, $C_1$-$C_{10}$ alkoxy, $C_1$-$C_{10}$ alkylthio, fluorine atom, chlorine atom, bromine atom, iodine atom or trifluoromethyl;

$R^3$ is selected from hydrogen atom, $C_1$-$C_{10}$ alkyl, $C_1$-$C_{10}$ alkoxy, $C_1$-$C_{10}$ alkylthio, fluorine atom, chlorine atom, bromine atom, iodine atom or trifluoromethyl;

n=1, 2 or 3.

Preferably, in the compounds of the present invention as shown in general formula (I):

$R^1$ is selected from hydrogen atom, $C_1$-$C_5$ alkyl or $C_1$-$C_5$ alkoxy;

$R^2$ is selected from hydrogen atom, $C_1$-$C_5$ alkyl, $C_1$-$C_5$ alkoxy, $C_1$-$C_5$ alkylthio, fluorine atom, chlorine atom or trifluoromethyl;

$R^3$ is selected from hydrogen atom, $C_1$-$C_5$ alkyl, $C_1$-$C_5$ alkoxy, $C_1$-$C_5$ alkylthio, fluorine atom, chlorine atom or trifluoromethyl;

n=1, 2 or 3.

Further preferably, in the compounds of the present invention as shown in general formula (I):

$R^1$ is selected from hydrogen atom, $C_1$-$C_3$ alkyl or $C_1$-$C_3$ alkoxy;

$R^2$ is selected from hydrogen atom, $C_1$-$C_3$ alkyl, $C_1$-$C_3$ alkoxy, $C_1$-$C_3$ alkylthio, fluorine atom or trifluoromethyl;

$R^3$ is selected from hydrogen atom, $C_1$-$C_3$ alkyl, $C_1$-$C_3$ alkoxy, $C_1$-$C_3$ alkylthio, fluorine atom or trifluoromethyl;

n=1, 2 or 3.

More preferably, in the compounds of the present invention as shown in general formula (I):

$R^1$ is selected from hydrogen atom, methyl or methoxyl;

$R^2$ is selected from methyl, methoxy, methylthio or fluorine atom;

$R^3$ is selected from hydrogen atom, methyl, methoxy, methylthio or fluorine atom;

n=1, 2 or 3.

Further preferably, in the compounds of the present invention as shown in general formula (I):

$R^1$ is selected from hydrogen atom, methyl or methoxyl;

$R^2$ is selected from methyl, methoxy, methylthio or fluorine atom;

$R^3$ is selected from hydrogen atom, methyl, methoxy, methylthio or fluorine atom;

n=2 or 3.

More preferably, in the compounds of the present invention as shown in general formula (I):
R¹ is selected from hydrogen atom or methyl;
R² is selected from methyl, methoxy or fluorine atom;
R³ is selected from hydrogen atom, methyl, methoxy or fluorine atom;
n=2.

Further preferably, in the compounds of the present invention as shown in general formula (I):
R¹ is selected from methyl;
R² is selected from methyl, methoxy or fluorine atom;
R³ is selected from hydrogen atom, methyl, methoxy or fluorine atom;
n=2.

Alternatively, preferably, in the compounds of the present invention as shown in general formula (I):
R¹ is selected from hydrogen atom, methyl or methoxy;
R² is selected from methyl, methoxy, methylthio or fluorine atom;
R³ is selected from hydrogen atom, methyl, methoxy, methylthio or fluorine atom;
n=3.

Further preferably, in the compounds of the present invention as shown in general formula (I):
R¹ is selected from methyl or methoxy;
R² is selected from methyl, methoxy, methylthio or fluorine atom;
R³ is selected from hydrogen atom, methyl, methoxy, methylthio or fluorine atom;
n=3.

Furthermore, in the compounds of the present invention as shown in general formula (I):
when R¹ is hydrogen atom, R² is hydrogen atom and R³ is methoxy, n=1 or 2.

In the pyridine derivatives of the present invention as shown in general formula (I), the preferred compounds include but not limit to the following compounds:

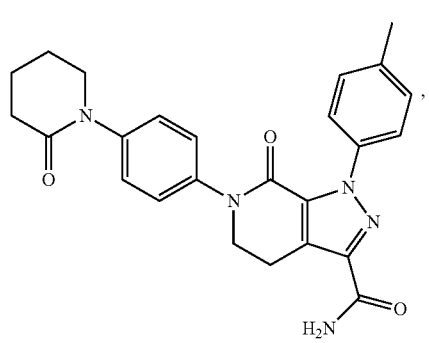

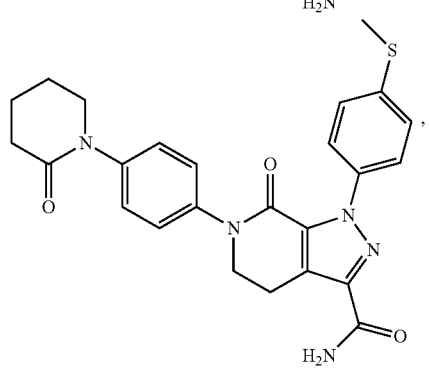

-continued

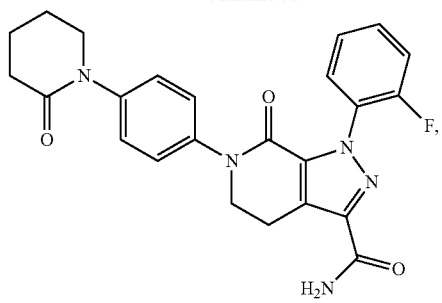

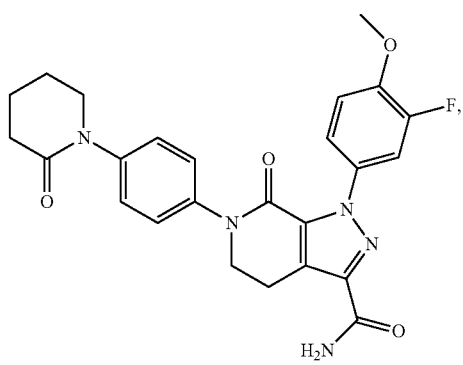

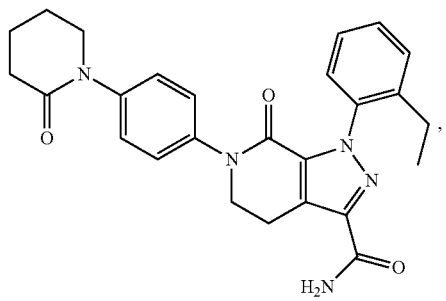

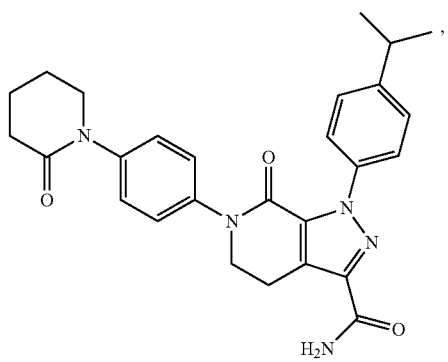

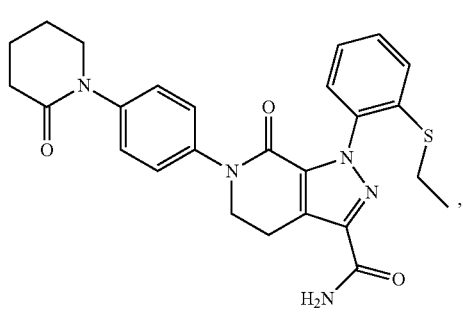

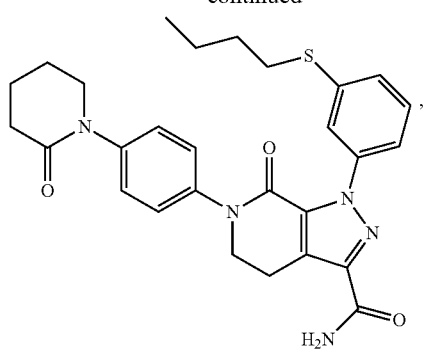
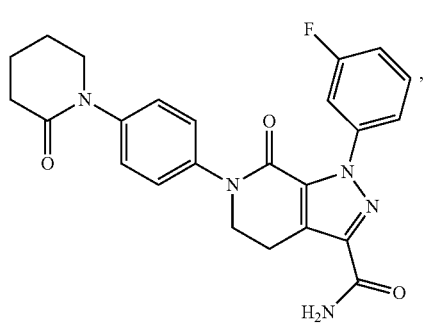
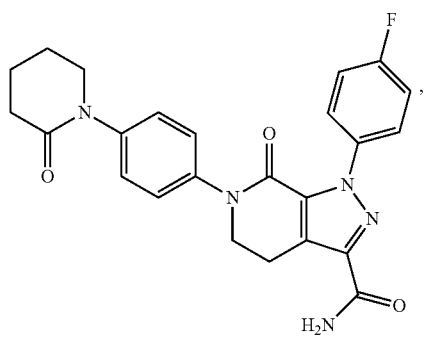
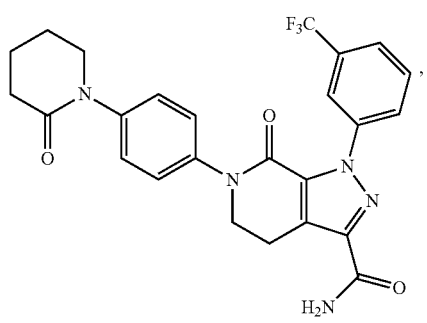
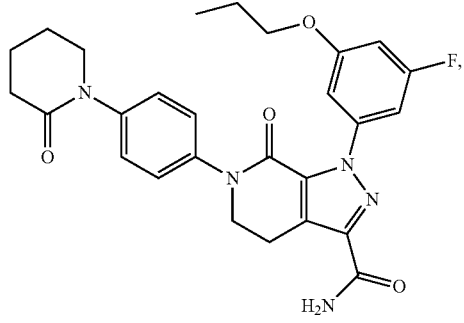
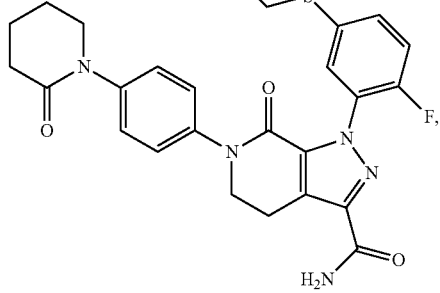
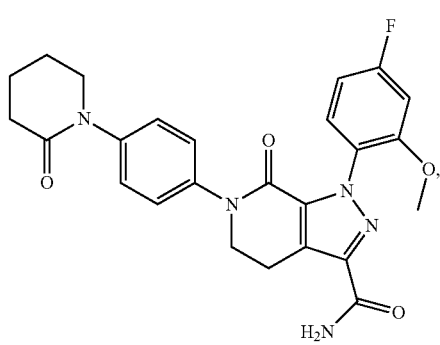
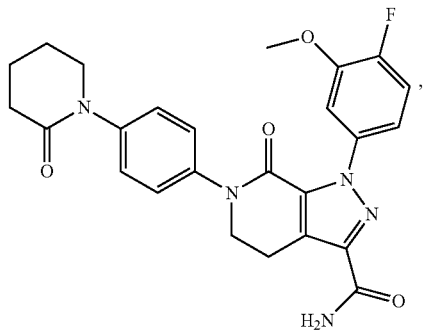
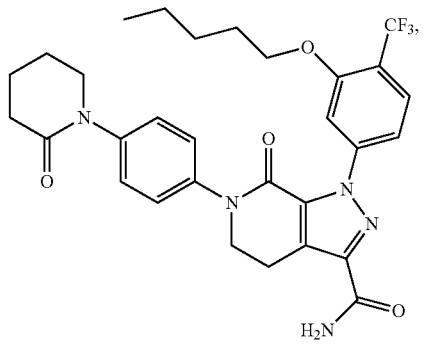
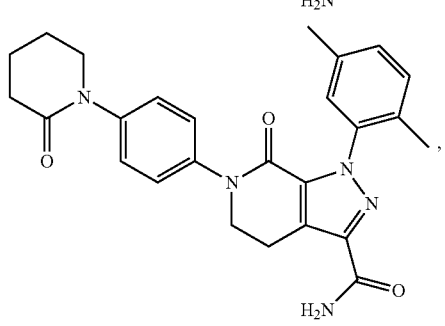

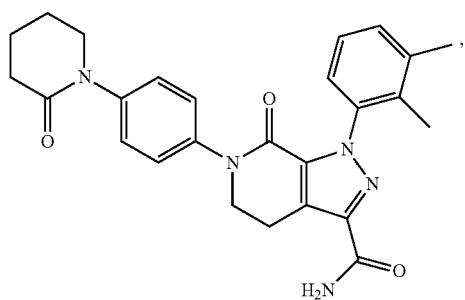
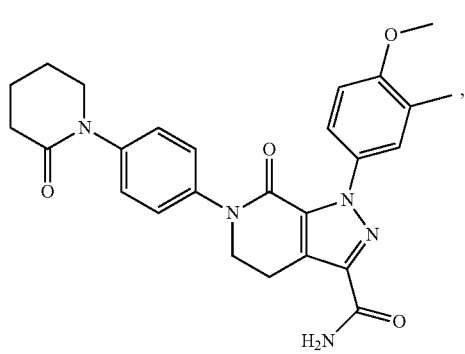
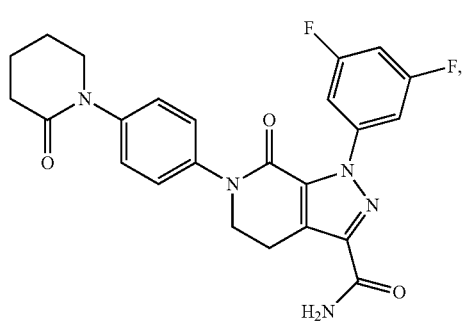
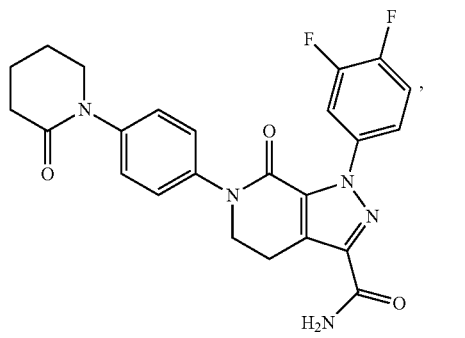
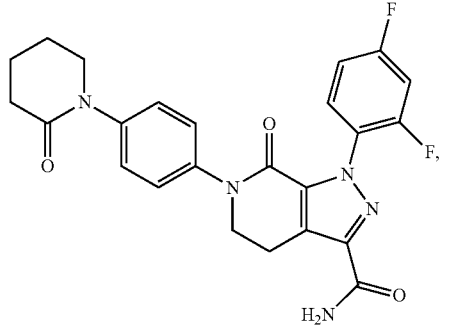
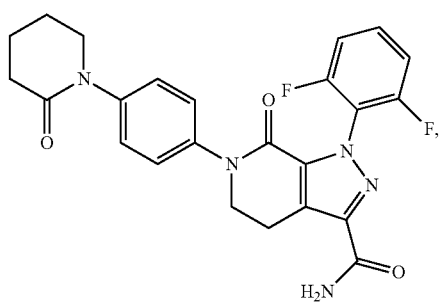
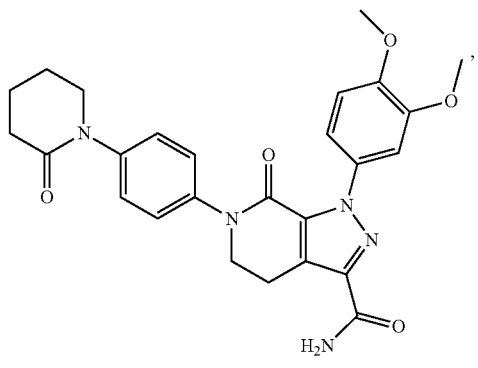
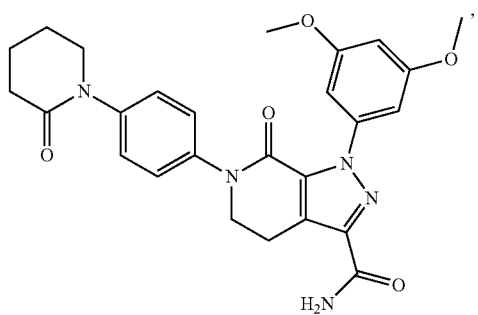
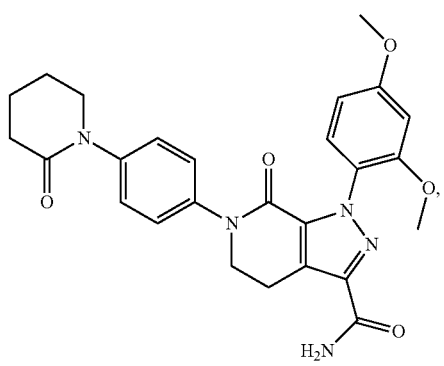
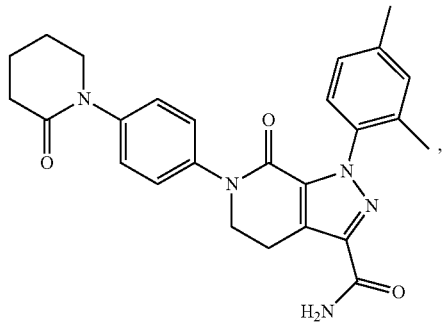

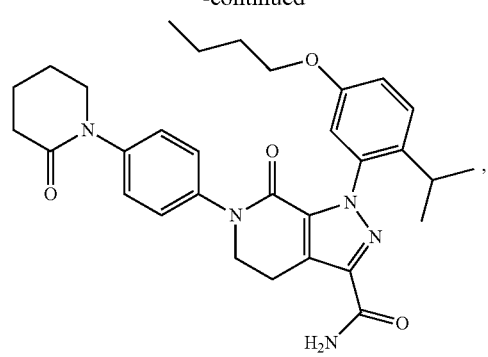
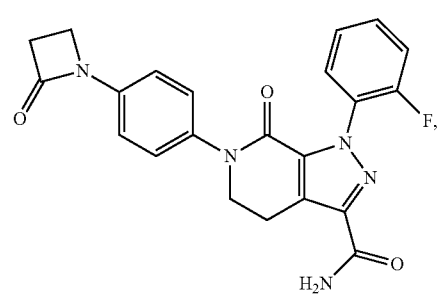
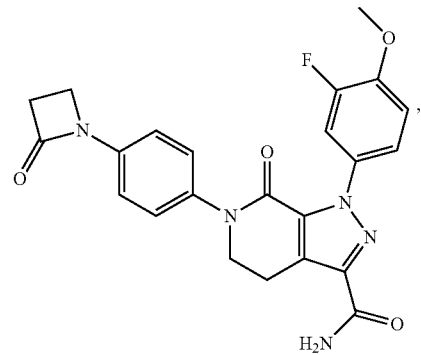
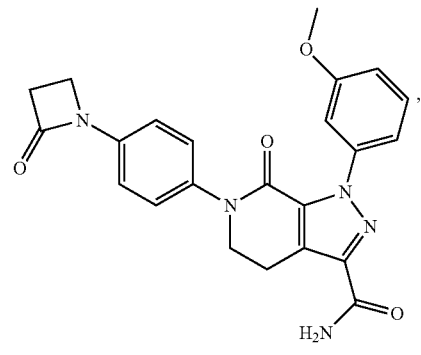
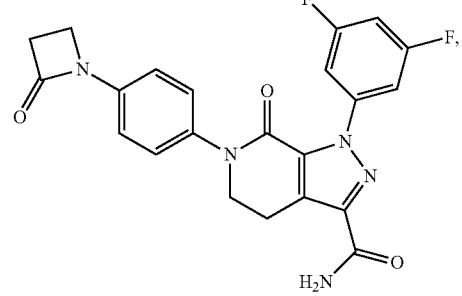
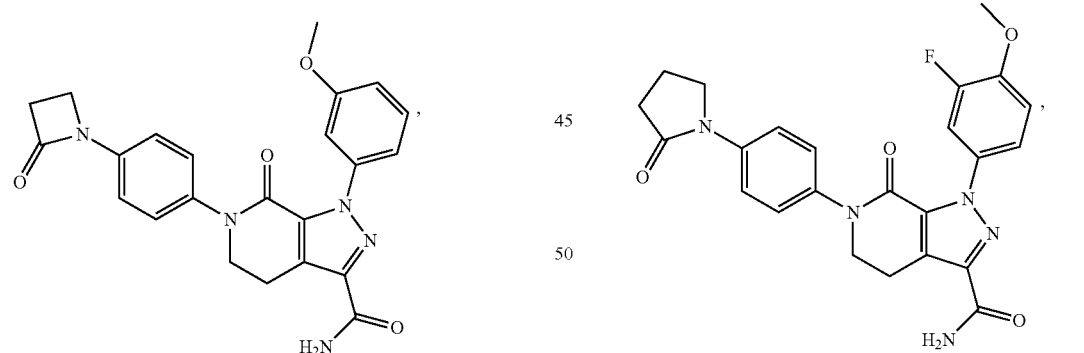
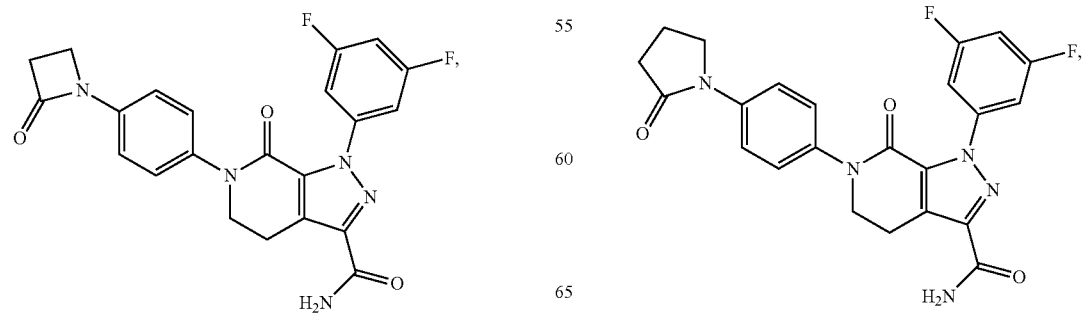
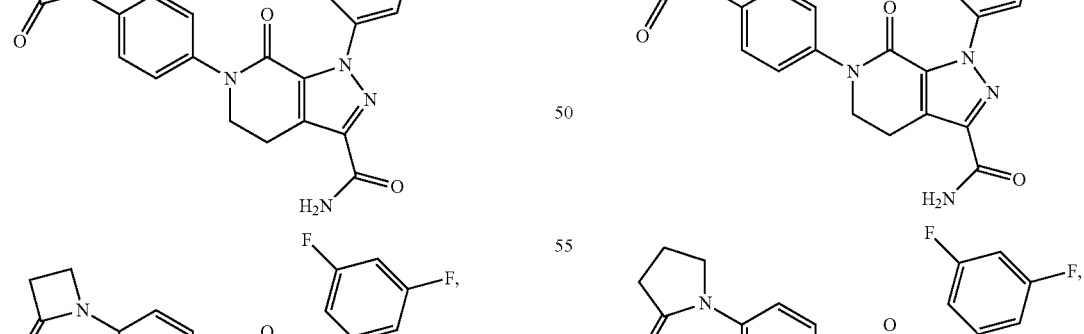

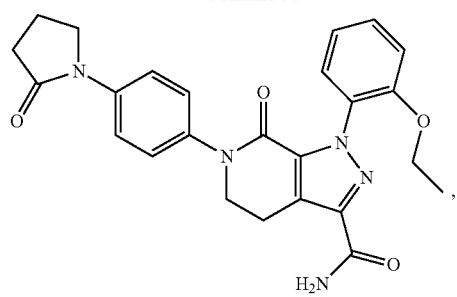
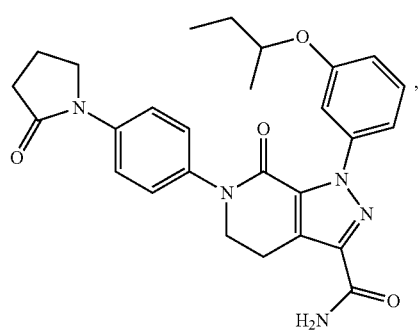
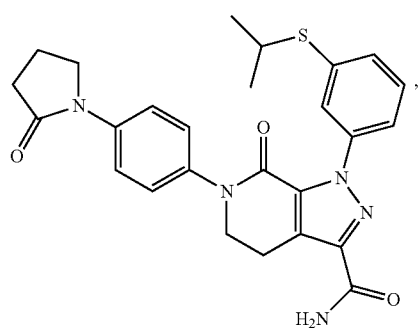
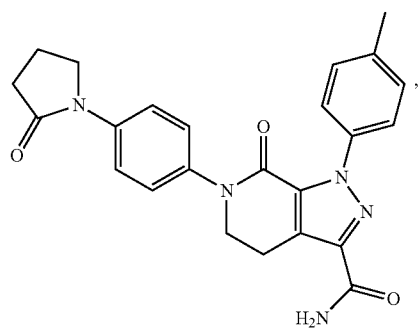
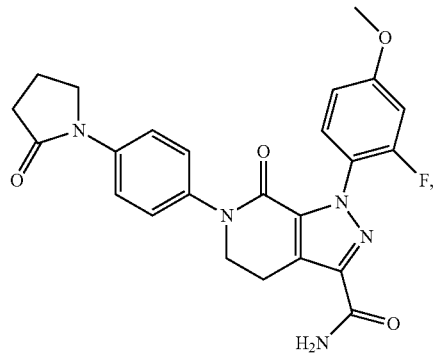
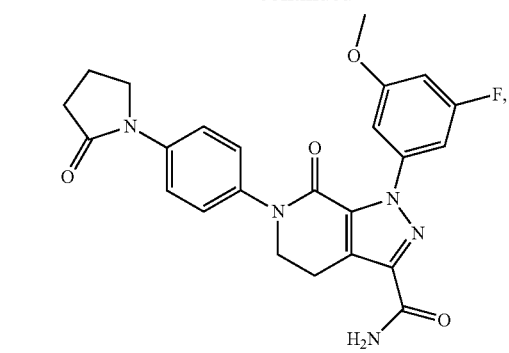
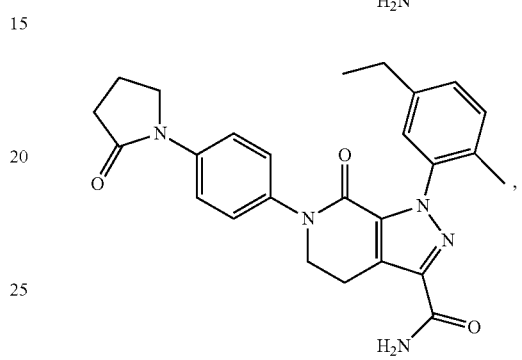
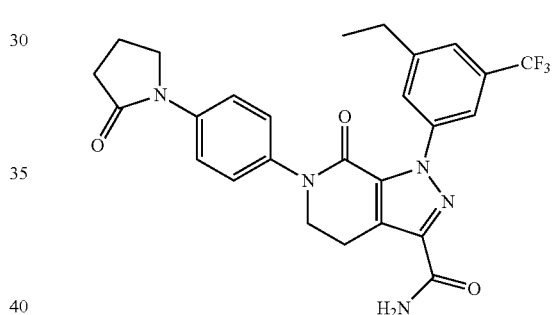
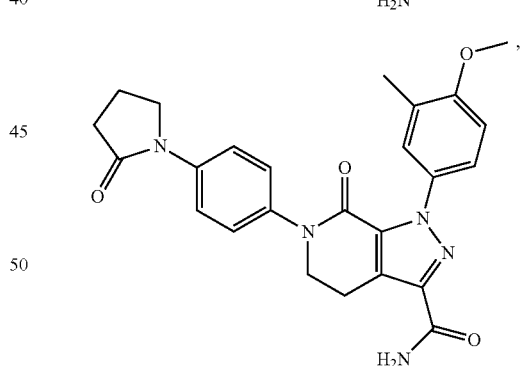
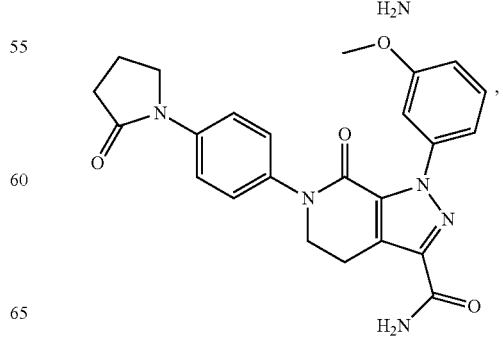

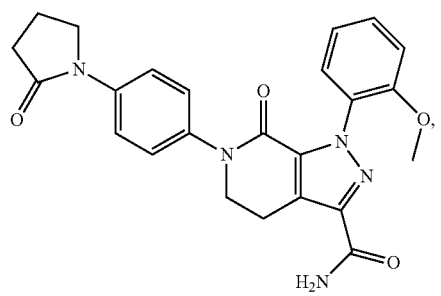
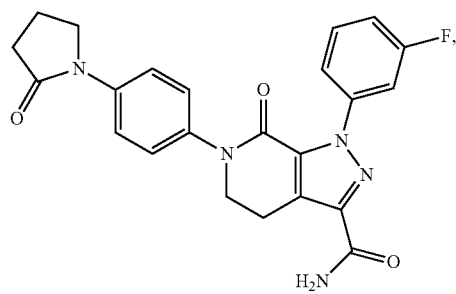
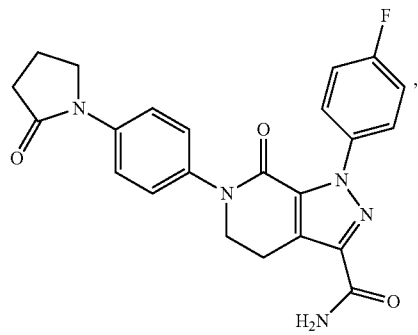
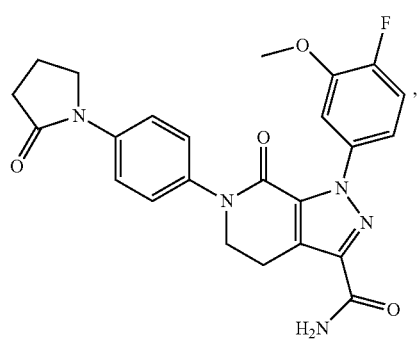
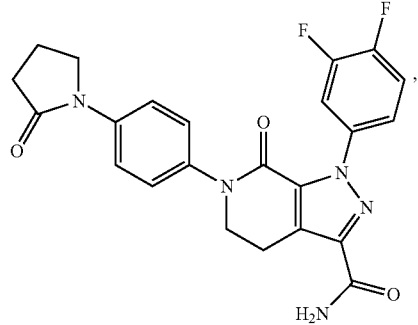
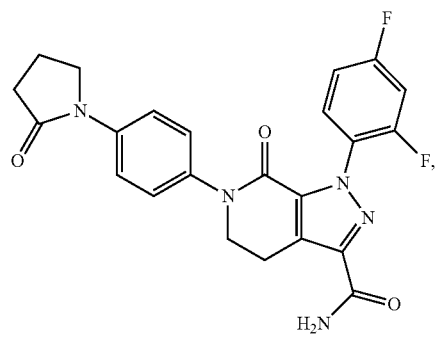
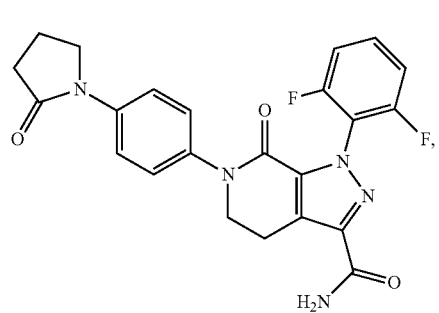
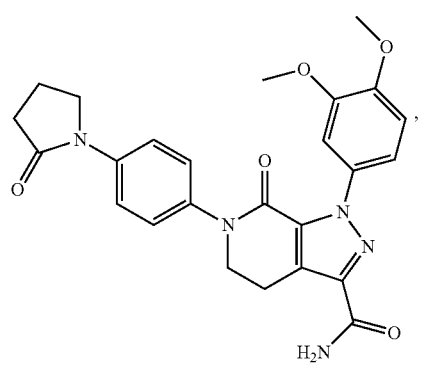
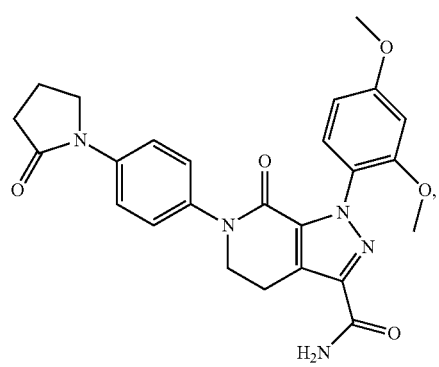
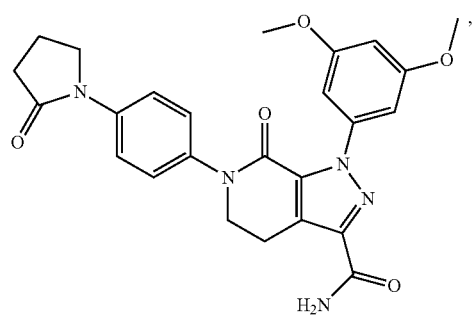

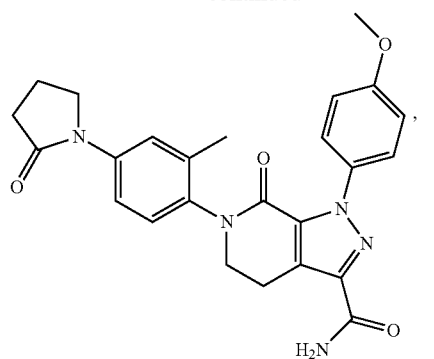
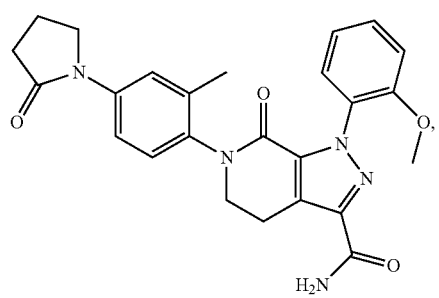
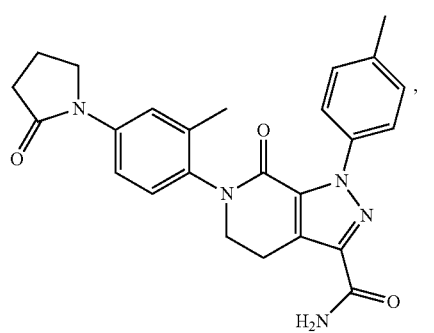
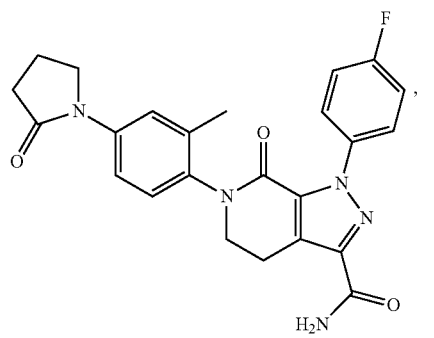
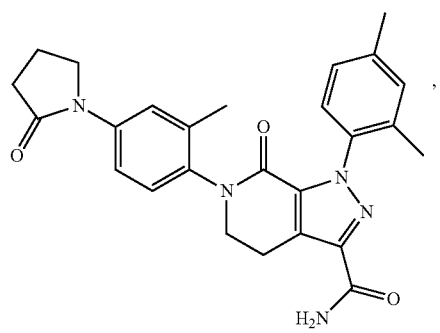
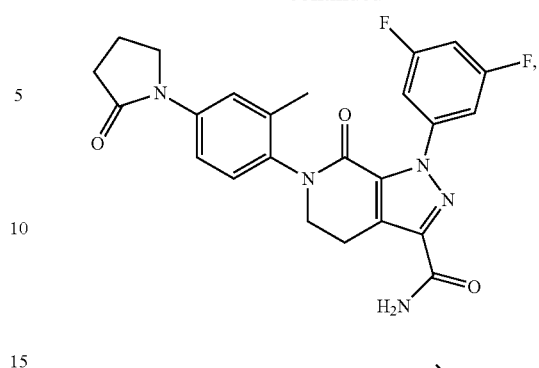
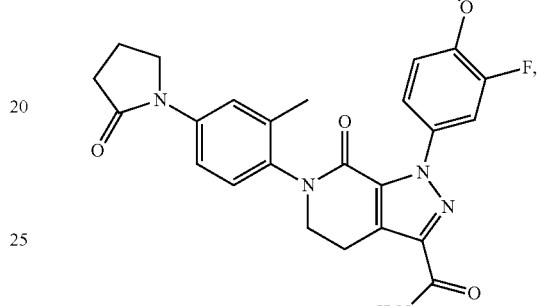
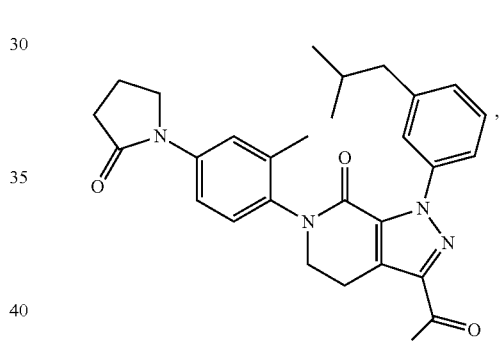
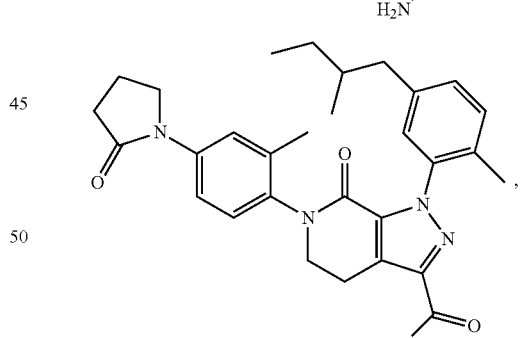
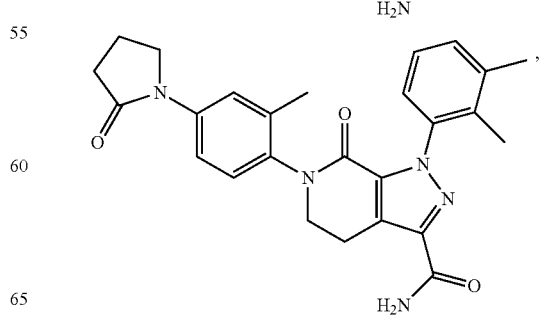

-continued
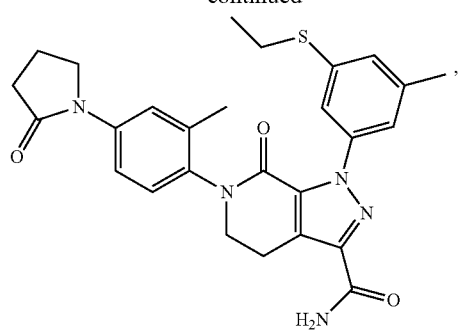
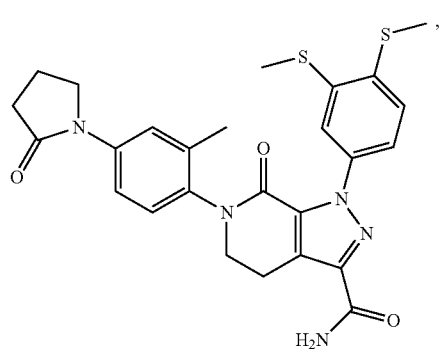
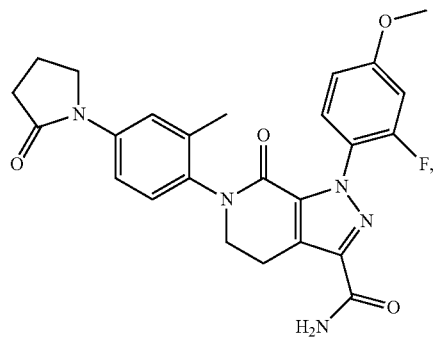
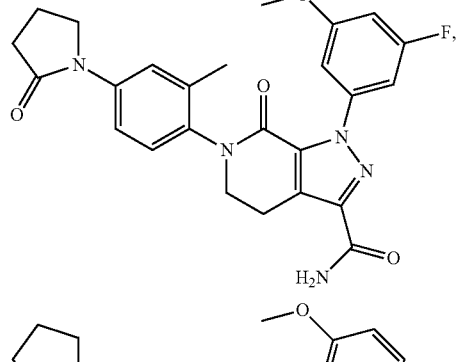
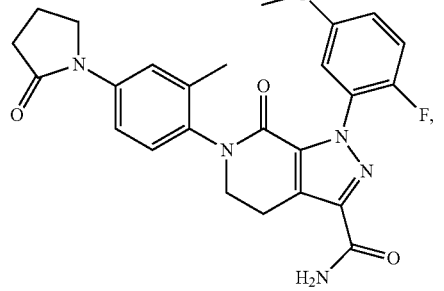
-continued
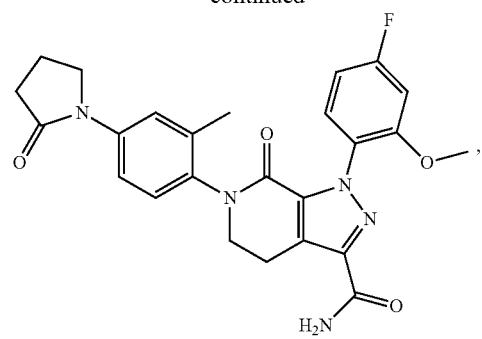
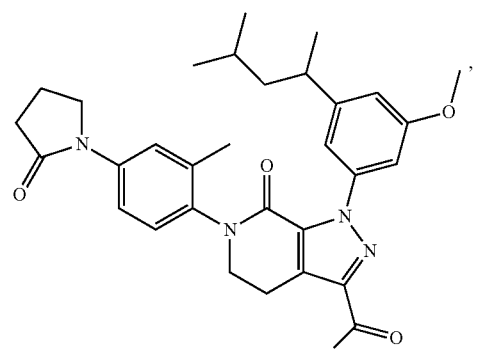
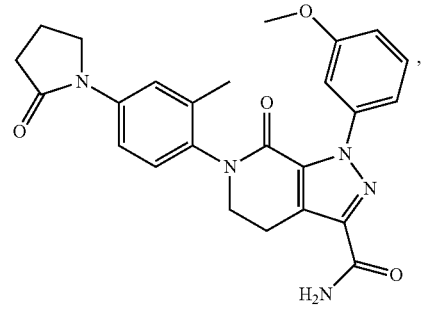
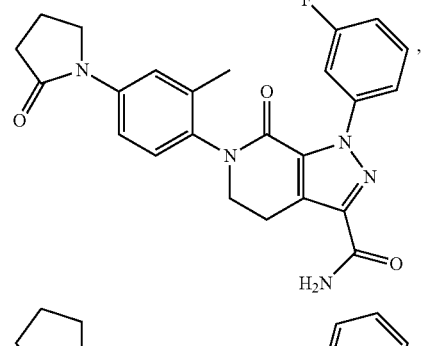
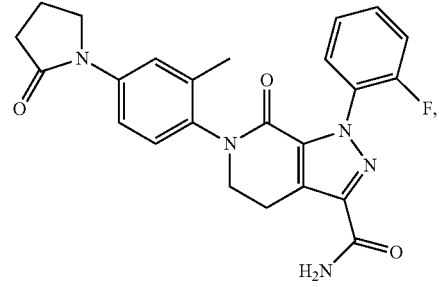

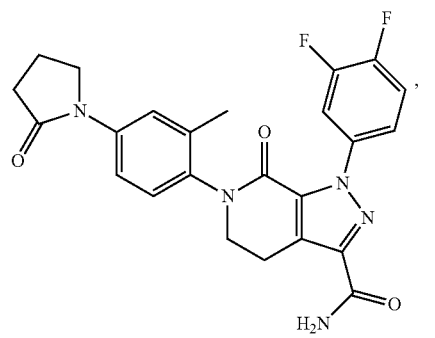
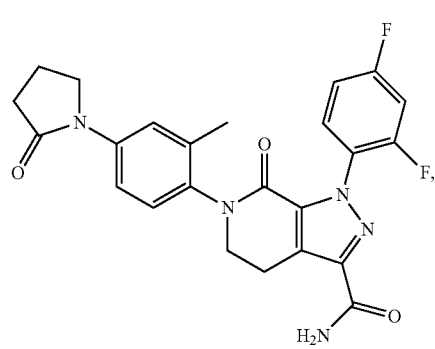
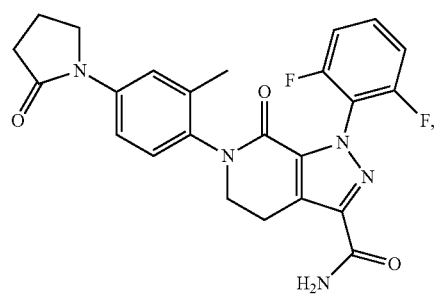
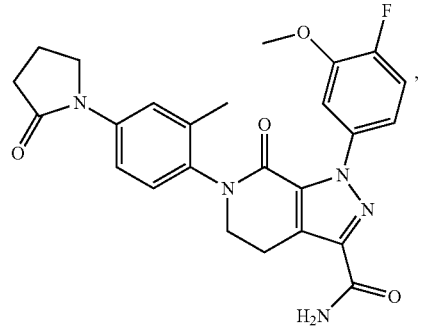
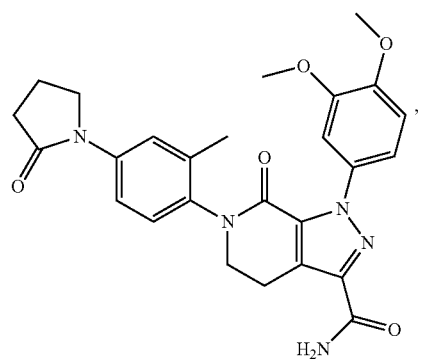
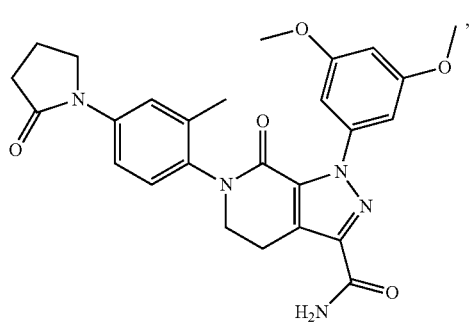
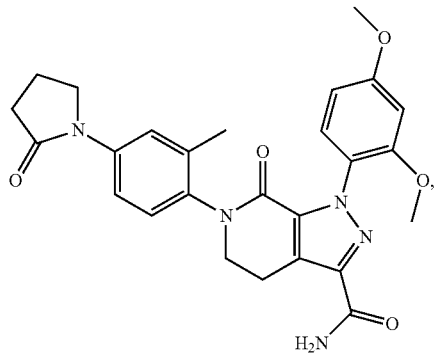
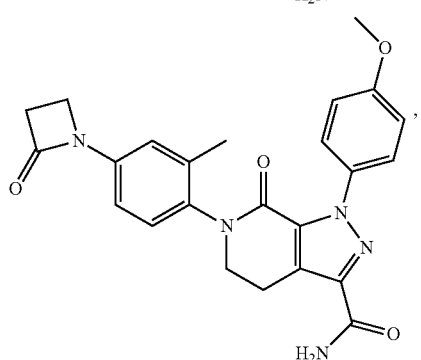
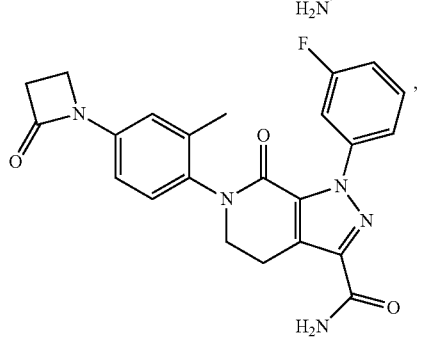
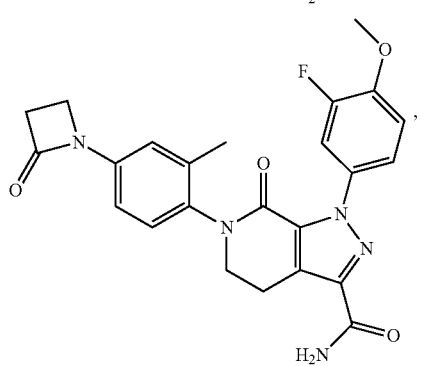

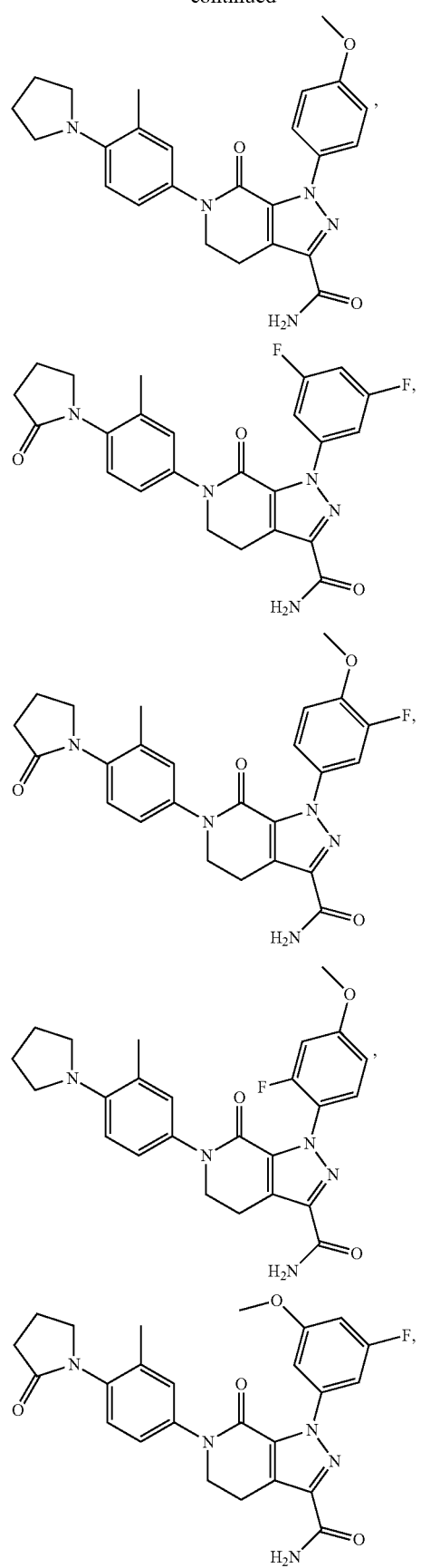
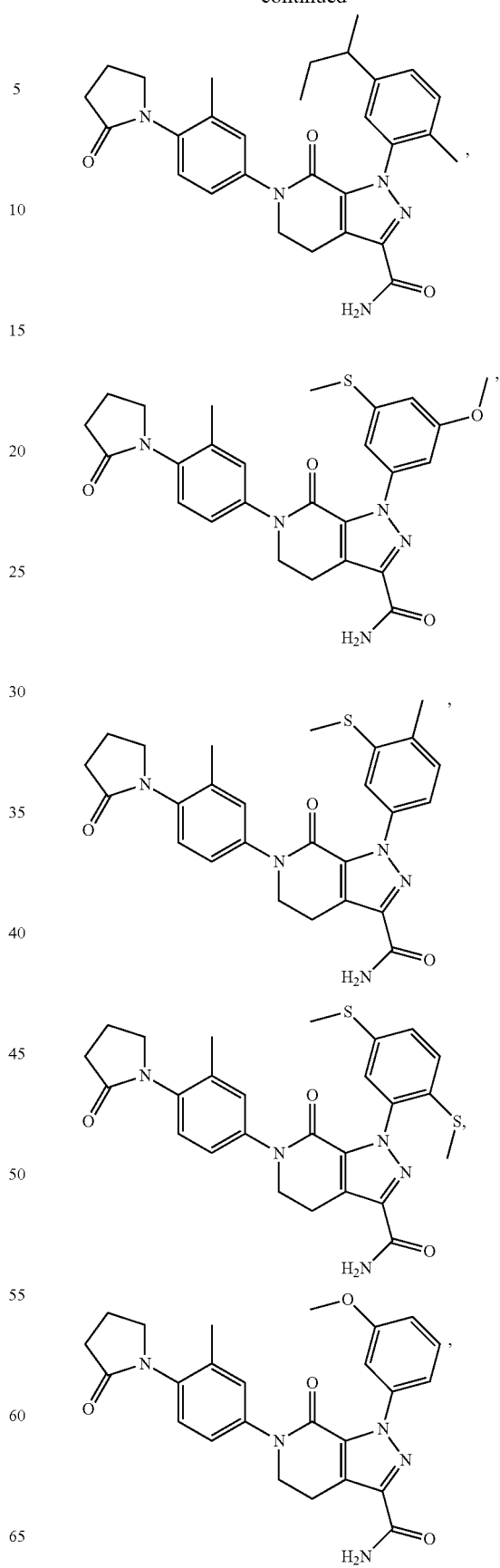

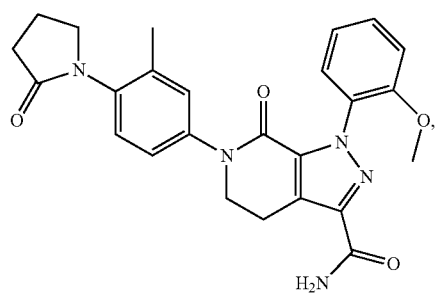
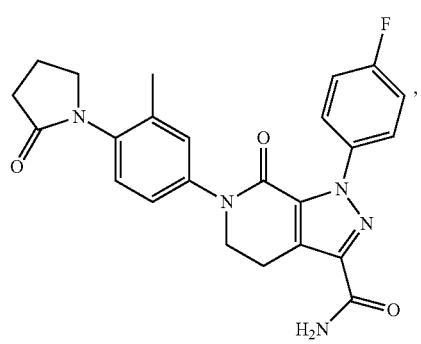
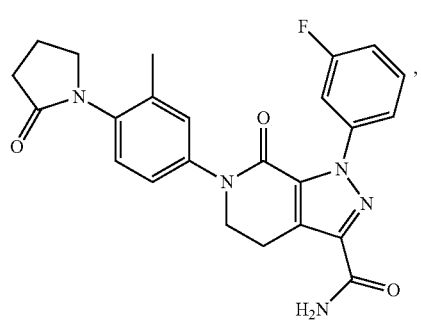
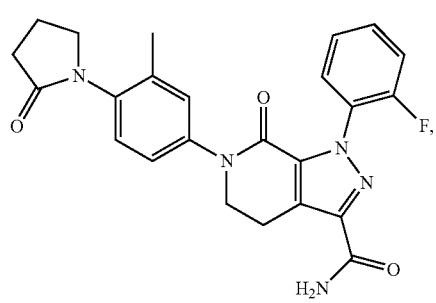
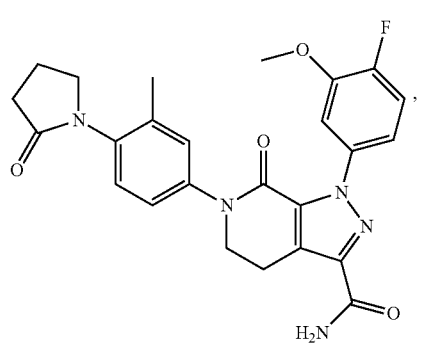
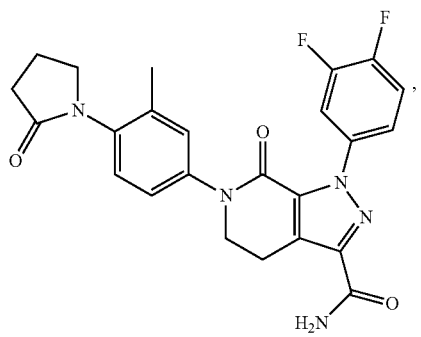
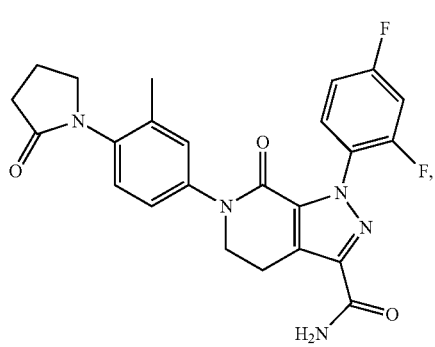
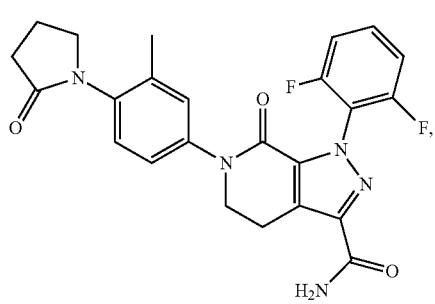
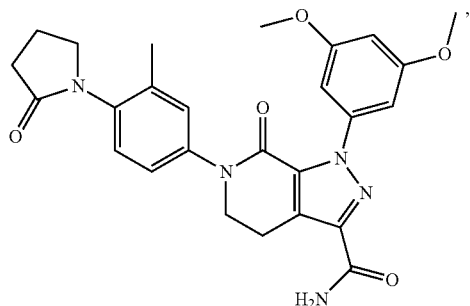
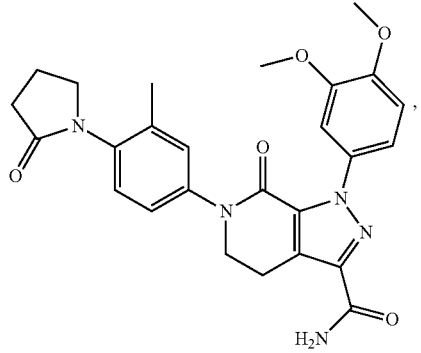

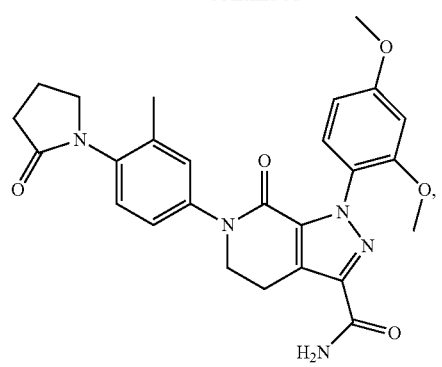
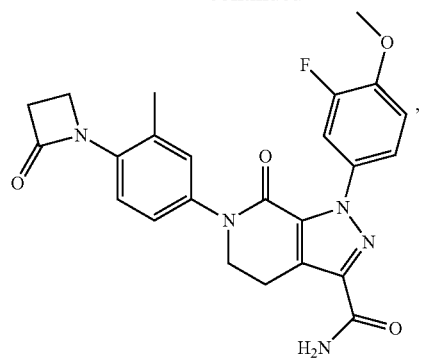
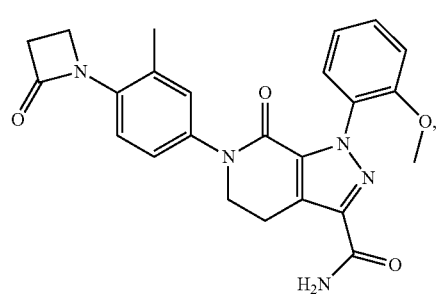
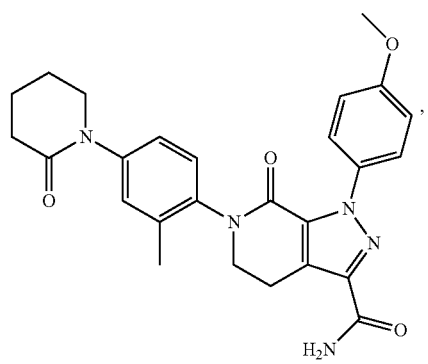
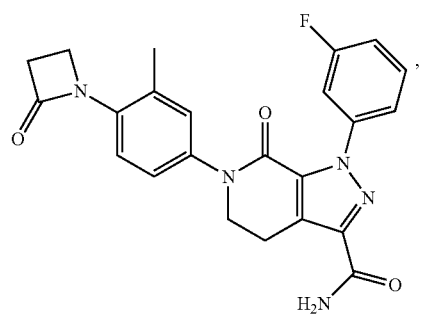
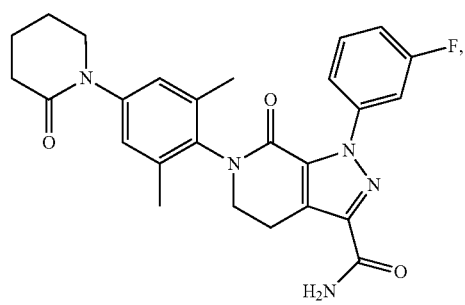
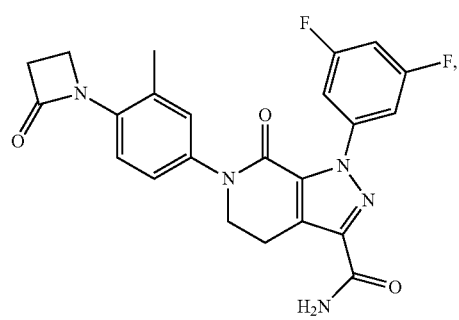
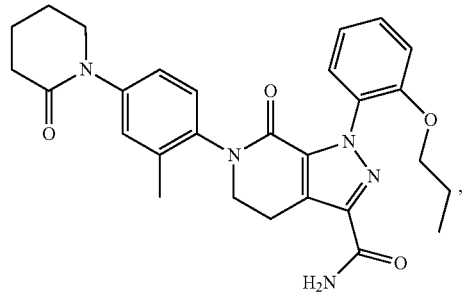
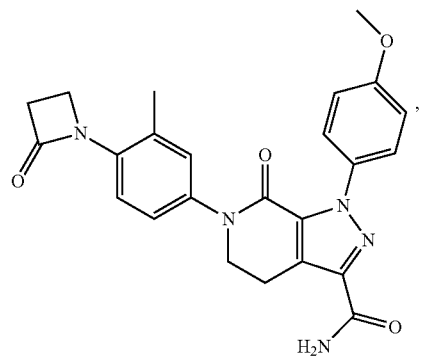
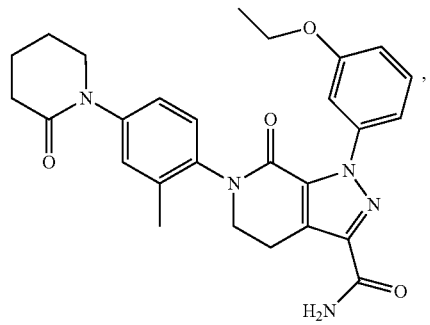

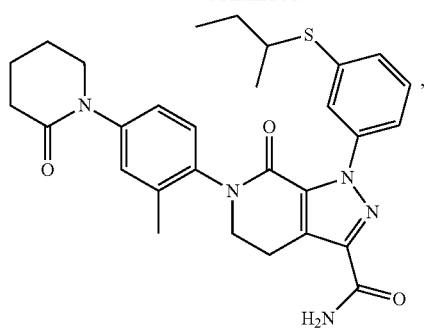
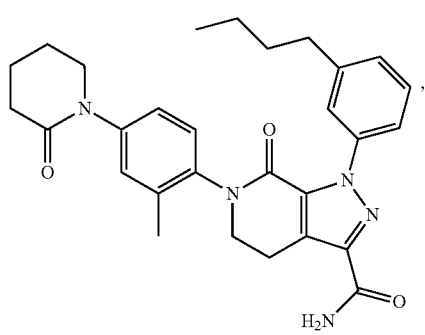
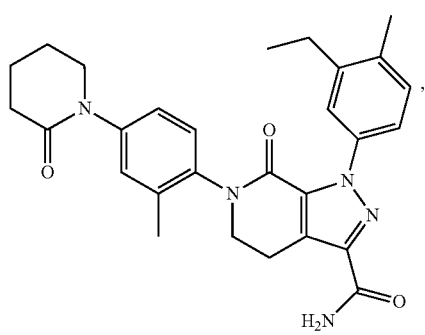
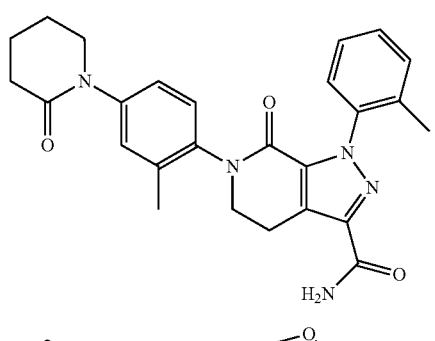
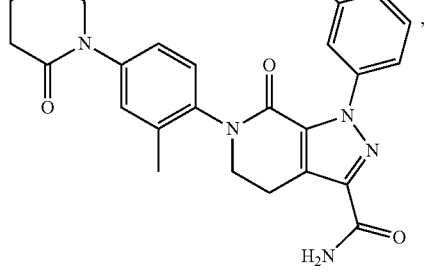
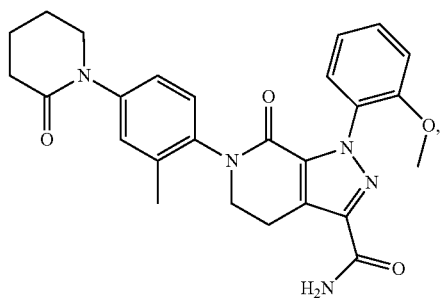
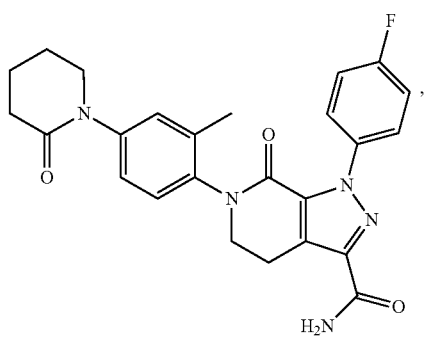
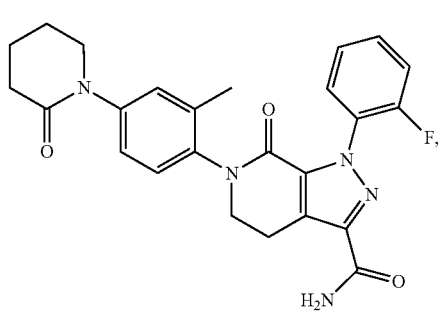
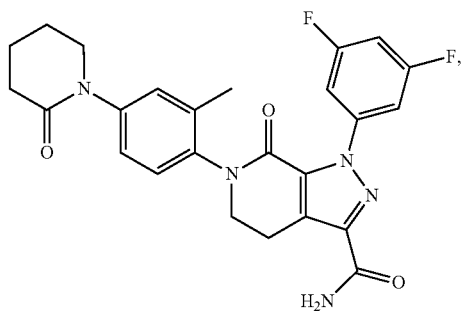
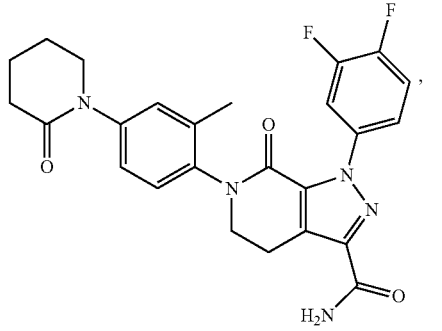

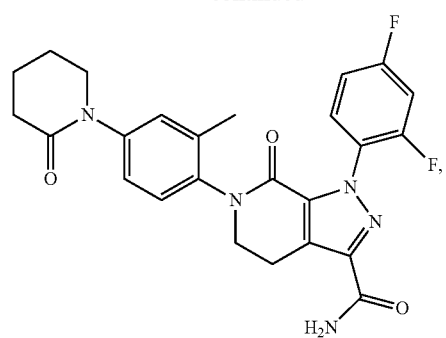
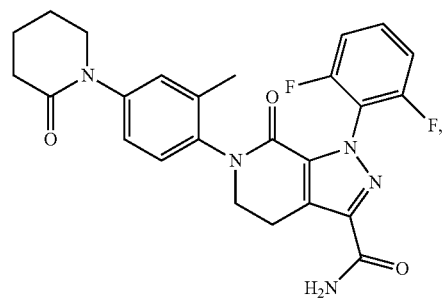
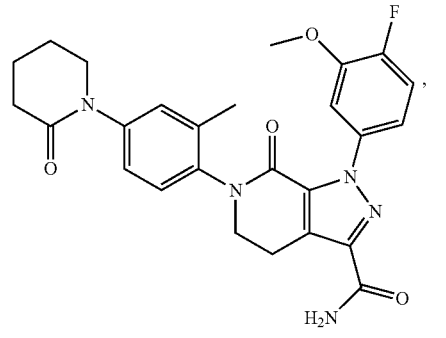
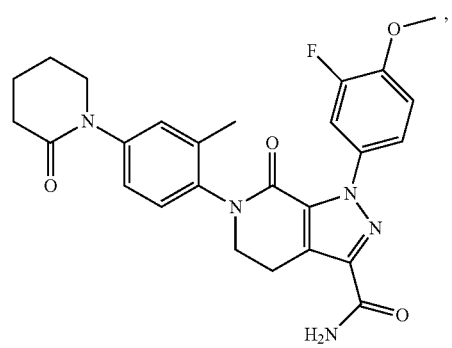
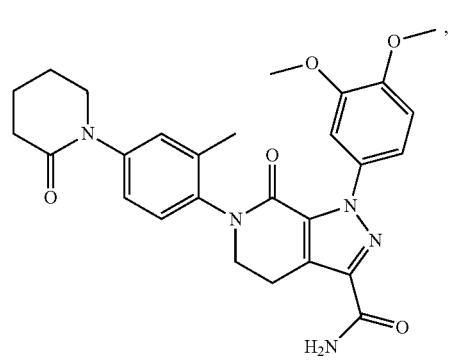
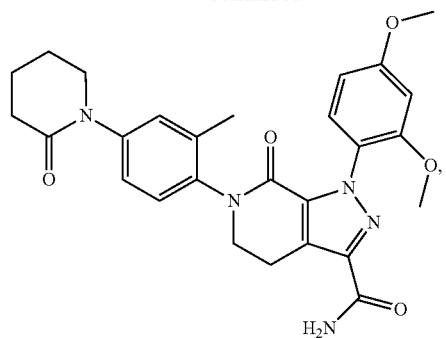
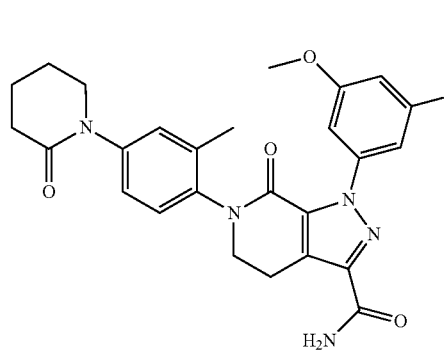
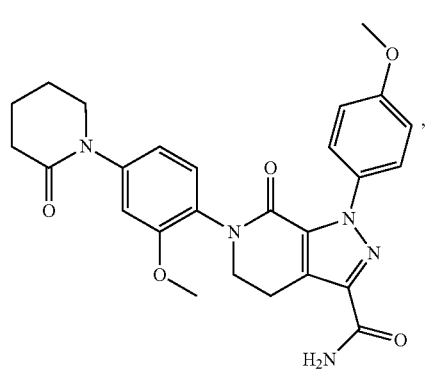
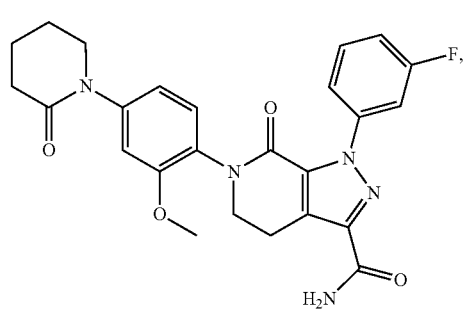
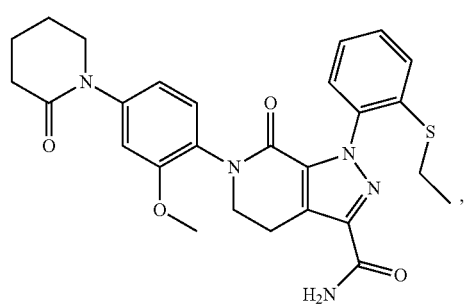

31
-continued
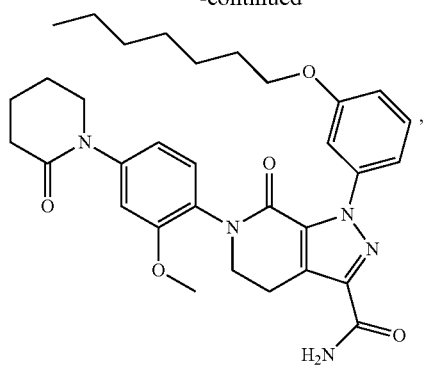
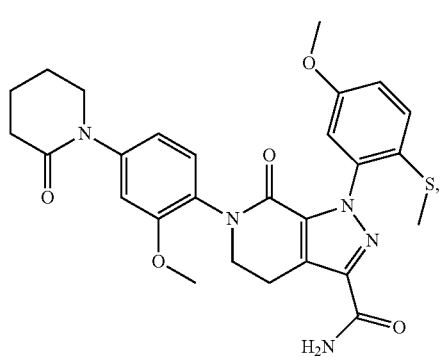
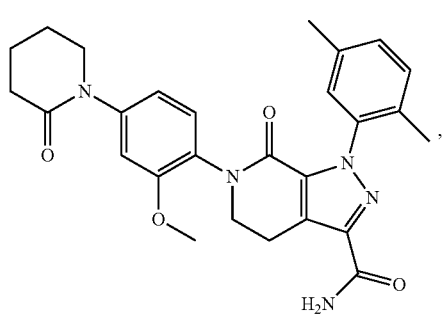
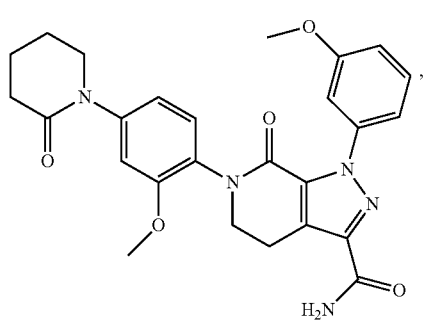
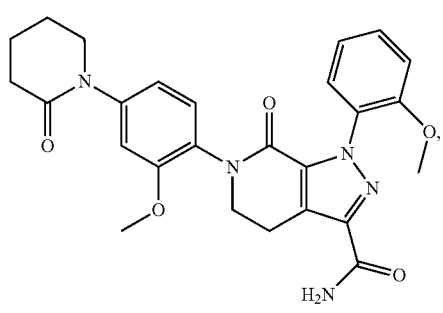
32
-continued
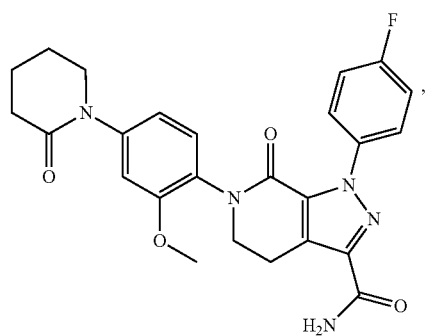
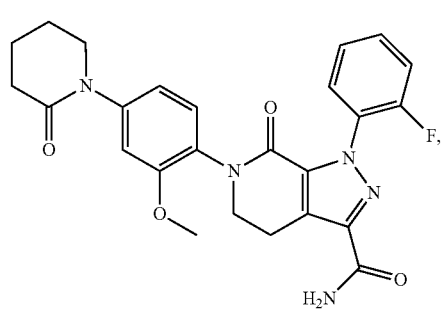
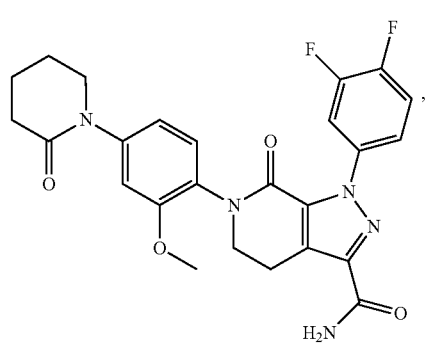
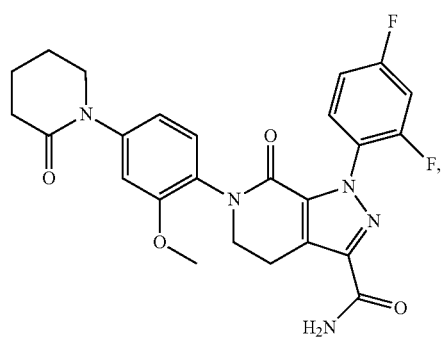
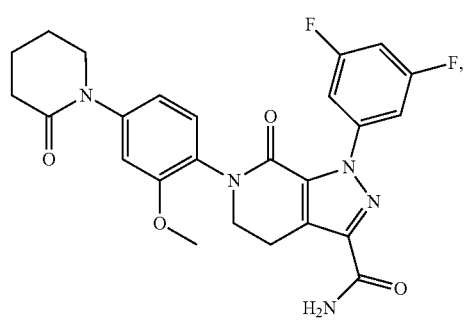

-continued

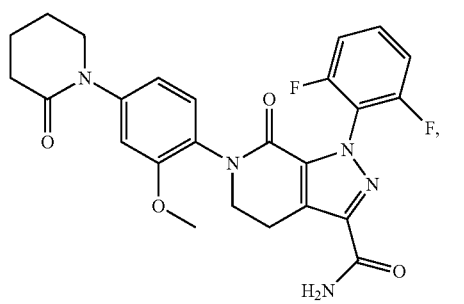

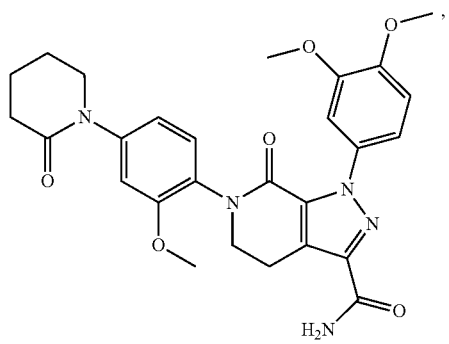

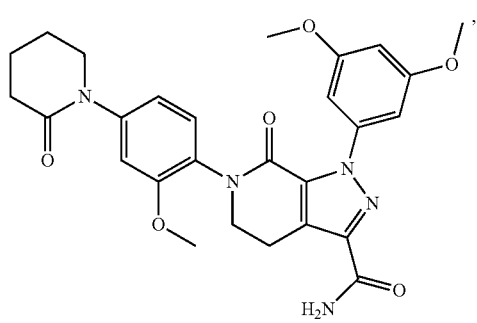

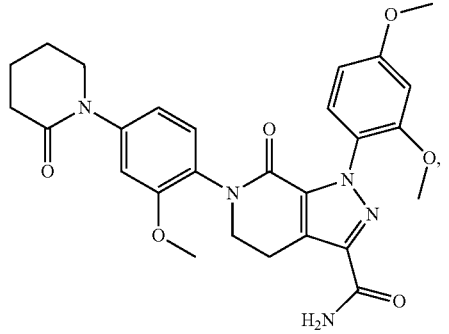

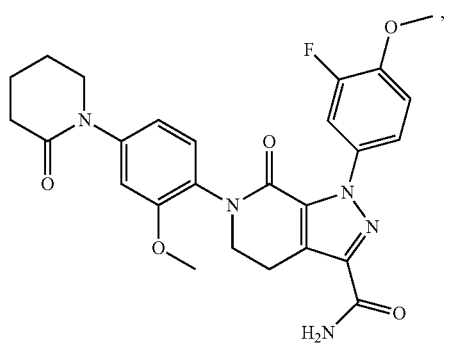

-continued

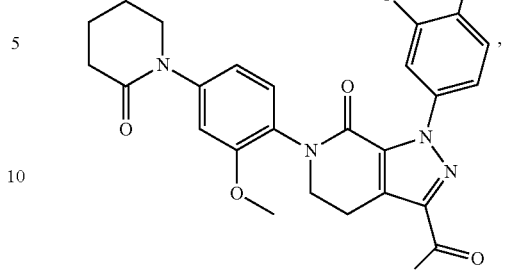

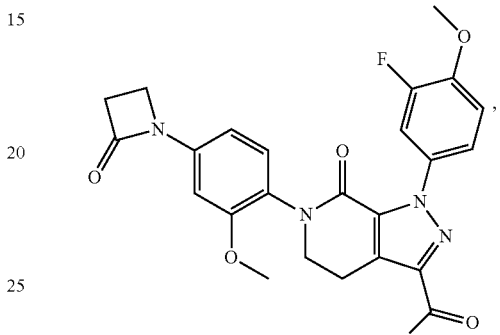

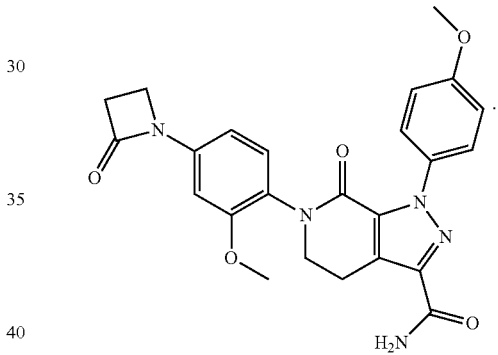

Further, the compounds of the present invention are preferably selected from but not limit to the following compounds:

1-(4-methylphenyl)-7-oxo-6-[4-(2-oxo-piperidin-1-yl)phenyl]-4,5,6,7-tetrahydro-1H-pyrazolo[3,4-c]pyridine-3-carboxamide;

1-(4-methylthiophenyl)-7-oxo-6-[4-(2-oxo-piperidin-1-yl)phenyl]-4,5,6,7-tetrahydro-1H-pyrazolo[3,4-c]pyridine-3-carboxamide;

1-(2-fluorophenyl)-7-oxo-6-[4-(2-oxo-piperidin-1-yl)phenyl]-4,5,6,7-tetrahydro-1H-pyrazolo[3,4-c]pyridine-3-carboxamide;

1-(3-fluoro-4-methoxyphenyl)-7-oxo-6-[4-(2-oxo-piperidin-1-yl)phenyl]-4,5,6,7-tetrahydro-1H-pyrazolo[3,4-c]pyridine-3-carboxamide;

1-(4-methoxyphenyl)-7-oxo-6-[4-(2-oxo-pyrrolidin-1-yl)phenyl]-4,5,6,7-tetrahydro-1H-pyrazolo[3,4-c]pyridine-3-carboxamide;

1-(2-fluorophenyl)-7-oxo-6-[4-(2-oxo-pyrrolidin-1-yl)phenyl]-4,5,6,7-tetrahydro-1H-pyrazolo[3,4-c]pyridine-3-carboxamide;

1-(3-fluoro-4-methoxyphenyl)-7-oxo-6-[4-(2-oxo-pyrrolidin-1-yl)phenyl]-4,5,6,7-tetrahydro-1H-pyrazolo[3,4-c]pyridine-3-carboxamide;

1-(3,5-difluoro-phenyl)-7-oxo-6-[4-(2-oxo-pyrrolidin-1-yl)phenyl]-4,5,6,7-tetrahydro-1H-pyrazolo[3,4-c]pyridine-3-carboxamide;

1-(4-methoxyphenyl)-7-oxo-6-[2-methyl-4-(2-oxo-pyrrolidin-1-yl)phenyl]-4,5,6,7-tetrahydro-1H-pyrazolo[3,4-c]pyridine-3-carboxamide;

1-(2-methoxyphenyl)-7-oxo-6-[2-methyl-4-(2-oxo-pyrrolidin-1-yl)phenyl]-4,5,6,7-tetrahydro-1H-pyrazolo[3,4-c]pyridine-3-carboxamide;

1-(4-methylphenyl)-7-oxo-6-[2-methyl-4-(2-oxo-pyrrolidin-1-yl)phenyl]-4,5,6,7-tetrahydro-1H-pyrazolo[3,4-c]pyridine-3-carboxamide;

1-(4-fluorophenyl)-7-oxo-6-[2-methyl-4-(2-oxo-pyrrolidin-1-yl)phenyl]-4,5,6,7-tetrahydro-1H-pyrazolo[3,4-c]pyridine-3-carboxamide;

1-(2,4-dimethyl-phenyl)-7-oxo-6-[2-methyl-4-(2-oxo-pyrrolidin-1-yl)phenyl]-4,5,6,7-tetrahydro-1H-pyrazolo[3,4-c]pyridine-3-carboxamide;

1-(3,5-difluoro-phenyl)-7-oxo-6-[2-methyl-4-(2-oxo-pyrrolidin-1-yl)phenyl]-4,5,6,7-tetrahydro-1H-pyrazolo[3,4-c]pyridine-3-carboxamide;

1-(3-fluoro-4-methoxyphenyl)-7-oxo-6-[2-methyl-4-(2-oxo-pyrrolidin-1-yl)phenyl]-4,5,6,7-tetrahydro-1H-pyrazolo[3,4-c]pyridine-3-carboxamide;

1-(4-methoxyphenyl)-7-oxo-6-[3-methyl-4-(2-oxo-pyrrolidin-1-yl)phenyl]-4,5,6,7-tetrahydro-1H-pyrazolo[3,4-c]pyridine-3-carboxamide;

1-(3,5-difluorophenyl)-7-oxo-6-[3-methyl-4-(2-oxo-pyrrolidin-1-yl)phenyl]-4,5,6,7-tetrahydro-1H-pyrazolo[3,4-c]pyridine-3-carboxamide;

1-(3-fluoro-4-methoxyphenyl)-7-oxo-6-[3-methyl-4-(2-oxo-pyrrolidin-1-yl)phenyl]-4,5,6,7-tetrahydro-1H-pyrazolo[3,4-c]pyridine-3-carboxamide;

1-(4-methoxyphenyl)-7-oxo-6-[2-methyl-4-(2-oxo-piperidin-1-yl)phenyl]-4,5,6,7-tetrahydro-1H-pyrazolo[3,4-c]pyridine-3-carboxamide;

1-(3-fluorophenyl)-7-oxo-6-[2-methyl-4-(2-oxo-piperidin-1-yl)phenyl]-4,5,6,7-tetrahydro-1H-pyrazolo[3,4-c]pyridine-3-carboxamide;

1-(4-methoxyphenyl)-7-oxo-6-[2-methoxy-4-(2-oxo-piperidin-1-yl)phenyl]-4,5,6,7-tetrahydro-1H-pyrazolo[3,4-c]pyridine-3-carboxamide;

1-(3-fluorophenyl)-7-oxo-6-[2-methoxy-4-(2-oxo-piperidin-1-yl)phenyl]-4,5,6,7-tetrahydro-1H-pyrazolo[3,4-c]pyridine-3-carboxamide.

Another object of the present invention is to provide a preparation method of the above compounds of formula (I), comprising the following steps:

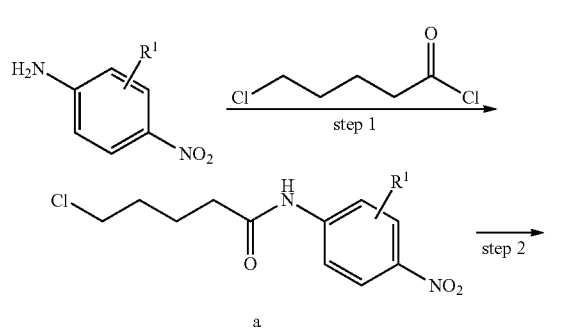

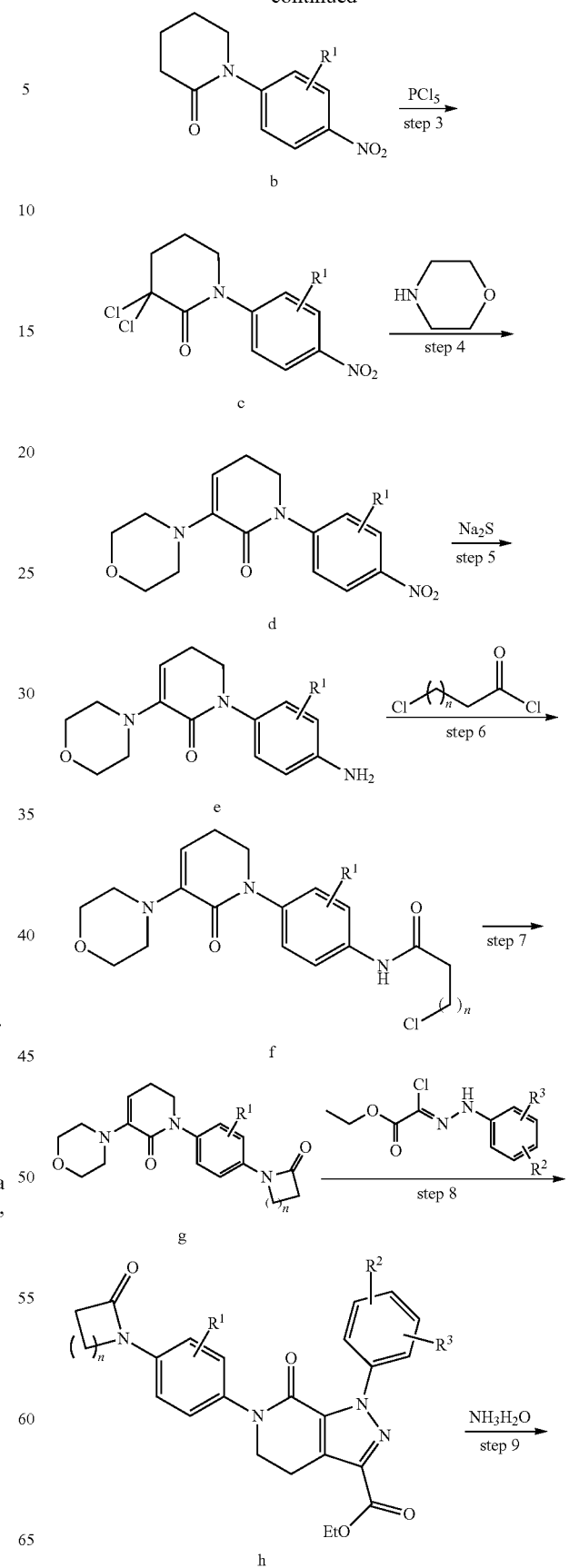

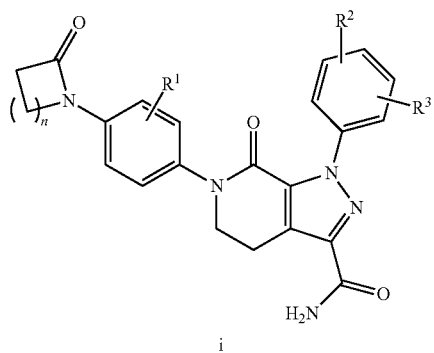

i

The starting raw material paranitroaniline derivative is reacted with 5-chlorovaleryl chloride to generate compound a; the compound a is further subjected to an intramolecular cyclization under alkaline conditions to generate compound b; the compound b is reacted with phosphorus pentachloride to generate compound c; the generated compound c is further reacted with morpholine to generate compound d; the nitro group of the compound d is reduced to generate compound e; the compound e is reacted with a chlorinated acyl chloride derivative again to generate compound f; the compound f is further subjected to an intramolecular cyclization again to generate compound g; the compound g is reacted with an ethyl phenylhydrazinochloroacetate derivative to generate compound h; the compound h is subjected to aminolysis to give the targeting compound I.

Wherein, in the starting raw material paranitroaniline derivatives, $R^1$ is selected from hydrogen atom, $C_1$-$C_{10}$ alkyl or $C_1$-$C_{10}$ alkoxy, wherein any hydrogen atom on $C_1$-$C_{10}$ alkyl or alkoxy can be further replaced by hydroxy or amino; in the starting raw material ethyl phenylhydrazinochloroacetate derivatives, $R^2$ is selected from hydrogen atom, $C_1$-$C_{10}$ alkyl, $C_1$-$C_{10}$ alkoxy, $C_1$-$C_{10}$ alkylthio, fluorine atom, chlorine atom, bromine atom, iodine atom or trifluoromethyl; in the starting raw material ethyl phenylhydrazinochloroacetate derivatives, $R^3$ is selected from hydrogen atom, $C_1$-$C_{10}$ alkyl, $C_1$-$C_{10}$ alkoxy, $C_1$-$C_{10}$ alkylthio, fluorine atom, chlorine atom, bromine atom, iodine atom or trifluoromethyl; in the starting raw material chlorinated acyl chloride derivatives used in step 6, n=1, 2 or 3.

Further preferably, $R^1$ is selected from hydrogen atom, $C_1$-$C_5$ alkyl or $C_1$-$C_5$ alkoxy; $R^2$ is selected from hydrogen atom, $C_1$-$C_5$ alkyl, $C_1$-$C_5$ alkoxy, $C_1$-$C_5$ alkylthio, fluorine atom, chlorine atom or trifluoromethyl; $R^3$ is selected from hydrogen atom, $C_1$-$C_5$ alkyl, $C_1$-$C_5$ alkoxy, $C_1$-$C_5$ alkylthio, fluorine atom, chlorine atom or trifluoromethyl; n=1, 2 or 3.

More preferably, $R^1$ is selected from hydrogen atom, $C_1$-$C_3$ alkyl or $C_1$-$C_3$ alkoxy; $R^2$ is selected from hydrogen atom, $C_1$-$C_3$ alkyl, $C_1$-$C_3$ alkoxy, $C_1$-$C_3$ alkylthio, fluorine atom or trifluoromethyl; $R^3$ is selected from hydrogen atom, $C_1$-$C_3$ alkyl, $C_1$-$C_3$ alkoxy, $C_1$-$C_3$ alkylthio, fluorine atom or trifluoromethyl; n=1, 2 or 3.

More preferably, $R^1$ is selected from hydrogen atom, methyl or methoxyl; $R^2$ is selected from methyl, methoxy, methylthio or fluorine atom; $R^3$ is selected from hydrogen atom, methyl, methoxy, methylthio or fluorine atom; n=1, 2 or 3.

More preferably, $R^1$ is selected from hydrogen atom, methyl or methoxyl; $R^2$ is selected from methyl, methoxy, methylthio or fluorine atom; $R^3$ is selected from hydrogen atom, methyl, methoxy, methylthio or fluorine atom; n=2 or 3.

More preferably, $R^1$ is selected from hydrogen atom or methyl; $R^2$ is selected from methyl, methoxy or fluorine atom; $R^3$ is selected from hydrogen atom, methyl, methoxy or fluorine atom; n=2.

Most preferably, $R^1$ is selected from methyl; $R^2$ is selected from methyl, methoxy or fluorine atom; $R^3$ is selected from hydrogen atom, methyl, methoxy or fluorine atom; n=2.

Furthermore, preferably, $R^1$ is selected from hydrogen atom, methyl or methoxy; $R^2$ is selected from methyl, methoxy, methylthio or fluorine atom; $R^3$ is selected from hydrogen atom, methyl, methoxy, methylthio or fluorine atom; n=3.

Further preferably, $R^1$ is selected from methyl or methoxy; $R^2$ is selected from methyl, methoxy, methylthio or fluorine atom; $R^3$ is selected from hydrogen atom, methyl, methoxy, methylthio or fluorine atom; n=3.

Another object of the present invention is to provide the use of the above compound of general formula (I) in preparing Factor Xa inhibitor, more specifically in preparing anticoagulant, especially to provide the use of the above compound as shown in general formula (I) in preparing a medicament for preventing and/or treating thrombosis or embolism. In the human FXa inhibition assay, the compounds of the present invention exhibit excellent FXa inhibitory activity; in the pharmacodynamic assay for affecting APTT of healthy mice, the compounds of the present invention can significantly increase the APTT values of mice at 60 min after administration, and show a good anticoagulant effect; in pharmacokinetic studies on healthy rats, the compounds of the present invention exhibit excellent pharmacokinetic behaviors.

DETAILED DESCRIPTION

The present invention will be described in further details with the examples, but does not intend to limit the scope of the present invention, while any equivalent in this field in accordance with the disclosure of the present invention falls within the scope of the present invention.

Structures of compounds are verified by mass spectrometry (MS) or nuclear magnetic resonance ($^1$H NMR).

Displacement (δ) of the nuclear magnetic resonance ($^1$H NMR) is given in a unit of parts per million (ppm); measurement by nuclear magnetic resonance ($^1$H NMR) is carried out on Bruker AVANCE-400 NMR instrument, wherein the measuring solvent is deuterated chloroform (CDCl$_3$), the internal standard is tetramethyl silane (TMS), and the chemical displacement is given in a unit of parts per million (ppm).

Measurement by mass spectrum (MS) is carried out on FINNIGAN LCQAd (ESI) mass spectrometer (manufacturer: Therm, type: Finnigan LCQ advantage MAX).

Yantai Huanghai HSGF254 or Qingdao GF254 silica gel plate is used in the thin layer silica gel assay.

Yantai Huanghai 200-300 mesh silica gel is generally used as a carrier in column chromatography.

Unless otherwise specified, the reactions mentioned in the present invention are carried out under the nitrogen atmosphere.

In the present invention, the term "nitrogen atmosphere" refers, for example, to connecting the reaction flask to a nitrogen balloon with 1 L volume.

Unless otherwise specified, the solutions mentioned in the reaction of the present invention refer to the aqueous solutions.

In the present invention, the term "room temperature" refers to the temperature between 10° C. and 25° C.

In one embodiment, the present invention relates to pyridine derivatives having the structure represented by the general formula (I):

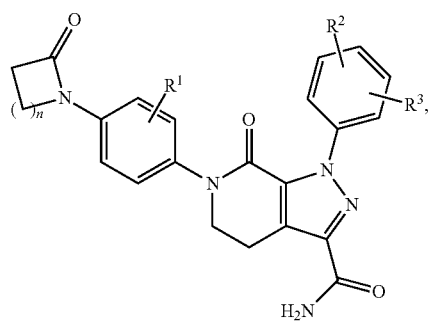

I

Wherein, $R^1$ is selected from hydrogen atom, $C_1$-$C_5$ alkyl or $C_1$-$C_5$ alkoxy; $R^2$ is selected from hydrogen atom, $C_1$-$C_5$ alkyl, $C_1$-$C_5$ alkoxy, $C_1$-$C_5$ alkylthio, fluorine atom, chlorine atom or trifluoromethyl; $R^3$ is selected from hydrogen atom, $C_1$-$C_5$ alkyl, $C_1$-$C_5$ alkoxy, $C_1$-$C_5$ alkylthio, fluorine atom, chlorine atom or trifluoromethyl; n=2 or 3.

In a preferred embodiment, $R^1$ is selected from hydrogen atom, $C_1$-$C_3$ alkyl or $C_1$-$C_3$ alkoxy; $R^2$ is selected from hydrogen atom, $C_1$-$C_3$ alkyl, $C_1$-$C_3$ alkoxy, $C_1$-$C_3$ alkylthio, fluorine atom or trifluoromethyl; $R^3$ is selected from hydrogen atom, $C_1$-$C_3$ alkyl, $C_1$-$C_3$ alkoxy, $C_1$-$C_3$ alkylthio, fluorine atom or trifluoromethyl; n=2 or 3.

In a more preferred embodiment, $R^1$ is selected from hydrogen atom, methyl or methoxyl; $R^2$ is selected from methyl, methoxy, methylthio or fluorine atom; $R^3$ is selected from hydrogen atom, methyl, methoxy, methylthio or fluorine atom; n=2.

In the most preferred embodiment, $R^1$ is selected from methyl; $R^2$ is selected from methyl, methoxy or fluorine atom; $R^3$ is selected from hydrogen atom, methyl, methoxy or fluorine atom; n=2.

Furthermore, in a preferred embodiment of the present invention, $R^1$ is selected from methyl or methoxy; $R^2$ is selected from methyl, methoxy, methylthio or fluorine atom; $R^3$ is selected from hydrogen atom, methyl, methoxy, methylthio or fluorine atom; n=3.

In another embodiment, the present invention provides the use of the above compounds of the general formula (I) in preparing Factor Xa inhibitor, more specifically provides the use in preparing anticoagulant, especially provides the use of the compounds as shown in general formula (I) in preparing a medicament for preventing and/or treating thrombosis or embolism.

EXAMPLES

Example 1: Preparation of 1-(4-methylphenyl)-7-oxo-6-[4-(2-oxo-piperidin-1-yl)phenyl]-4,5,6,7-tetrahydro-1H-pyrazolo[3,4-c]pyridine-3-carboxamide

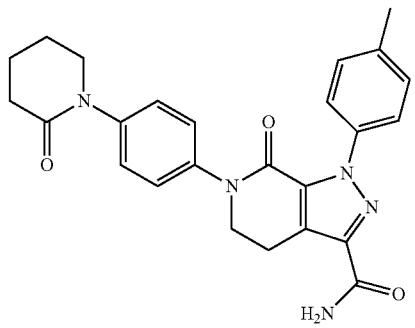 [SMILES: Cc1ccc(-n2nc(C(N)=O)c3c2C(=O)N(c2ccc(N4CCCCC4=O)cc2)CC3)cc1]

Preparation scheme is shown below:

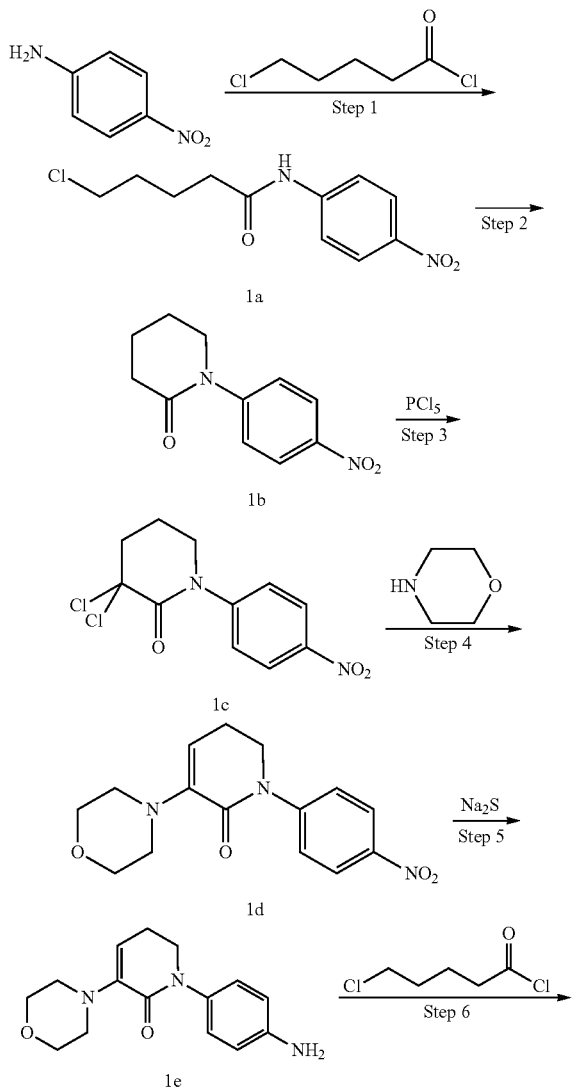

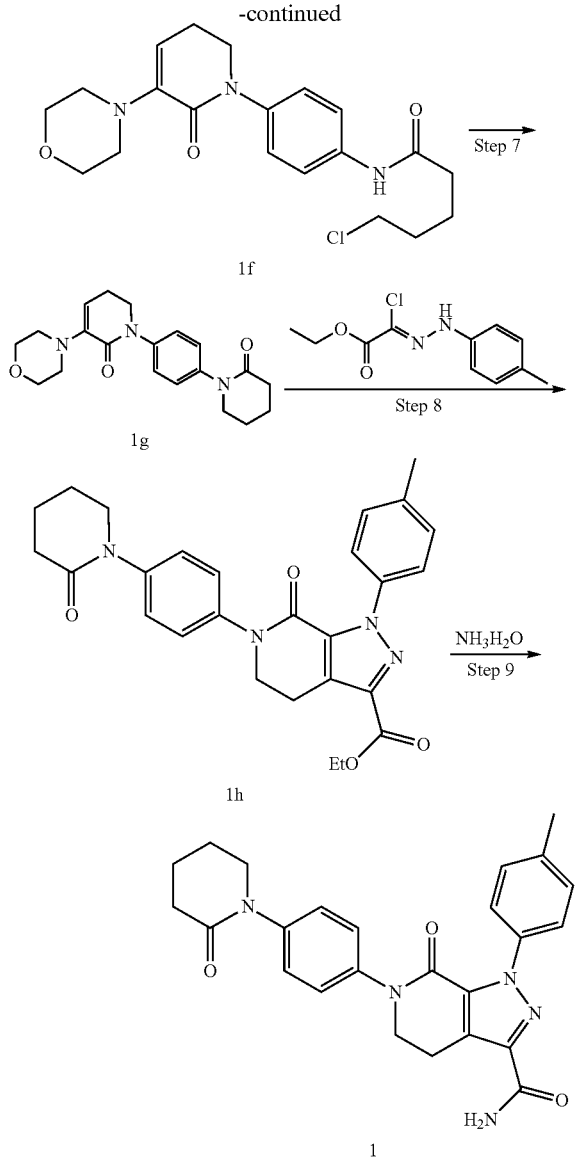

Step 1: Preparation of Compound 1a

4-Nitroaniline (50.0 g, 0.36 mol) was dissolved in tetrahydrofuran (260 ml). N,N-diisopropylethylamine (58.0 g, 0.45 mol) was added, and cooled in ice bath to 5° C. or lower. 5-chlorovaleryl chloride (67.4 g, 0.43 mol) was added dropwise to obtain a reaction mixture. The reaction mixture was reacted overnight at room temperature. TLC was used to monitor the reaction progress. After the reaction was completed, tetrahydrofuran was removed by distillation under reduced pressure, ethyl acetate was added, then the dissolved solution was washed with water for three times, dried over anhydrous magnesium sulfate, filtered, and the solvent was distilled off under reduced pressure to give compound 1a (82.0 g, light yellow solid), yield: 88.2%.

MS m/z (ES): 257.1 [M+1]

Step 2: Preparation of Compound 1b

The compound 1a (82.0 g, 0.32 mol) was dissolved in tetrahydrofuran (350 ml). Sodium hydride (15.3 g, 0.64 mol) was added portion-wise under an ice bath to obtain a reaction mixture. Then the reaction mixture was reacted overnight at room temperature. TLC was used to monitor the reaction progress. After the reaction was completed, ice-water was added into the reaction mixture under an ice bath to quench sodium hydride. After removing tetrahydrofuran by distillation under reduced pressure, the residue was extracted twice with ethyl acetate, dried over anhydrous magnesium sulfate, filtered, and the solvent was distilled off under reduced pressure. The residue was purified by column chromatography to give 1b (55.0 g, yellow solid), yield: 78.3%.

MS m/z (ES): 221.1 [M+1]

Step 3: Preparation of Compound 1c

The compound 1b (55.0 g, 0.25 mol) was dissolved in dichloromethane (250 ml). Phosphorus pentachloride (156 g, 0.75 mol) was added portion-wise under an ice bath to obtain a reaction mixture. The reaction mixture was refluxed at 40° C. When the reaction solution generated little bubble, TLC was used to monitor the reaction progress. After the reaction was completed, ice-water was added into the reaction mixture under an ice bath to quench phosphorus pentachloride. The solution was separated, washed with water for three times, dried over anhydrous magnesium sulfate, filtered, and the solvent was removed by distillation under reduced pressure to give compound 1c (67.2 g, yellow solid), yield: 93.1%.

MS m/z (ES): 289.0, 291.0 [M+1]

Step 4: Preparation of Compound 1d

The compound 1c (19.0 g, 65.7 mmol) was dissolved in morpholine (100 ml) to obtain a reaction mixture, which was refluxed at 120° C. for 2 hours. TLC was used to monitor the reaction progress. After the reaction was completed, most of morpholine was removed by distillation under reduced pressure, the residue, as a yellow solid, was washed with water by stirring for 1 hour and filtered. The filter cake was washed with water for three times, air-dried for 24 hours to give compound 1d (18.0 g, yellow solid), yield: 90.4%.

MS m/z (ES): 304.1 [M+1]

Step 5: Preparation of Compound 1e

The compound 1d (18.0 g, 59.3 mmol) was dissolved in ethanol (180 ml). Sodium sulfide nonahydrate (28.4 g, 118.6 mmol) was added, and then water (60 ml) was added to obtain a reaction mixture, which was refluxed overnight at 50° C. TLC was used to monitor the reaction progress. After the reaction was completed, ethanol was removed by distillation under reduced pressure, the residue was extracted by ethyl acetate for three times, the combined organic phases were dried over anhydrous magnesium sulfate, filtered, and the solvent was removed by distillation under reduced pressure to give compound 1e (12.0 g, yellow solid) yield: 74.1%.

MS m/z (ES): 274.1 [M+1]

Step 6: Preparation of Compound 1f

The compound 1e (10.0 g, 36.6 mmol) was dissolved in tetrahydrofuran (200 ml). N,N-diisopropylethylamine (7.0 g, 54.3 mmol) was added, and cooled in ice bath. 5-chlorovaleryl chloride (7.37 g, 47.6 mmol) was added dropwise to obtain a reaction mixture. The reaction mixture was reacted overnight at room temperature. TLC was used to monitor the reaction progress. After the reaction was completed, water was added into the reaction mixture, which was separated and washed with water for three times, dried over anhydrous magnesium sulfate, filtered, and the solvent was distilled off under reduced pressure to give compound 1f (12.8 g, yellow solid), yield: 89.5%.

MS m/z (ES): 392.2 [M+1]

Step 7: Preparation of Compound 1 g

The compound 1f (12.8 g, 32.7 mmol) was dissolved in tetrahydrofuran (250 ml). Sodium hydride (1.73 g, 72.1 mmol) was added portion-wise under an ice bath to obtain a reaction mixture. The reaction mixture was reacted overnight at room temperature. TLC was used to monitor the reaction progress. After the reaction was completed, ice-water was added into the reaction solution under an ice bath to quench sodium hydride. After removing tetrahydrofuran by distillation under reduced pressure, the residue was extracted twice by dichloromethane, the combined organic phases were dried over anhydrous magnesium sulfate, filtered, and the solvent was distilled off under reduced pressure. The residue was purified by column chromatography to give compound 1 g (9.8 g, yellow solid), yield: 84.5%.

MS m/z (ES): 356.2 [M+1]

Step 8: Preparation of Compound 1h

The compound 1 g (280 mg, 0.79 mmol) was dissolved in ethyl acetate (10 ml). Ethyl [(4-methylphenyl)hydrazino]chloroacetate (246 mg, 1.02 mmol) and triethylamine (242 mg, 2.4 mmol) were added at room temperature to give a reaction mixture, which was refluxed overnight at 80° C. TLC was used to monitor the reaction progress. After the reaction was completed, 4N HCl (1.6 ml) was slowly added dropwise at room temperature to obtain a reaction mixture, which was reacted overnight at room temperature. TLC was used to monitor the reaction progress. After the reaction was completed, the reaction mixture was purified by column chromatography to give compound 1h (295 mg, yellow solid), yield: 79.3%.

MS m/z (ES): 473.2 [M+1]

Step 9: Preparation of 1-(4-methylphenyl)-7-oxo-6-[4-(2-oxo-piperidin-1-yl)phenyl]-4,5,6,7-tetrahydro-1H-pyrazolo[3,4-c]pyridine-3-carboxamide 1

The compound 1h (295 mg, 0.62 mmol) was dissolved in methanol (6 ml). Aqueous ammonia (4 ml) was added to give a reaction mixture, which was refluxed overnight at 55° C. TLC was used to monitor the reaction progress. After the reaction was completed, the reaction mixture was purified by column chromatography to give compound 1 (190 mg, off-white solid), yield: 68.6%.

MS m/z (ES): 444.2 [M+1]

$^1$H NMR (400 MHz, CDCl$_3$) δ 7.43 (d, J=8.3 Hz, 2H), 7.34 (d, J=8.7 Hz, 2H), 7.26-7.22 (m, 4H), 6.87 (br s, 1H), 5.57 (br s, 1H), 4.12 (t, J=6.7 Hz, 2H), 3.61-3.58 (m, 2H), 3.37 (t, J=6.7 Hz, 2H), 2.55 (t, J=5.4 Hz, 2H), 2.38 (s, 3H), 1.94-1.92 (m, 4H).

Example 2: Preparation of 1-(4-methylthiophenyl)-7-oxo-6-[4-(2-oxo-piperidin-1-yl)phenyl]-4,5,6,7-tetrahydro-1H-pyrazolo[3,4-c]pyridine-3-carboxamide

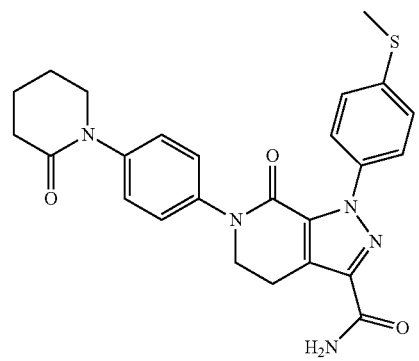 [SMILES: CSc1ccc(-n2nc(C(N)=O)c3c2C(=O)N(c2ccc(N4CCCCC4=O)cc2)CC3)cc1]

Preparation scheme is shown below:

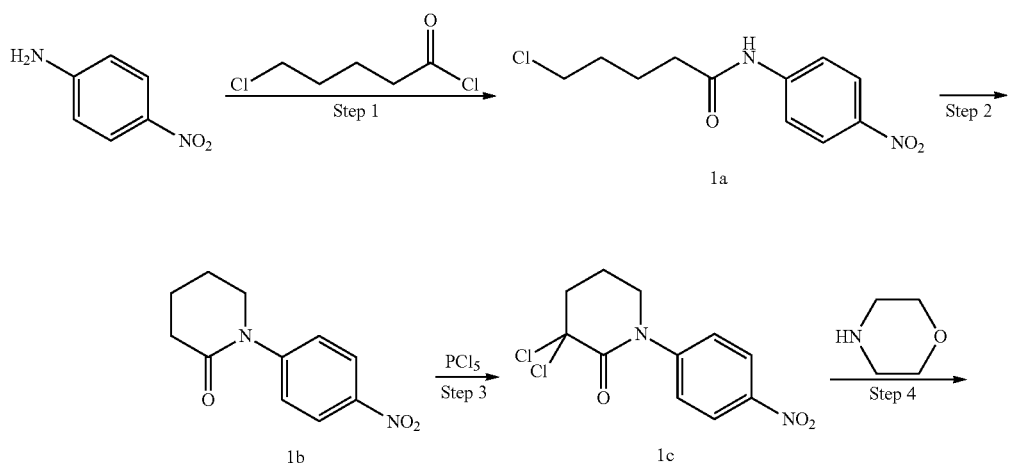

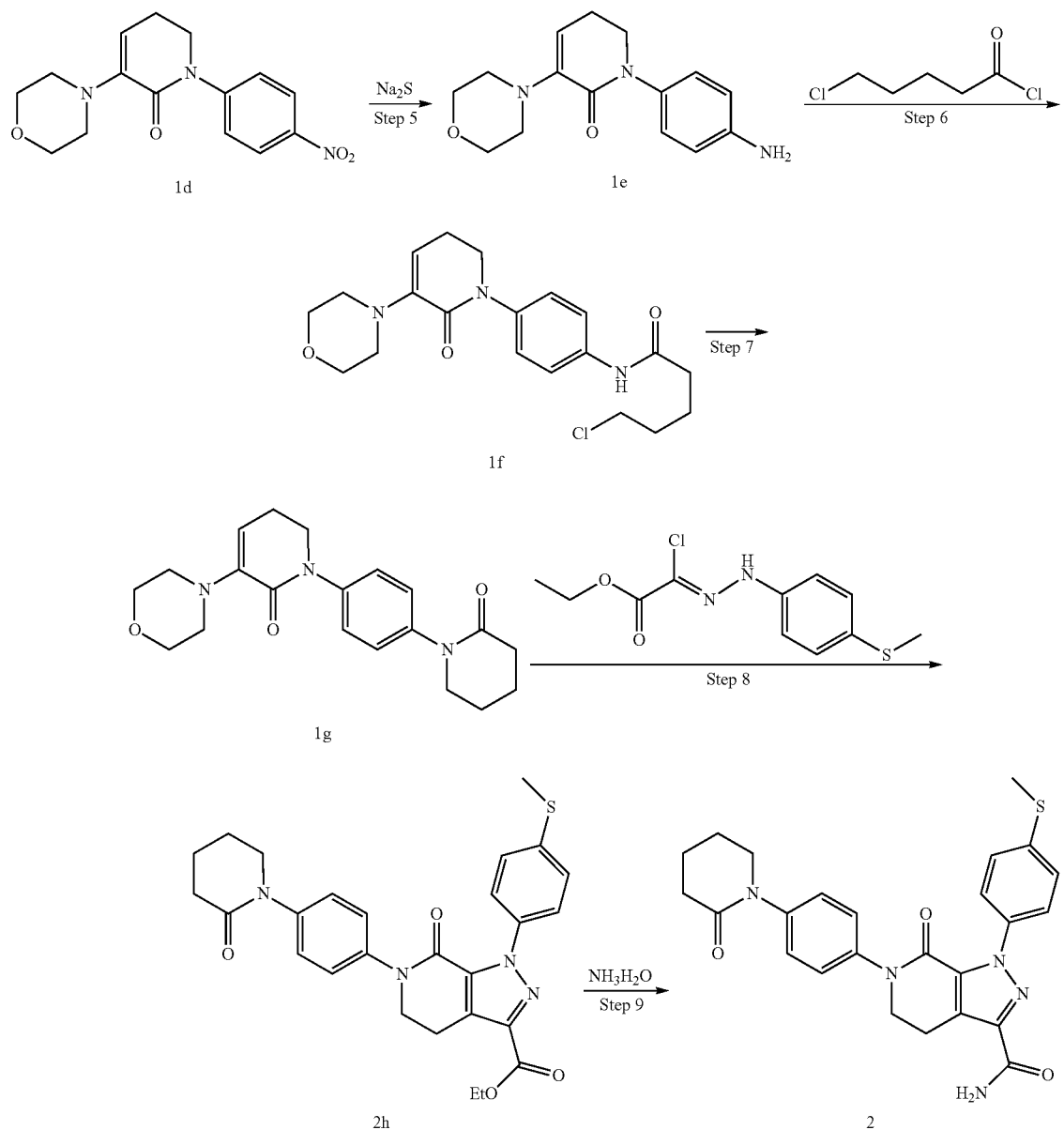

Step 1 was carried out in the same manner as the step 1 in Example 1;

Step 2 was carried out in the same manner as the step 2 in Example 1;

Step 3 was carried out in the same manner as the step 3 in Example 1;

Step 4 was carried out in the same manner as the step 4 in Example 1;

Step 5 was carried out in the same manner as the step 5 in Example 1;

Step 6 was carried out in the same manner as the step 6 in Example 1;

Step 7 was carried out in the same manner as the step 7 in Example 1;

Step 8: Preparation of Compound 2h

The compound 1 g (280 mg, 0.79 mmol) was dissolved in ethyl acetate (10 ml). Ethyl [(4-methylthiophenyl)hydrazino]chloroacetate (280 mg, 1.03 mmol) and triethylamine (242 mg, 2.4 mmol) were added at room temperature to give a reaction mixture, which was refluxed overnight at 80° C. TLC was used to monitor the reaction progress. After the reaction was completed, 4N HCl (1.6 ml) was slowly added dropwise at room temperature to obtain a reaction mixture, which was reacted overnight at room temperature. TLC was used to monitor the reaction progress. After the reaction was completed, the reaction mixture was purified by column chromatography to give compound 2h (205 mg, yellow solid), yield: 50.8%.

MS m/z (ES): 505.2 [M+1]

Step 9: Preparation of 1-(4-methylthiophenyl)-7-oxo-6-[4-(2-oxo-piperidin-1-yl)phenyl]-4,5,6,7-tetrahydro-1H-pyrazolo[3,4-c]pyridine-3-carboxamide 2

The compound 2h (205 mg, 0.41 mmol) was dissolved in methanol (6 ml). Aqueous ammonia (4 ml) was added to give a reaction mixture, which was refluxed overnight at 55° C. TLC was used to monitor the reaction progress. After the reaction was completed, the reaction mixture was purified by column chromatography to give compound 2 (130 mg, light yellow solid), yield: 67.3%.

MS m/z (ES): 476.2 [M+1]

$^1$H NMR (400 MHz, CDCl$_3$) δ 7.48 (d, J=8.6 Hz, 2H), 7.34 (d, J=8.7 Hz, 2H), 7.29-7.25 (m, 4H), 6.86 (br s, 1H), 5.57 (br s, 1H), 4.12 (t, J=6.7 Hz, 2H), 3.61-3.58 (m, 2H), 3.38 (t, J=6.7 Hz, 2H), 2.55 (t, J=5.6 Hz, 2H), 2.48 (s, 3H), 1.95-1.93 (m, 4H).

Example 3: Preparation of 1-(2-fluorophenyl)-7-oxo-6-[4-(2-oxo-piperidin-1-yl)phenyl]-4,5,6,7-tetrahydro-1H-pyrazolo[3,4-c]pyridine-3-carboxamide

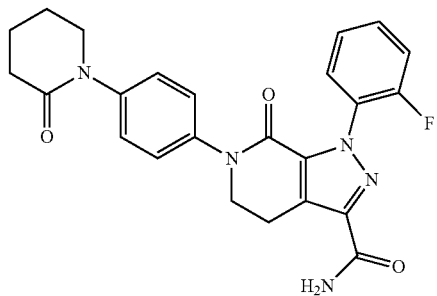 [SMILES: NC(=O)c1nn(-c2ccccc2F)c2c1CCN(c1ccc(N3CCCCC3=O)cc1)C2=O]

Preparation scheme is shown below:

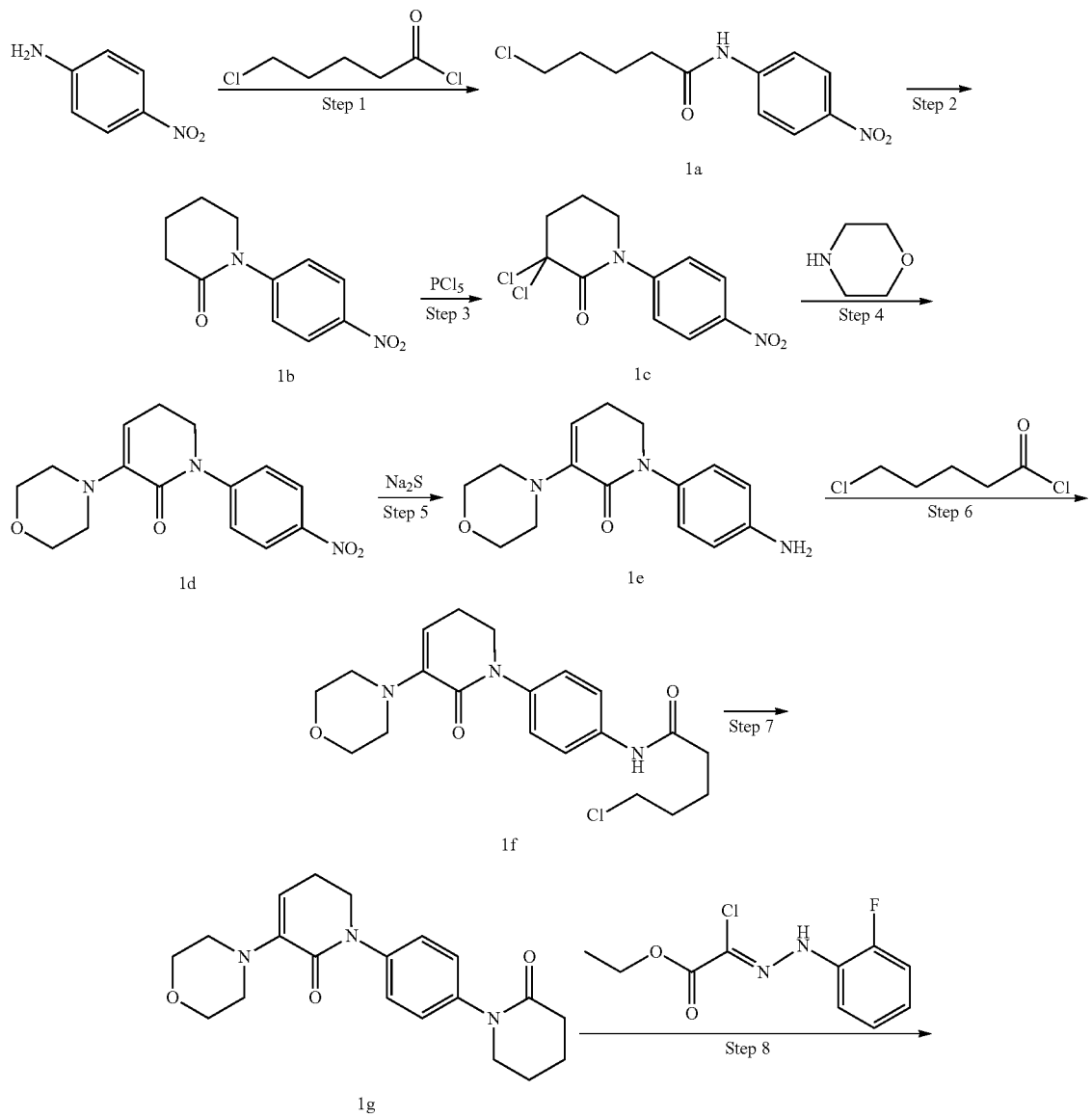

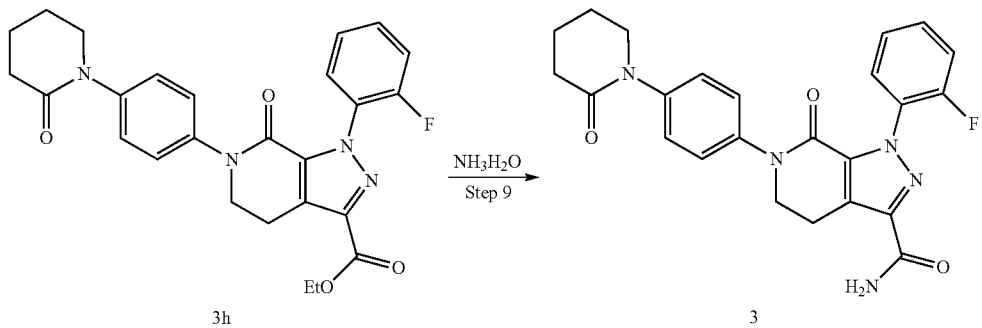

Step 1 was carried out in the same manner as the step 1 in Example 1;
Step 2 was carried out in the same manner as the step 2 in Example 1;
Step 3 was carried out in the same manner as the step 3 in Example 1;
Step 4 was carried out in the same manner as the step 4 in Example 1;
Step 5 was carried out in the same manner as the step 5 in Example 1;
Step 6 was carried out in the same manner as the step 6 in Example 1;
Step 7 was carried out in the same manner as the step 7 in Example 1;

Step 8: Preparation of Compound 3h

The compound 1 g (280 mg, 0.79 mmol) was dissolved in ethyl acetate (10 ml). Ethyl [(2-fluorophenyl)hydrazino]chloroacetate (255 mg, 1.04 mmol) and triethylamine (242 mg, 2.4 mmol) were added at room temperature to give a reaction mixture, which was refluxed overnight at 80° C. TLC was used to monitor the reaction progress. After the reaction was completed, 4N HCl (1.6 ml) was slowly added dropwise at room temperature to obtain a reaction mixture, which was reacted overnight at room temperature. TLC was used to monitor the reaction progress. After the reaction was completed, the reaction mixture was purified by column chromatography to give compound 3h (255 mg, yellow solid), yield: 67.9%.

MS m/z (ES): 477.2 [M+1]

Step 9: Preparation of 1-(2-fluorophenyl)-7-oxo-6-[4-(2-oxo-piperidin-1-yl)phenyl]-4,5,6,7-tetrahydro-1H-pyrazolo[3,4-c]pyridine-3-carboxamide 3

The compound 3h (255 mg, 0.54 mmol) was dissolved in methanol (6 ml). Aqueous ammonia (4 ml) was added to give a reaction mixture, which was refluxed overnight at 55° C. TLC was used to monitor the reaction progress. After the reaction was completed, the reaction mixture was purified by column chromatography to give 3 (160 mg, light yellow solid), yield: 66.8%.

MS m/z (ES): 448.2 [M+1]

$^1$H NMR (400 MHz, CDCl$_3$) δ7.53-7.49 (m, 1H), 7.45-7.41 (m, 1H), 7.34 (d, J=8.7 Hz, 2H), 7.26-7.24 (m, 3H), 7.21-7.17 (m, 1H), 6.83 (br s, 1H), 5.56 (br s, 1H), 4.13 (t, J=6.7 Hz, 2H), 3.59-3.58 (m, 2H), 3.38 (t, J=6.7 Hz, 2H), 2.55 (t, J=5.3 Hz, 2H), 1.93-1.92 (m, 4H).

Example 4: Preparation of 1-(3-fluoro-4-methoxyphenyl)-7-oxo-6-[4-(2-oxo-piperidin-1-yl)phenyl]-4,5,6,7-tetrahydro-1H-pyrazolo[3,4-c]pyridine-3-carboxamide

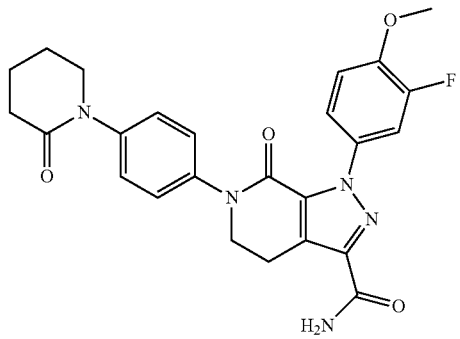 [SMILES: COc1ccc(-n2nc(C(N)=O)c3c2C(=O)N(c2ccc(N4CCCCC4=O)cc2)CC3)cc1F]

Preparation scheme is shown below:

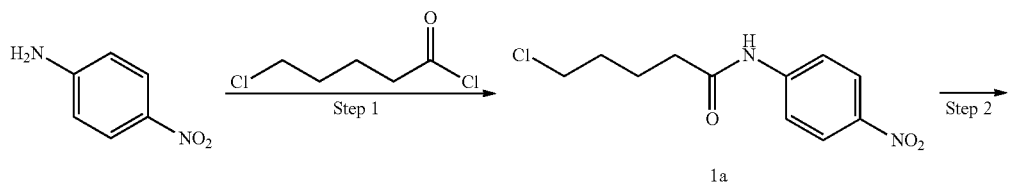

-continued

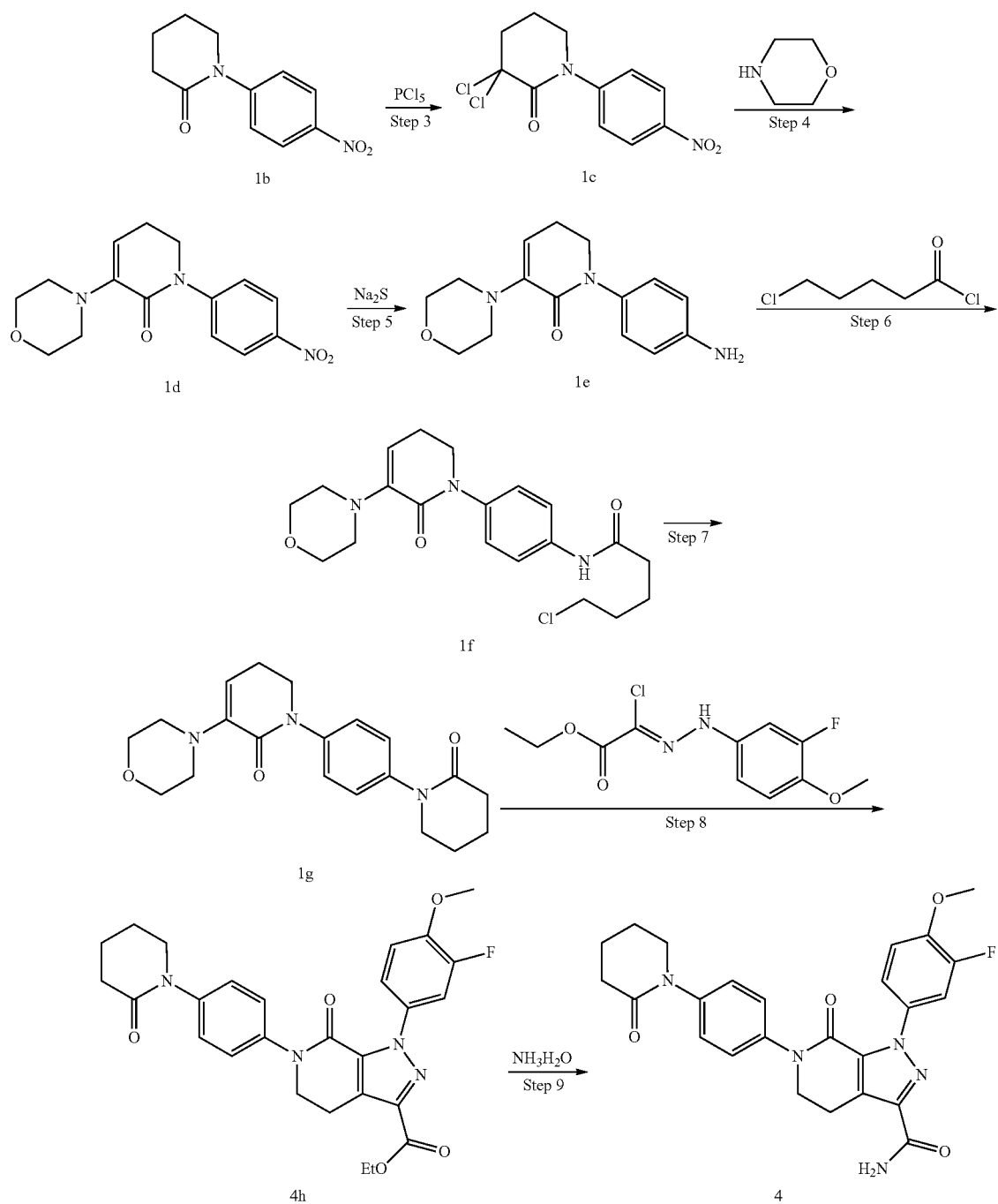

Step 1 was carried out in the same manner as the step 1 in Example 1;

Step 2 was carried out in the same manner as the step 2 in Example 1;

Step 3 was carried out in the same manner as the step 3 in Example 1;

Step 4 was carried out in the same manner as the step 4 in Example 1;

Step 5 was carried out in the same manner as the step 5 in Example 1;

Step 6 was carried out in the same manner as the step 6 in Example 1;

Step 7 was carried out in the same manner as the step 7 in Example 1;

Step 8: Preparation of Compound 4h

The compound 1 g (280 mg, 0.79 mmol) was dissolved in ethyl acetate (10 ml). Ethyl [(3-fluoro-4-methoxyphenyl) hydrazino]chloroacetate (286 mg, 1.04 mmol) and triethylamine (242 mg, 2.4 mmol) were added at room temperature to give a reaction mixture, which was refluxed overnight at 80° C. TLC was used to monitor the reaction progress. After the reaction was completed, 4N HCl (1.6 ml) was slowly added dropwise at room temperature to obtain a reaction mixture, which was reacted overnight at room temperature. TLC was used to monitor the reaction progress. After the reaction was completed, the reaction mixture was purified by column chromatography to give compound 4h (344 mg, yellow solid), yield: 86.2%.

MS m/z (ES): 507.2 [M+1]

Step 9: Preparation of 1-(3-fluoro-4-methoxyphenyl)-7-oxo-6-[4-(2-oxo-piperidin-1-yl)phenyl]-4,5,6,7-tetrahydro-1H-pyrazolo[3,4-c]pyridine-3-carboxamide 4

The compound 4h (344 mg, 0.68 mmol) was dissolved in methanol (6 ml). Aqueous ammonia (4 ml) was added to give a reaction mixture, which was refluxed overnight at 55° C. TLC was used to monitor the reaction progress. After the reaction was completed, the reaction mixture was purified by column chromatography to give compound 4 (203 mg, light yellow solid), yield: 62.7%.

MS m/z (ES): 478.2 [M+1]

$^1$H NMR (400 MHz, CDCl$_3$) δ 7.37-7.31 (m, 4H), 7.28-7.26 (m, 2H), 6.98 (t, J=8.6 Hz, 1H), 6.84 (br s, 1H), 5.59 (br s, 1H), 4.12 (t, J=6.7 Hz, 2H), 3.91 (s, 3H), 3.62-3.59 (m, 2H), 3.37 (t, J=6.7 Hz, 2H), 2.56 (t, J=5.8 Hz, 2H), 1.95-1.92 (m, 4H).

Example 5: Preparation of 1-(4-methoxyphenyl)-7-oxo-6-[4-(2-oxo-pyrrolidin-1-yl)phenyl]-4,5,6,7-tetrahydro-1H-pyrazolo[3,4-c]pyridine-3-carboxamide

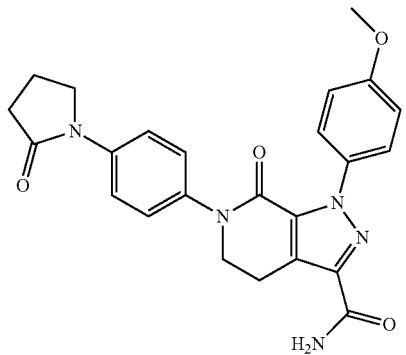 [SMILES: COc1ccc(-n2nc(C(N)=O)c3c2C(=O)N(c2ccc(N4CCCC4=O)cc2)CC3)cc1]

Preparation scheme is shown below:

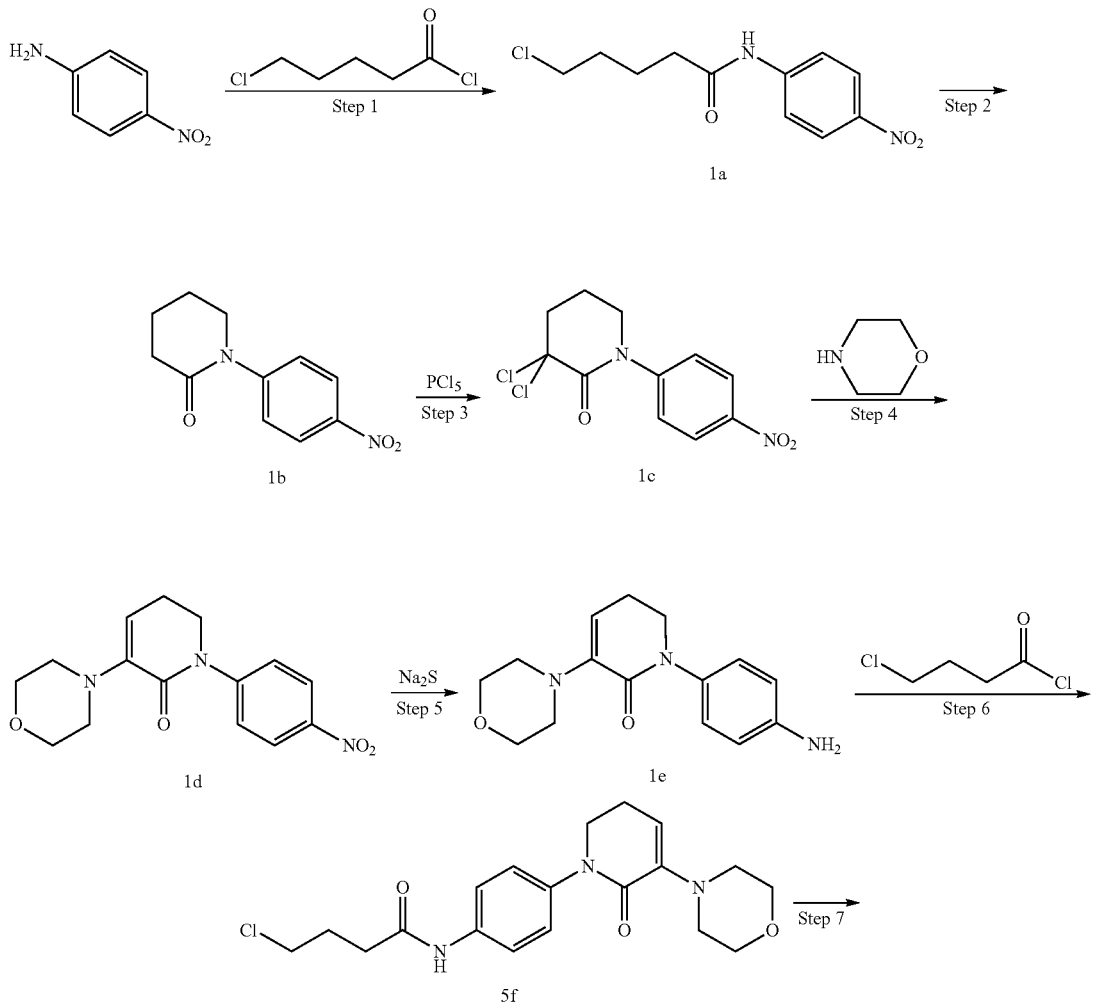

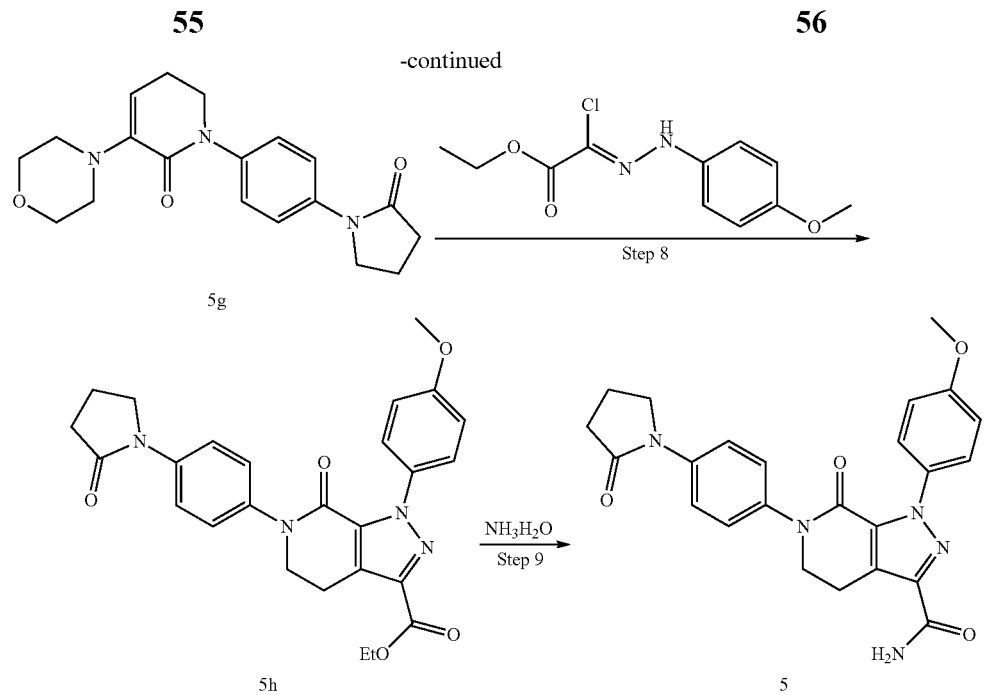

Step 1 was carried out in the same manner as the step 1 in Example 1;
Step 2 was carried out in the same manner as the step 2 in Example 1;
Step 3 was carried out in the same manner as the step 3 in Example 1;
Step 4 was carried out in the same manner as the step 4 in Example 1;
Step 5 was carried out in the same manner as the step 5 in Example 1;

Step 6: Preparation of Compound 5f

The compound 1e (1 g, 3.66 mmol) was dissolved in tetrahydrofuran (20 ml). N,N-diisopropylethylamine (0.6 g, 4.58 mmol) was added, cooled in ice bath. 4-Chlorobutyryl chloride (0.62 g, 4.40 mmol) was added dropwise to obtain a reaction mixture. The reaction mixture was reacted overnight at room temperature. TLC was used to monitor the reaction progress. After the reaction was completed, water was added into the reaction solution, which was separated and washed with water for three times, dried over anhydrous magnesium sulfate, filtered, and the solvent was distilled off under reduced pressure to give compound 5f (1.12 g, yellow solid), yield: 81.2%.
MS m/z (ES): 378.2 [M+1]

Step 7: Preparation of Compound 5 g

The compound 5f (1.12 g, 2.96 mmol) was dissolved in tetrahydrofuran (25 ml). Sodium hydride (0.18 g, 7.5 mmol) was added portion-wise under an ice bath to obtain a reaction mixture. Then the reaction mixture was reacted overnight at room temperature. TLC was used to monitor the reaction progress. After the reaction was completed, ice-water was added into the reaction solution under an ice bath to quench sodium hydride. After removing tetrahydrofuran by distillation under reduced pressure, the residue was extracted twice by dichloromethane, the combined organic phases were dried over anhydrous magnesium sulfate, filtered, and the solvent was distilled off under reduced pressure. The residue was purified by column chromatography to give compound 5 g (0.82 g, yellow solid), yield: 81.2%.
MS m/z (ES): 342.2 [M+1]

Step 8: Preparation of Compound 5h

The compound 5 g (273 mg, 0.80 mmol) was dissolved in ethyl acetate (10 ml). Ethyl [(4-methoxyphenyl)hydrazino]chloroacetate (266 mg, 1.04 mmol) and triethylamine (242 mg, 2.4 mmol) were added at room temperature to give a reaction mixture, which was refluxed overnight at 80° C. TLC was used to monitor the reaction progress. After the reaction was completed, 4N HCl (1.6 ml) was slowly added dropwise at room temperature to obtain a reaction mixture, which was reacted overnight at room temperature. TLC was used to monitor the reaction progress. After the reaction was completed, the reaction mixture was purified by column chromatography to give compound 5h (270 mg, yellow solid), yield: 71.2%.
MS m/z (ES): 475.2 [M+1]

Step 9: Preparation of 1-(4-methoxyphenyl)-7-oxo-6-[4-(2-oxo-pyrrolidin-1-yl)phenyl]-4,5,6,7-tetrahydro-1H-pyrazolo[3,4-c]pyridine-3-carboxamide 5

The compound 5h (270 mg, 0.57 mmol) was dissolved in methanol (6 ml). Aqueous ammonia (4 ml) was added to give a reaction mixture, which was refluxed overnight at 55° C. TLC was used to monitor the reaction progress. After the reaction was completed, the reaction mixture was purified by column chromatography to give 5 (180 mg, light yellow solid), yield: 71.0%.
MS m/z (ES): 446.2 [M+1]
$^1$H NMR (400 MHz, CDCl$_3$) δ 7.62 (d, J=8.9 Hz, 2H), 7.47 (d, J=9.0 Hz, 2H), 7.31 (d, J=8.9 Hz, 2H), 6.93 (d, J=9.0 Hz, 2H), 6.87 (br s, 1H), 5.62 (br s, 1H), 4.09 (t, J=6.7 Hz, 2H), 3.85-3.82 (m, 5H), 3.37 (t, J=6.7 Hz, 2H), 2.61 (t, J=8.1 Hz, 2H), 2.20-2.14 (m, 2H).

Example 6: Preparation of 1-(2-fluorophenyl)-7-oxo-6-[4-(2-oxo-pyrrolidin-1-yl)phenyl]-4,5,6,7-tetrahydro-1H-pyrazolo[3,4-c]pyridine-3-carboxamide
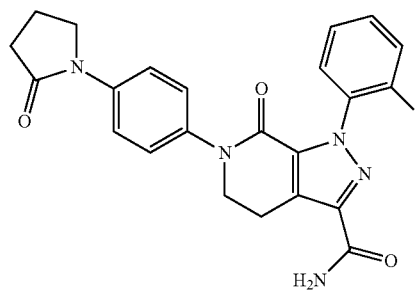
Preparation scheme is shown below:
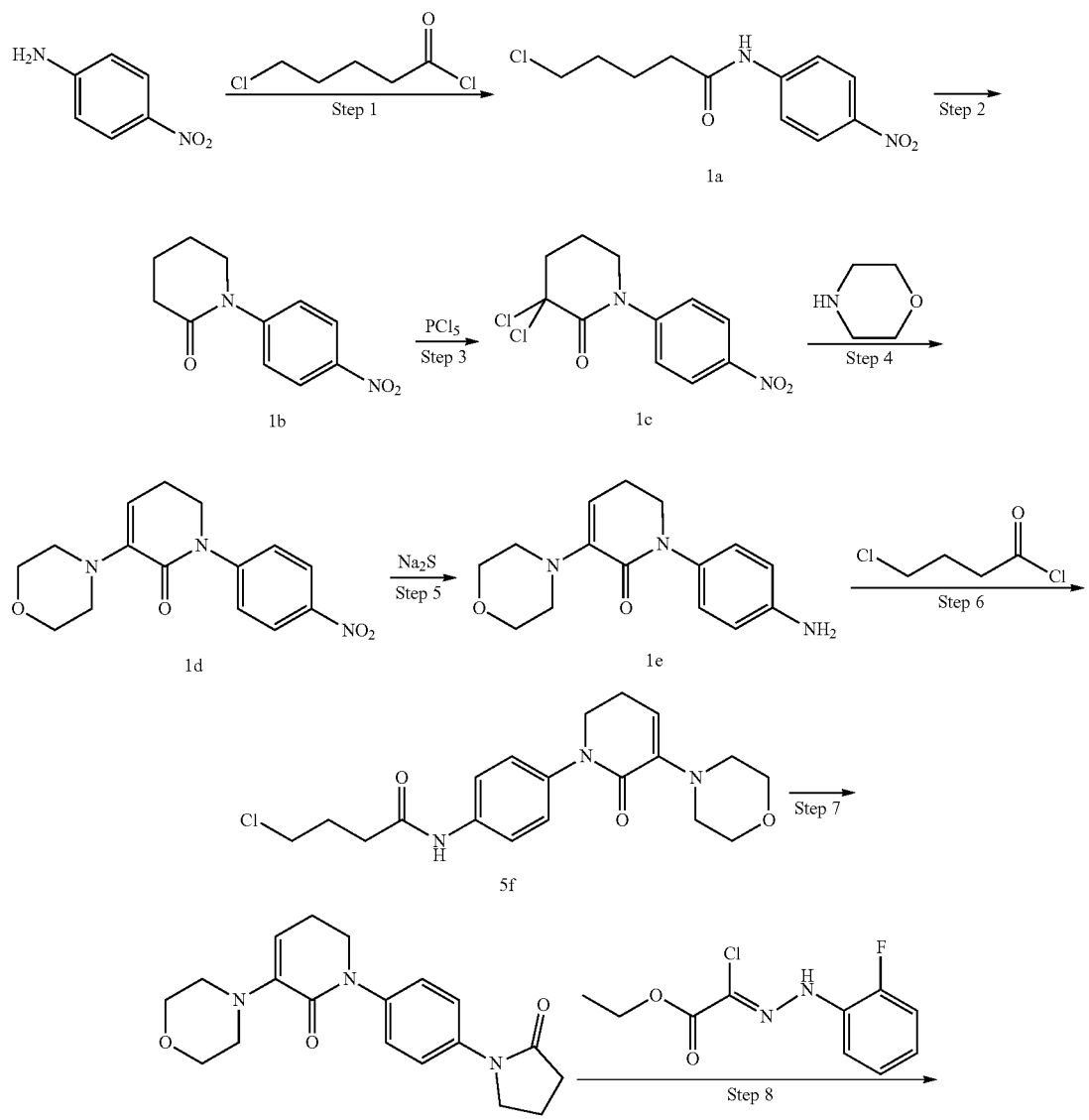

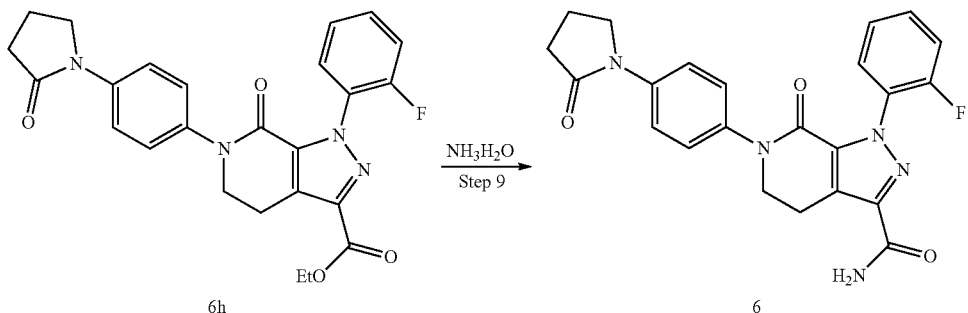

Step 1 was carried out in the same manner as the step 1 in Example 1;
Step 2 was carried out in the same manner as the step 2 in Example 1;
Step 3 was carried out in the same manner as the step 3 in Example 1;
Step 4 was carried out in the same manner as the step 4 in Example 1;
Step 5 was carried out in the same manner as the step 5 in Example 1;
Step 6 was carried out in the same manner as the step 6 in Example 5;
Step 7 was carried out in the same manner as the step 7 in Example 5;

Step 8: Preparation of Compound 6h

The compound 5 g (273 mg, 0.80 mmol) was dissolved in ethyl acetate (10 ml). Ethyl [(2-fluorophenyl)hydrazino] chloroacetate (254 mg, 1.04 mmol) and triethylamine (242 mg, 2.4 mmol) were added at room temperature to give a reaction mixture, which was refluxed overnight at 80° C. TLC was used to monitor the reaction progress. After the reaction was completed, 4N HCl (1.6 ml) was slowly added dropwise at room temperature to obtain a reaction mixture, which was reacted overnight at room temperature. TLC was used to monitor the reaction progress. After the reaction was completed, the reaction mixture was purified by column chromatography to give compound 6h (260 mg, yellow solid), yield: 70.3%.

MS m/z (ES): 463.2 [M+1]

Step 9: Preparation of 1-(2-fluorophenyl)-7-oxo-6-[4-(2-oxo-pyrrolidin-1-yl)phenyl]-4,5,6,7-tetrahydro-1H-pyrazolo[3,4-c]pyridine-3-carboxamide 6

The compound 6h (260 mg, 0.56 mmol) was dissolved in methanol (6 ml). Aqueous ammonia (4 ml) was added to give a reaction mixture, which was refluxed overnight at 55° C. TLC was used to monitor the reaction progress. After the reaction was completed, the reaction mixture was purified by column chromatography to give compound 6 (146 mg, light yellow solid), yield: 60.2%.

MS m/z (ES): 434.2 [M+1]

$^1$H NMR (400 MHz, CDCl$_3$) δ 7.63-7.59 (m, 2H), 7.51 (td, J=7.7, 1.6 Hz, 1H), 7.46-7.40 (m, 1H), 7.33-7.29 (m, 2H), 7.25-7.17 (m, 2H), 6.84 (br s, 1H), 5.60 (br s, 1H), 4.11 (t, J=6.7 Hz, 2H), 3.83 (t, J=7.0 Hz, 2H), 3.38 (t, J=6.7 Hz, 2H), 2.61 (t, J=8.1 Hz, 2H), 2.20-2.12 (m, 2H).

Example 7: Preparation of 1-(3-fluoro-4-methoxyphenyl)-7-oxo-6-[4-(2-oxo-pyrrolidin-1-yl)phenyl]-4,5,6,7-tetrahydro-1H-pyrazolo[3,4-c]pyridine-3-carboxamide

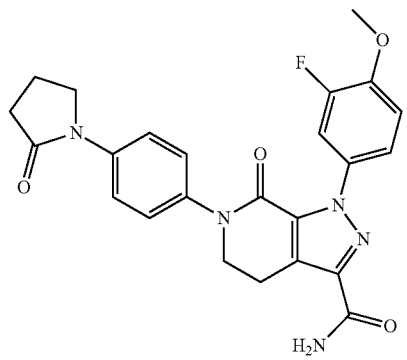 [SMILES: COc1ccc(-n2nc(C(N)=O)c3c2C(=O)N(c2ccc(N4CCCC4=O)cc2)CC3)cc1F]

Preparation scheme is shown below:

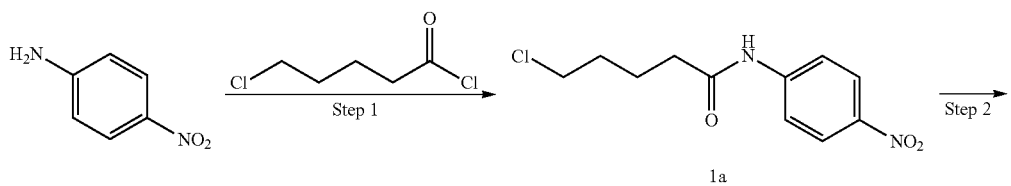

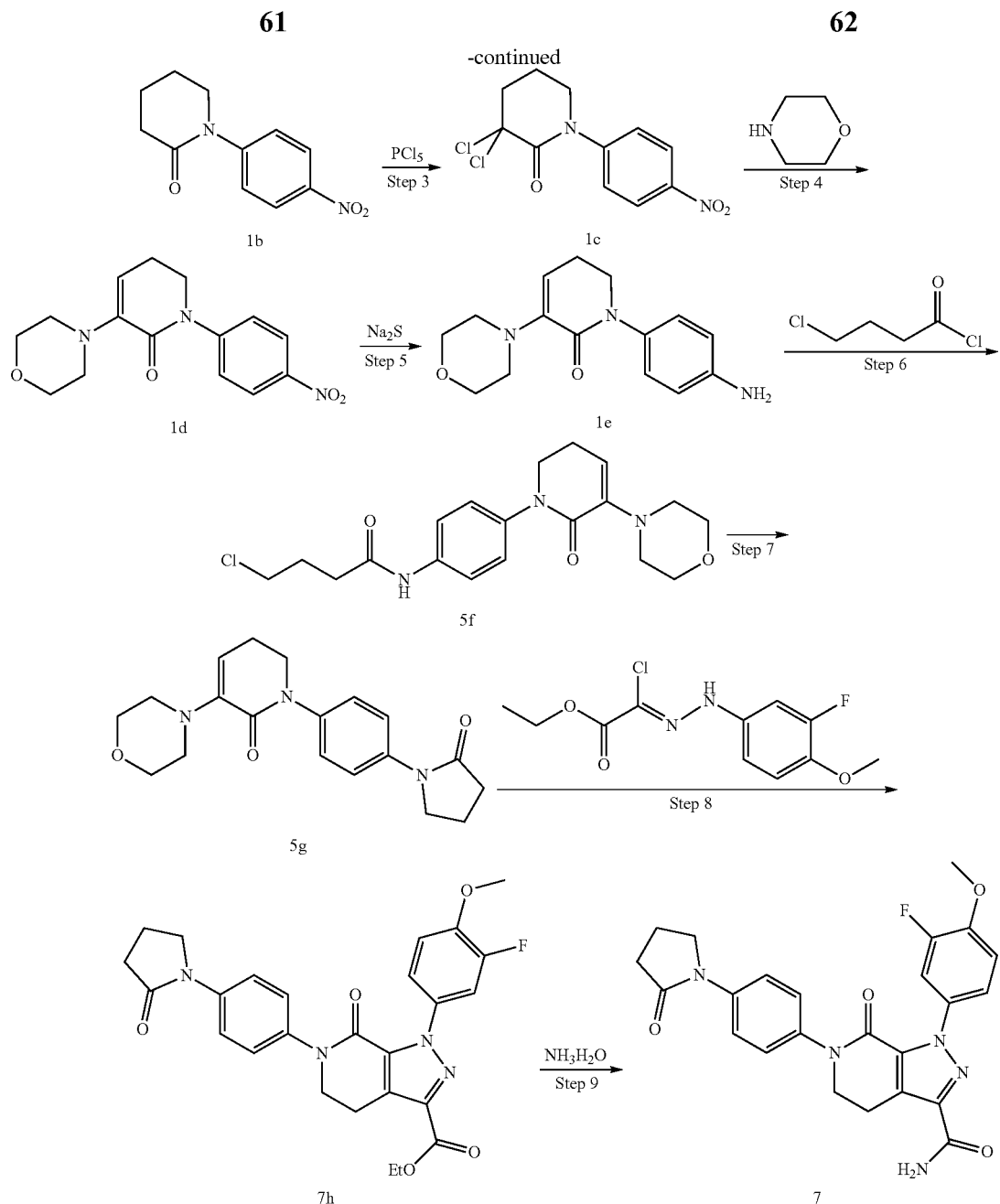

Step 1 was carried out in the same manner as the step 1 in Example 1;

Step 2 was carried out in the same manner as the step 2 in Example 1;

Step 3 was carried out in the same manner as the step 3 in Example 1;

Step 4 was carried out in the same manner as the step 4 in Example 1;

Step 5 was carried out in the same manner as the step 5 in Example 1;

Step 6 was carried out in the same manner as the step 6 in Example 5;

Step 7 was carried out in the same manner as the step 7 in Example 5;

Step 8: Preparation of Compound 7h

The compound 5 g (273 mg, 0.80 mmol) was dissolved in ethyl acetate (10 ml). Ethyl [(3-fluoro-4-methoxyphenyl)hydrazino]chloroacetate (286 mg, 1.04 mmol) and triethylamine (242 mg, 2.4 mmol) were added at room temperature to give a reaction mixture, which was refluxed overnight at 80° C. TLC was used to monitor the reaction progress. After the reaction was completed, 4N HCl (1.6 ml) was slowly added dropwise at room temperature to obtain a reaction mixture, which was reacted overnight at room temperature. TLC was used to monitor the reaction progress. After the reaction was completed, the reaction mixture was purified by column chromatography to give compound 7h (329 mg, yellow solid), yield: 83.5%.

MS m/z (ES): 493.2 [M+1]

Step 9: Preparation of 1-(3-fluoro-4-methoxyphenyl)-7-oxo-6-[4-(2-oxo-pyrrolidin-1-yl)phenyl]-4,5,6,7-tetrahydro-1H-pyrazolo[3,4-c]pyridine-3-carboxamide 7

The compound 7h (329 mg, 0.67 mmol) was dissolved in methanol (6 ml). Aqueous ammonia (4 ml) was added to give a reaction mixture, which was refluxed overnight at 55° C. TLC was used to monitor the reaction progress. After the reaction was completed, the reaction mixture was purified by column chromatography to give compound 7 (202 mg, light yellow solid), yield: 65.2%.

MS m/z (ES): 464.2 [M+1]

$^1$H NMR (400 MHz, CDCl$_3$) δ 7.65-7.61 (m, 2H), 7.37-7.30 (m, 4H), 6.98 (t, J=8.8 Hz, 1H), 6.85 (br s, 1H), 5.62 (br s, 1H), 4.09 (t, J=6.7 Hz, 2H), 3.91 (s, 3H), 3.84 (t, J=7.0 Hz, 2H), 3.38 (t, J=6.7 Hz, 2H), 2.61 (t, J=8.1 Hz, 2H), 2.20-2.13 (m, 2H).

Example 8: Preparation of 1-(3,5-difluoro-phenyl)-7-oxo-6-[4-(2-oxo-pyrrolidin-1-yl)phenyl]-4,5,6,7-tetrahydro-1H-pyrazolo[3,4-c]pyridine-3-carboxamide

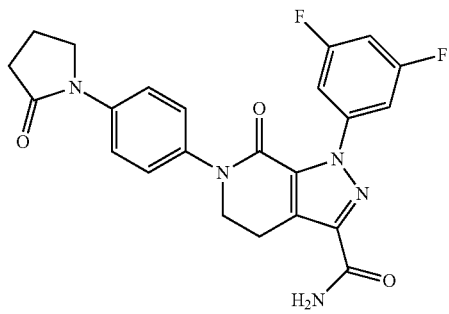 [SMILES: NC(=O)c1nn(-c2cc(F)cc(F)c2)c2c1CCN(c1ccc(N3CCCC3=O)cc1)C2=O]

Preparation scheme is shown below:

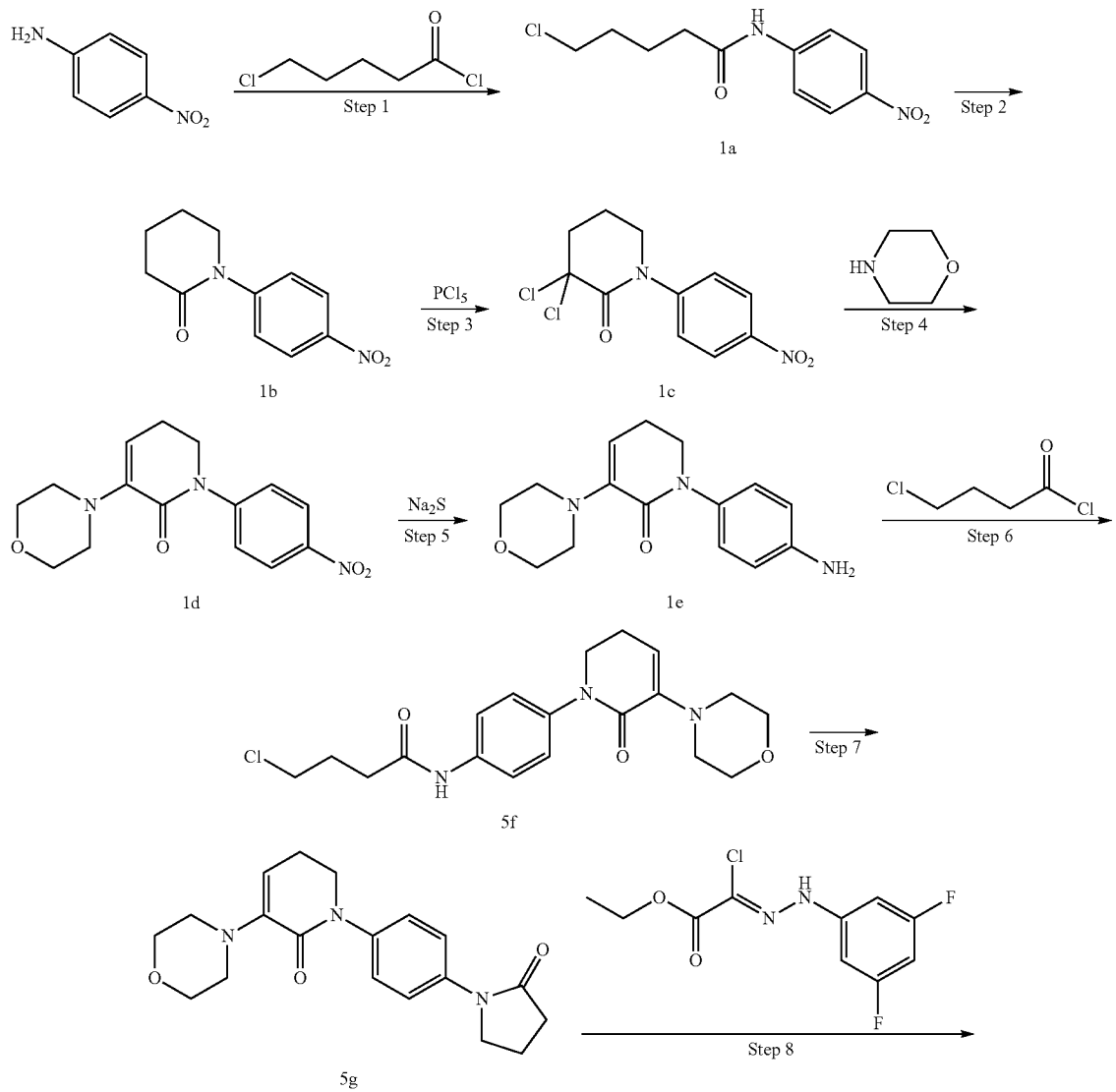

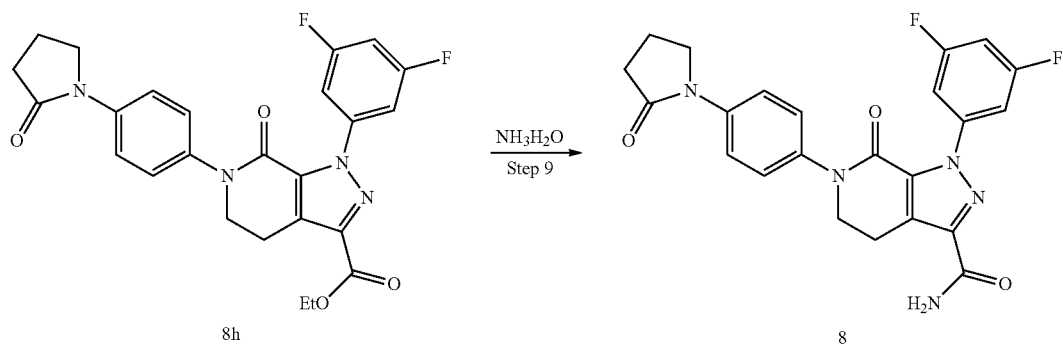

Step 1 was carried out in the same manner as the step 1 in Example 1;
Step 2 was carried out in the same manner as the step 2 in Example 1;
Step 3 was carried out in the same manner as the step 3 in Example 1;
Step 4 was carried out in the same manner as the step 4 in Example 1;
Step 5 was carried out in the same manner as the step 5 in Example 1;
Step 6 was carried out in the same manner as the step 6 in Example 5;
Step 7 was carried out in the same manner as the step 7 in Example 5;

Step 8: Preparation of Compound 8h

The compound 5 g (273 mg, 0.80 mmol) was dissolved in ethyl acetate (10 ml). Ethyl [(3,5-difluoro-phenyl)hydrazino]chloroacetate (273 mg, 1.04 mmol) and triethylamine (242 mg, 2.4 mmol) were added at room temperature to give a reaction mixture, which was refluxed overnight at 80° C. TLC was used to monitor the reaction progress. After the reaction was completed, 4N HCl (1.6 ml) was slowly added dropwise at room temperature to obtain a reaction mixture, which was reacted overnight at room temperature. TLC was used to monitor the reaction progress. After the reaction was completed, the reaction mixture was purified by column chromatography to give compound 8h (305 mg, yellow solid), yield: 79.4%.

MS m/z (ES): 481.2 [M+1]

Step 9: Preparation of 1-(3,5-difluoro-phenyl)-7-oxo-6-[4-(2-oxo-pyrrolidin-1-yl)phenyl]-4,5,6,7-tetrahydro-1H-pyrazolo[3,4-c]pyridine-3-carboxamide 8

The compound 8h (305 mg, 0.63 mmol) was dissolved in methanol (6 ml). Aqueous ammonia (4 ml) was added to give a reaction mixture, which was refluxed overnight at 55° C. TLC was used to monitor the reaction progress. After the reaction was completed, the reaction mixture was purified by column chromatography to give compound 8 (187 mg, light yellow solid), yield: 65.2%.

MS m/z (ES): 452.1 [M+1]

$^1$H NMR (400 MHz, CDCl$_3$) δ 7.67-7.64 (m, 2H), 7.34-7.30 (m, 2H), 7.24-7.20 (m, 2H), 6.90-6.84 (m, 2H), 5.63 (br s, 1H), 4.10 (t, J=6.7 Hz, 2H), 3.86 (t, J=7.0 Hz, 2H), 3.38 (t, J=6.7 Hz, 2H), 2.62 (t, J=8.1 Hz, 2H), 2.21-2.13 (m, 2H).

Example 9: Preparation of 1-(4-methoxyphenyl)-7-oxo-6-[2-methyl-4-(2-oxo-pyrrolidin-1-yl)phenyl]-4,5,6,7-tetrahydro-1H-pyrazolo[3,4-c]pyridine-3-carboxamide

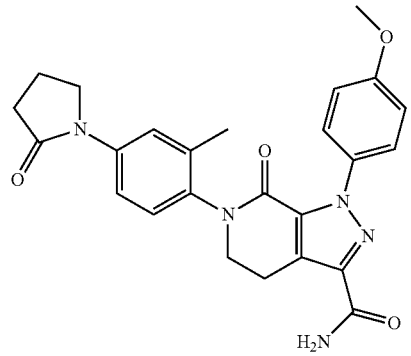 [SMILES: COc1ccc(-n2nc(C(N)=O)c3c2C(=O)N(c2ccc(N4CCCC4=O)cc2C)CC3)cc1]

Preparation scheme is shown below:

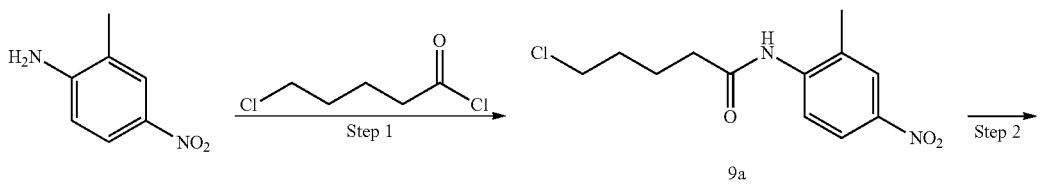

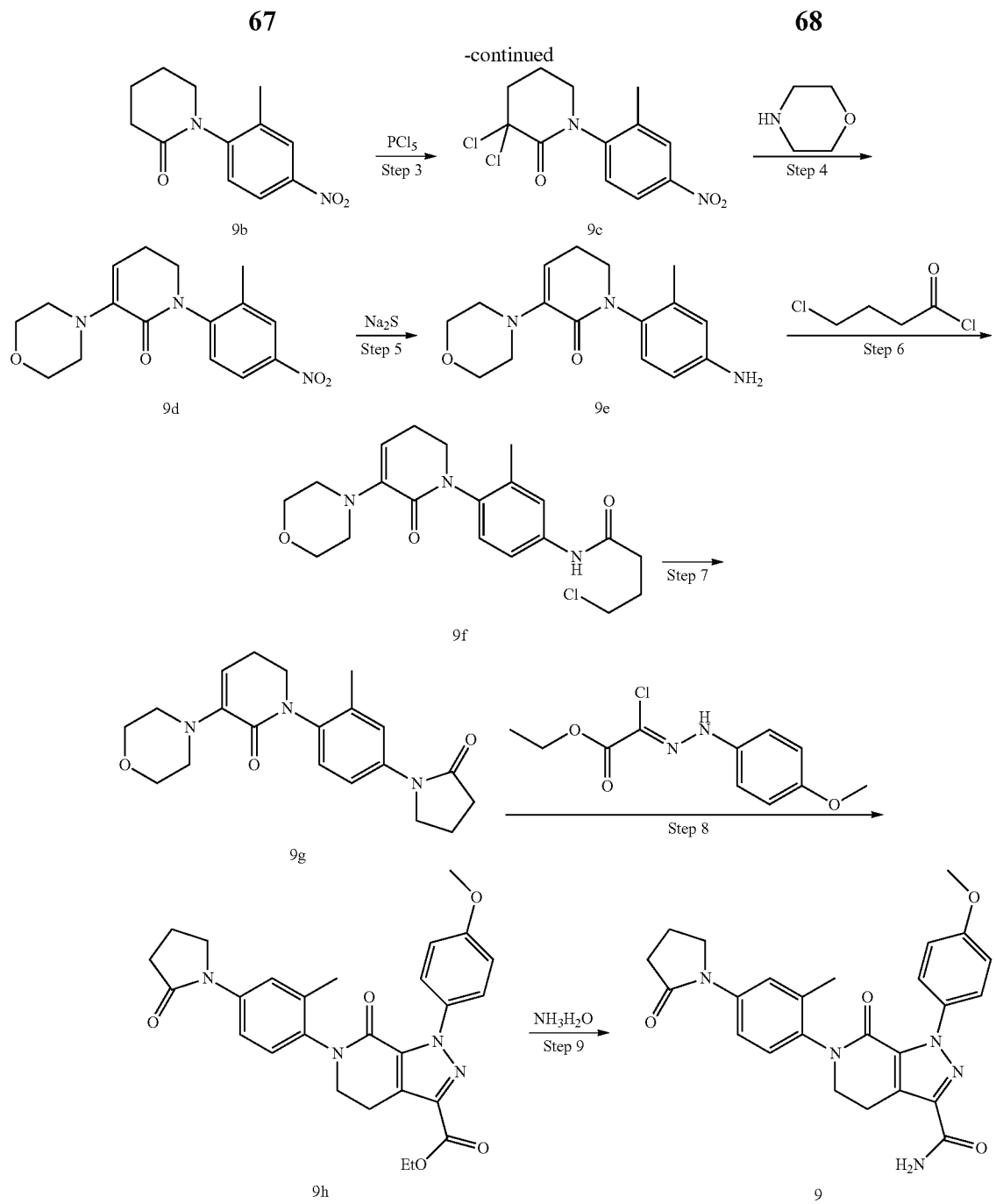

Step 1: Preparation of Compound 9a

The 2-methyl-4-nitroaniline (3 g, 19.7 mmol) was dissolved in dichloromethane (60 ml), N,N-diisopropylethylamine (6.4 g, 49.5 mmol) was added, cooled in ice bath to 5° C. or lower. 5-chlorovaleryl chloride (3.7 g, 23.9 mmol) was added dropwise to obtain a reaction mixture. The reaction mixture was reacted overnight at room temperature. TLC was used to monitor the reaction progress. After the reaction was completed, water was poured into the reaction solution, then the reaction solution was separated and washed with water for three times, dried over anhydrous magnesium sulfate, filtered, and the solvent was distilled off under reduced pressure to give compound 9a (4.2 g, yellow solid), yield: 78.8%.

MS m/z (ES): 271.1 [M+1]

Step 2: Preparation of Compound 9b

The compound 9a (4.2 g, 15.5 mmol) was dissolved in tetrahydrofuran (80 ml). Sodium hydride (0.75 g, 31.3 mmol) was added portion-wise under an ice bath to obtain a reaction mixture. Then the reaction mixture was reacted overnight at room temperature. TLC was used to monitor the reaction progress. After the reaction was completed, ice-water was added into the reaction solution under an ice bath to quench sodium hydride. After removing tetrahydrofuran by distillation under reduced pressure, the residue was extracted twice by ethyl acetate, dried over anhydrous magnesium sulfate, filtered, and the solvent was distilled off under reduced pressure. The residue was purified by column chromatography to give compound 9b (3.27 g, yellow solid), yield: 90.1%.

MS m/z (ES): 235.1 [M+1]

Step 3: Preparation of Compound 9c

The compound 9b (3.27 g, 14.0 mmol) was dissolved in dichloromethane (100 ml). Phosphorus pentachloride (8.7 g, 41.8 mmol) was added portion-wise under an ice bath to obtain a reaction mixture. The reaction mixture was refluxed at 40° C. When the reaction solution generated little bubble, TLC was used to monitor the reaction progress. After the reaction was completed, ice-water was added into the reaction mixture under an ice bath to quench phosphorus pentachloride. The reaction solution was separated, washed with water for three times, dried over anhydrous magnesium sulfate, filtered, and the solvent was removed by distillation under reduced pressure to give compound 9c (4 g, yellow solid), yield: 94.6%.

MS m/z (ES): 303.0, 305.0 [M+1]

Step 4: Preparation of Compound 9d

The compound 9c (4 g, 13.2 mmol) was dissolved in morpholine (40 ml) to obtain a reaction mixture, which was refluxed at 120° C. for 2 hours, TLC was used to monitor the reaction progress. After the reaction was completed, ethyl acetate was added, the obtained solution was washed with water for three times, dried over anhydrous magnesium sulfate, filtered, and the solvent was removed by distillation under reduced pressure to give compound 9d (3.98 g, black solid), yield: 95.0%.

MS m/z (ES): 318.1 [M+1]

Step 5: Preparation of Compound 9e

The compound 9d (3.98 g, 12.5 mmol) was dissolved in ethanol (50 ml). Sodium sulfide nonahydrate (9 g, 37.5 mmol) was added, and then water (20 ml) was added to obtain a reaction mixture, which was refluxed overnight at 50° C. TLC was used to monitor the reaction progress. After the reaction was completed, ethanol was removed by distillation under reduced pressure, the residue was extracted by ethyl acetate for three times, the combined organic phases were dried over anhydrous magnesium sulfate, filtered, and the solvent was removed by distillation under reduced pressure to give compound 9e (3.2 g, yellow solid) yield: 88.9%.

MS m/z (ES): 288.2 [M+1]

Step 6: Preparation of Compound 9f

The compound 9e (3.2 g, 11.1 mmol) was dissolved in dichloromethane (50 ml), N,N-diisopropylethylamine (3.6 g, 27.9 mmol) was added, cooled in ice bath. 4-Chlorobutyryl chloride (2.4 g, 17.0 mmol) was added dropwise to obtain a reaction mixture. The reaction mixture was reacted overnight at room temperature. TLC was used to monitor the reaction progress. After the reaction was completed, water was added into the reaction solution, which was separated and washed with water for three times, dried over anhydrous magnesium sulfate, filtered, and the solvent was distilled off under reduced pressure to give compound 9f (3.5 g, yellow solid), yield: 80.3%.

MS m/z (ES): 392.2 [M+1]

Step 7: Preparation of Compound 9 g

The compound 9f (3.5 g, 8.9 mmol) was dissolved in tetrahydrofuran (50 ml). Sodium hydride (0.6 g, 25 mmol) was added portion-wise under an ice bath to obtain a reaction mixture. Then the reaction mixture was reacted overnight at room temperature. TLC was used to monitor the reaction progress. After the reaction was completed, ice-water was added into the reaction solution to quench sodium hydride. After removing tetrahydrofuran by distillation under reduced pressure, the residue was extracted twice by dichloromethane, the combined organic phases were dried over anhydrous magnesium sulfate, filtered, and the solvent was distilled off under reduced pressure. The residue was purified by column chromatography to give compound 9 g (2.59 g, yellow solid), yield: 81.7%.

MS m/z (ES): 356.2 [M+1]

Step 8: Preparation of Compound 9h

The compound 9 g (280 mg, 0.79 mmol) was dissolved in toluene (10 ml). Ethyl [(4-methoxyphenyl)hydrazino]chloroacetate (214 mg, 0.83 mmol) and triethylamine (252 mg, 2.5 mmol) were added at room temperature to give a reaction mixture, which was refluxed overnight at 120° C. TLC was used to monitor the reaction progress. After the reaction was completed, toluene was removed by distillation under reduced pressure. The residue was dissolved by dichloromethane (20 ml). Trifluoroacetic acid (2 ml) was added at room temperature to obtain a reaction mixture, which was reacted overnight at room temperature. TLC was used to monitor the reaction progress. After the reaction was completed, the reaction mixture was purified by column chromatography to give compound 9h (300 mg, yellow solid), yield: 77.9%.

MS m/z (ES): 489.2 [M+1]

Step 9: Preparation of 1-(4-methoxyphenyl)-7-oxo-6-[2-methyl-4-(2-oxo-pyrrolidin-1-yl)phenyl]-4,5,6,7-tetrahydro-1H-pyrazolo[3,4-c]pyridine-3-carboxamide 9

The compound 9h (300 mg, 0.61 mmol) was dissolved in methanol (4 ml). Aqueous ammonia (2 ml) was added to give a reaction mixture, which was refluxed overnight at 70° C. TLC was used to monitor the reaction progress. After the reaction was completed, the reaction mixture was purified by column chromatography to give compound 9 (208 mg, light yellow solid), yield: 73.8%.

MS m/z (ES): 460.2 [M+1]

$^1$H NMR (400 MHz, CDCl$_3$) δ 7.51-7.46 (m, 4H), 7.17 (d, J=8.5 Hz, 1H), 6.93 (d, J=8.8 Hz, 2H), 6.87 (br s, 1H), 5.54 (br s, 1H), 4.09-4.02 (m, 1H), 3.84-3.79 (m, 6H), 3.45-3.32 (m, 2H), 2.60 (t, J=8.0 Hz, 2H), 2.26 (s, 3H), 2.19-2.13 (m, 2H).

Example 10: Preparation of 1-(2-methoxyphenyl)-7-oxo-6-[2-methyl-4-(2-oxo-pyrrolidin-1-yl)phenyl]-4,5,6,7-tetrahydro-1H-pyrazolo[3,4-c]pyridine-3-carboxamide

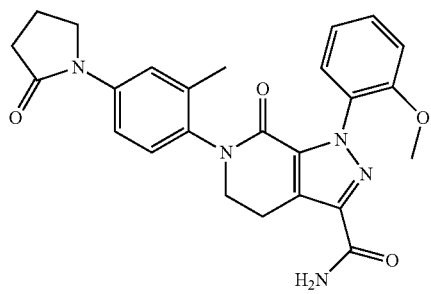 [SMILES: COc1ccccc1-n1nc(C(N)=O)c2c1C(=O)N(c1ccc(N3CCCC3=O)cc1C)CC2]

Preparation scheme is shown below:

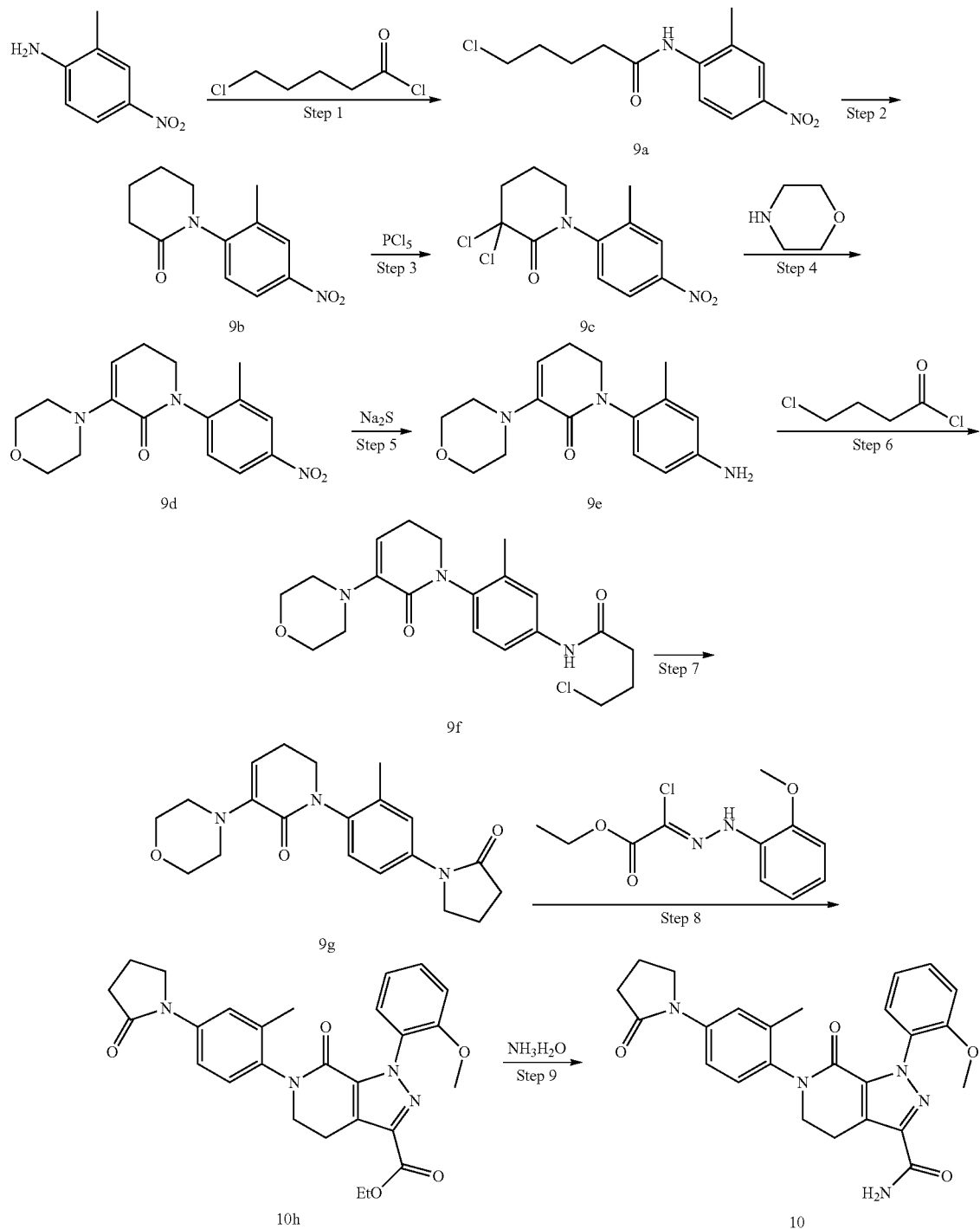

Step 1 was carried out in the same manner as the step 1 in Example 9;

Step 2 was carried out in the same manner as the step 2 in Example 9;

Step 3 was carried out in the same manner as the step 3 in Example 9;

Step 4 was carried out in the same manner as the step 4 in Example 9;

Step 5 was carried out in the same manner as the step 5 in Example 9;

Step 6 was carried out in the same manner as the step 6 in Example 9;

Step 7 was carried out in the same manner as the step 7 in Example 9;

Step 8: Preparation of Compound 10h

The compound 9 g (566 mg, 1.6 mmol) was dissolved in toluene (20 ml). Ethyl [(2-methoxyphenyl)hydrazino]chloroacetate (490 mg, 1.9 mmol) and triethylamine (483 mg, 4.78 mmol) were added at room temperature to give a reaction mixture, which was refluxed overnight at 120° C. TLC was used to monitor the reaction progress. After the reaction was completed, toluene was removed by distillation under reduced pressure. The residue was dissolved by dichloromethane (40 ml). Trifluoroacetic acid (4 ml) was added at room temperature to obtain a reaction mixture, which was reacted overnight at room temperature. TLC was used to monitor the reaction progress. After the reaction was completed, the reaction mixture was purified by column chromatography to give compound 10h (622 mg, yellow solid), yield: 80.0%.

MS m/z (ES): 489.2 [M+1]

Step 9: Preparation of 1-(2-methoxyphenyl)-7-oxo-6-[2-methyl-4-(2-oxo-pyrrolidin-1-yl)phenyl]-4,5,6,7-tetrahydro-1H-pyrazolo[3,4-c]pyridine-3-carboxamide 10

The compound 10h (622 mg, 1.27 mmol) was dissolved in methanol (8 ml). Aqueous ammonia (5 ml) was added to give a reaction mixture, which was refluxed overnight at 70° C. TLC was used to monitor the reaction progress. After the reaction was completed, the reaction mixture was purified by column chromatography to give compound 10 (410 mg, light yellow solid), yield: 70.1%.

MS m/z (ES): 460.2 [M+1]

$^1$H NMR (400 MHz, CDCl$_3$) δ 7.48-7.44 (m, 2H), 7.41-7.37 (m, 2H), 7.14 (d, J=8.6 Hz, 1H), 7.03 (t, J=7.6 Hz, 1H), 6.98 (d, J=8.6 Hz, 1H), 6.86 (br s, 1H), 5.54 (br s, 1H), 4.01-3.79 (m, 7H), 3.43-3.36 (m, 2H), 2.60 (t, J=8.1 Hz, 2H), 2.25 (s, 3H), 2.18-2.11 (m, 2H).

Example 11: Preparation of 1-(4-methylphenyl)-7-oxo-6-[2-methyl-4-(2-oxo-pyrrolidin-1-yl)phenyl]-4,5,6,7-tetrahydro-1H-pyrazolo[3,4-c]pyridine-3-carboxamide

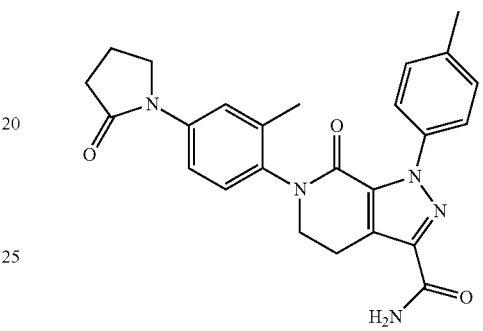

Preparation scheme is shown below:

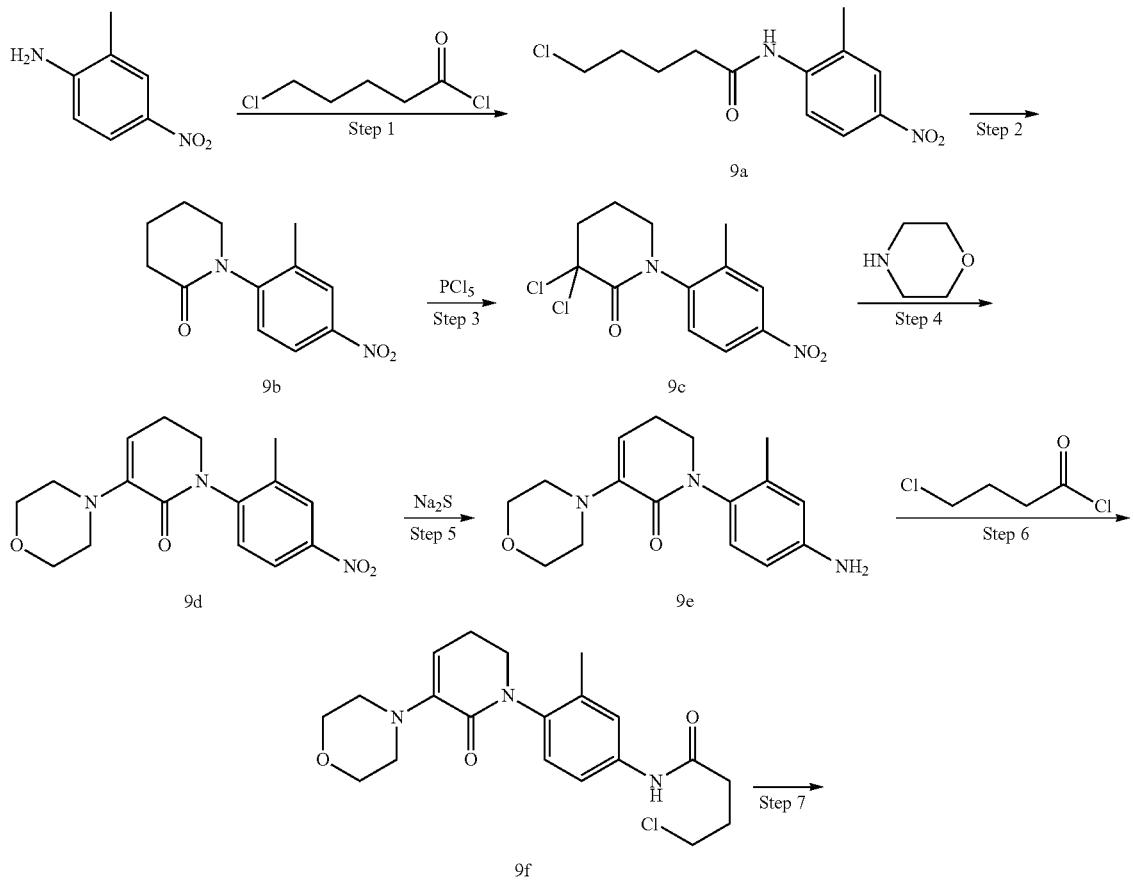

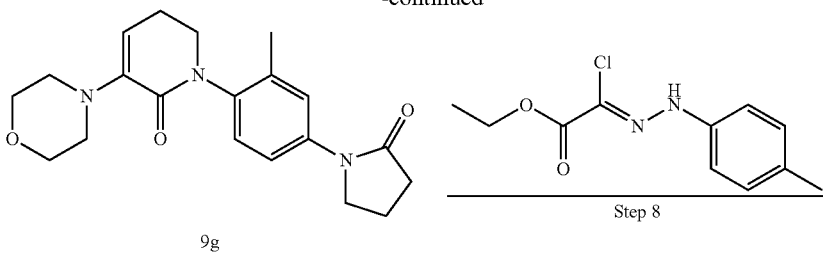

9g

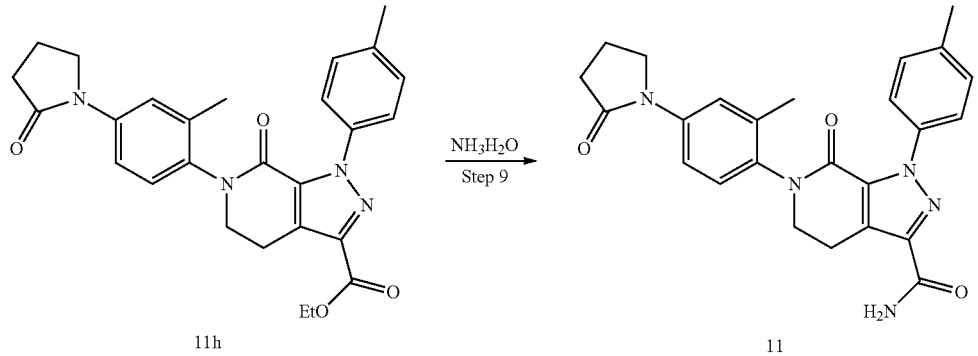

11h → 11

Step 1 was carried out in the same manner as the step 1 in Example 9;
Step 2 was carried out in the same manner as the step 2 in Example 9;
Step 3 was carried out in the same manner as the step 3 in Example 9;
Step 4 was carried out in the same manner as the step 4 in Example 9;
Step 5 was carried out in the same manner as the step 5 in Example 9;
Step 6 was carried out in the same manner as the step 6 in Example 9;
Step 7 was carried out in the same manner as the step 7 in Example 9;

Step 8: Preparation of Compound 11h

The compound 9 g (344 mg, 0.97 mmol) was dissolved in toluene (20 ml). Ethyl [(4-methylphenyl)hydrazino]chloroacetate (280 mg, 1.16 mmol) and triethylamine (300 mg, 2.97 mmol) were added at room temperature to give a reaction mixture, which was refluxed overnight at 120° C. TLC was used to monitor the reaction progress. After the reaction was completed, toluene was removed by distillation under reduced pressure. The residue was dissolved by dichloromethane (20 ml), then the trifluoroacetic acid (1.5 ml) was added at room temperature to obtain a reaction mixture, which was reacted overnight at room temperature. TLC was used to monitor the reaction progress. After the reaction was completed, the reaction mixture was purified by column chromatography to give compound 11h (348 mg, yellow solid), yield: 76.1%.

MS m/z (ES): 473.2 [M+1]

Step 9: Preparation of 1-(4-methylphenyl)-7-oxo-6-[2-methyl-4-(2-oxo-pyrrolidin-1-yl)phenyl]-4,5,6,7-tetrahydro-1H-pyrazolo[3,4-c]pyridine-3-carboxamide 11

The compound 11h (348 mg, 0.74 mmol) was dissolved in methanol (5 ml). Aqueous ammonia (4 ml) was added to give a reaction mixture, which was refluxed overnight at 70° C. TLC was used to monitor the reaction progress. After the reaction was completed, the reaction mixture was purified by column chromatography to give compound 11 (238 mg, light yellow solid), yield: 72.8%.

MS m/z (ES): 444.2 [M+1]

$^1$H NMR (400 MHz, CDCl$_3$) δ 7.49-7.45 (m, 4H), 7.22 (d, J=8.1 Hz, 2H), 7.17 (d, J=8.5 Hz, 1H), 6.88 (br s, 1H), 5.58 (br s, 1H), 4.09-4.02 (m, 1H), 3.84-3.78 (m, 3H), 3.47-3.32 (m, 2H), 2.60 (t, J=8.1 Hz, 2H), 2.37 (s, 3H), 2.25 (s, 3H), 2.19-2.13 (m, 2H).

Example 12: Preparation of 1-(4-fluorophenyl)-7-oxo-6-[2-methyl-4-(2-oxo-pyrrolidin-1-yl)phenyl]-4,5,6,7-tetrahydro-1H-pyrazolo[3,4-c]pyridine-3-carboxamide

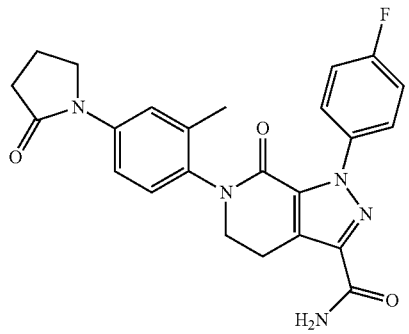 [SMILES: Cc1cc(N2CCCC2=O)ccc1N1CCc2c(C(N)=O)nn(-c3ccc(F)cc3)c2C1=O]

Preparation scheme is shown below:

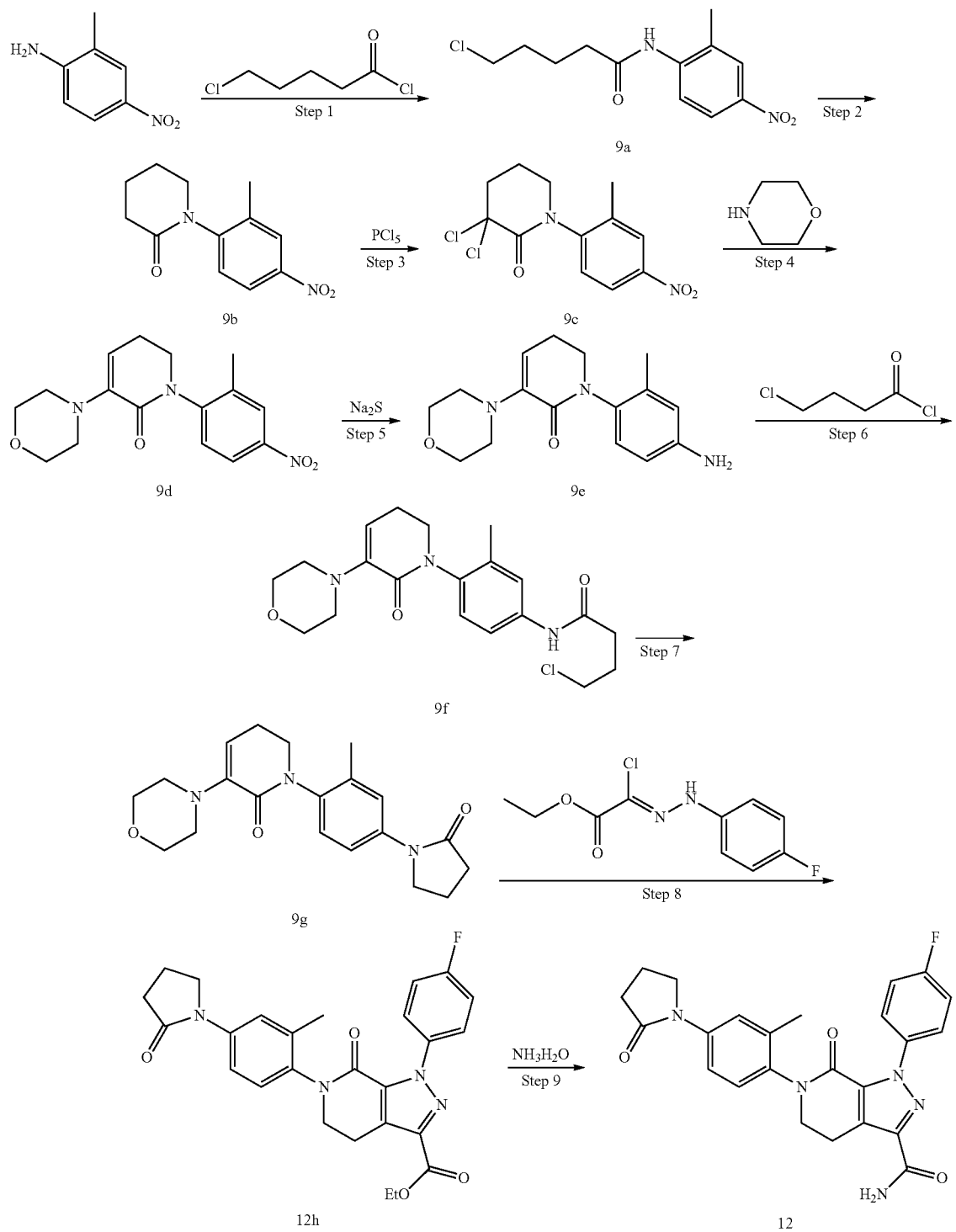

Step 1 was carried out in the same manner as the step 1 in Example 9;

Step 2 was carried out in the same manner as the step 2 in Example 9;

Step 3 was carried out in the same manner as the step 3 in Example 9;

Step 4 was carried out in the same manner as the step 4 in Example 9;

Step 5 was carried out in the same manner as the step 5 in Example 9;

Step 6 was carried out in the same manner as the step 6 in Example 9;

Step 7 was carried out in the same manner as the step 7 in Example 9;

Step 8: Preparation of Compound 12h

The compound 9 g (344 mg, 0.97 mmol) was dissolved in toluene (20 ml). Ethyl [(4-fluorophenyl)hydrazino]chloroacetate (280 mg, 1.14 mmol) and triethylamine (300 mg, 2.97 mmol) were added at room temperature to give a reaction mixture, which was refluxed overnight at 120° C. TLC was used to monitor the reaction progress. After the reaction was completed, toluene was removed by distillation under reduced pressure. The residue was dissolved by dichloromethane (20 ml). Trifluoroacetic acid (1.5 ml) was added at room temperature to obtain a reaction mixture, which was reacted overnight at room temperature. TLC was used to monitor the reaction progress. After the reaction was completed, the reaction mixture was purified by column chromatography to give compound 12h (400 mg, yellow solid), yield: 86.7%.

MS m/z (ES): 477.2 [M+1]

Step 9: Preparation of 1-(4-fluorophenyl)-7-oxo-6-[2-methyl-4-(2-oxo-pyrrolidin-1-yl)phenyl]-4,5,6,7-tetrahydro-1H-pyrazolo[3,4-c]pyridine-3-carboxamide 12

The compound 12h (400 mg, 0.84 mmol) was dissolved in methanol (5 ml). Aqueous ammonia (3 ml) was added to give a reaction mixture, which was refluxed overnight at 70° C. TLC was used to monitor the reaction progress. After the reaction was completed, the reaction mixture was purified by column chromatography to give compound 12 (244 mg, light yellow solid), yield: 64.9%.

MS m/z (ES): 448.2 [M+1]

$^1$H NMR (400 MHz, CDCl$_3$) δ 7.60-7.57 (m, 2H), 7.51-7.48 (m, 2H), 7.17 (d, J=8.5 Hz, 1H), 7.11 (t, J=8.6 Hz, 2H), 6.85 (br s, 1H), 5.58 (br s, 1H), 4.10-4.03 (m, 1H), 3.85-3.79 (m, 3H), 3.48-3.32 (m, 2H), 2.61 (t, J=8.1 Hz, 2H), 2.26 (s, 3H), 2.19-2.12 (m, 2H).

Example 13: Preparation of 1-(2,4-dimethyl-phenyl)-7-oxo-6-[2-methyl-4-(2-oxo-pyrrolidin-1-yl)phenyl]-4,5,6,7-tetrahydro-1H-pyrazolo[3,4-c]pyridine-3-carb oxamide

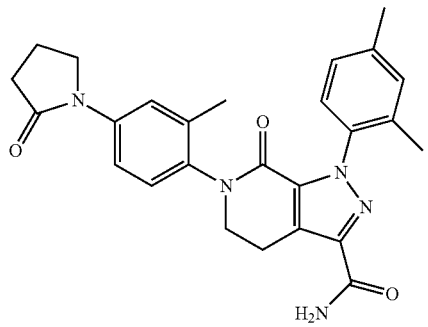 [SMILES: Cc1ccc(-n2nc(C(N)=O)c3c2C(=O)N(c2ccc(N4CCCC4=O)cc2C)CC3)c(C)c1]

Preparation scheme is shown below:

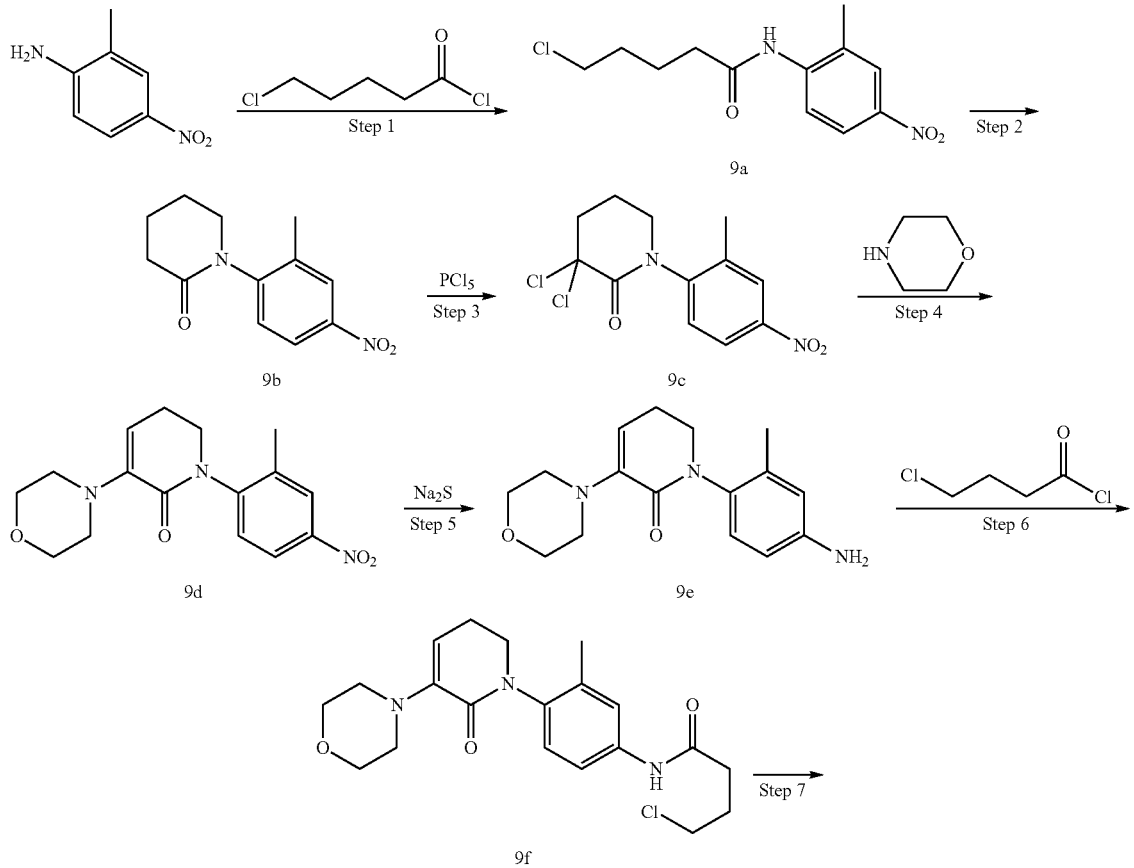

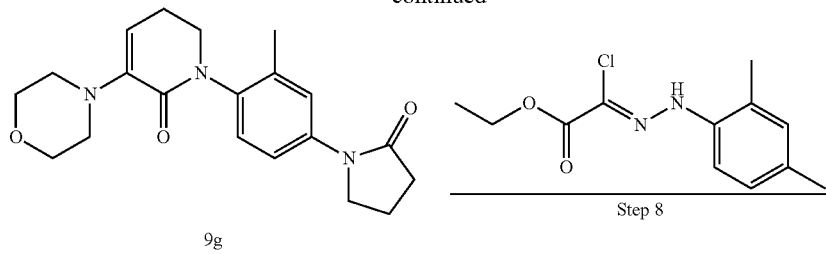

9g

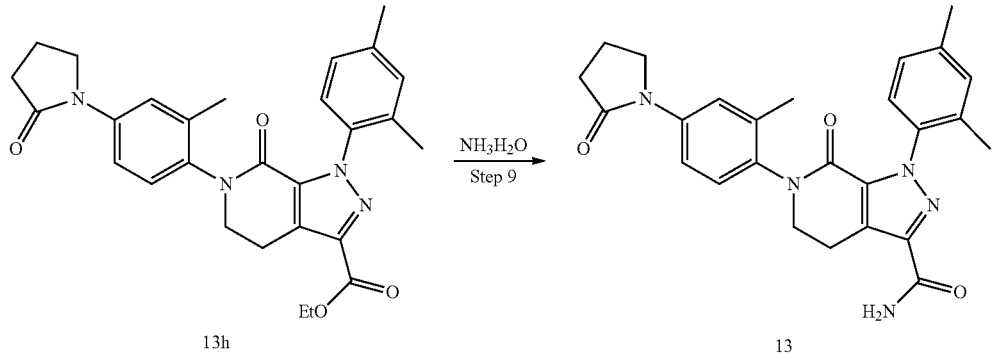

13h → 13

Step 1 was carried out in the same manner as the step 1 in Example 9;
Step 2 was carried out in the same manner as the step 2 in Example 9;
Step 3 was carried out in the same manner as the step 3 in Example 9;
Step 4 was carried out in the same manner as the step 4 in Example 9;
Step 5 was carried out in the same manner as the step 5 in Example 9;
Step 6 was carried out in the same manner as the step 6 in Example 9;
Step 7 was carried out in the same manner as the step 7 in Example 9;

Step 8: Preparation of Compound 13h

The compound 9 g (350 mg, 0.98 mmol) was dissolved in toluene (20 ml). Ethyl [(2,4-dimethyl-phenyl)hydrazino]chloroacetate (300 mg, 1.18 mmol) and triethylamine (300 mg, 2.97 mmol) were added at room temperature to give a reaction mixture, which was refluxed overnight at 120° C. TLC was used to monitor the reaction progress. After the reaction was completed, toluene was removed by distillation under reduced pressure. The residue was dissolved by dichloromethane (20 ml). Trifluoroacetic acid (1.5 ml) was added at room temperature to obtain a reaction mixture, which was reacted overnight at room temperature. TLC was used to monitor the reaction progress. After the reaction was completed, the reaction mixture was purified by column chromatography to give compound 13h (420 mg, yellow solid), yield: 87.6%.
MS m/z (ES): 487.2 [M+1]

Step 9: Preparation of 1-(2,4-dimethyl-phenyl)-7-oxo-6-[2-methyl-4-(2-oxo-pyrrolidin-1-yl)phenyl]-4,5,6,7-tetrahydro-1H-pyrazolo[3,4-c]pyridine-3-carboxamide The compound 13h (420 mg, 0.86 mmol) was dissolved in methanol (6 ml). Aqueous ammonia (4 ml) was added to give a reaction mixture, which was refluxed overnight at 70° C. TLC was used to monitor the reaction progress. After the reaction was completed, the reaction mixture was purified by column chromatography to give compound 13 (260 mg, light yellow solid), yield: 65.8%.
MS m/z (ES): 458.2 [M+1]

$^1$H NMR (400 MHz, CDCl$_3$) δ 7.48 (d, J=2.3 Hz, 1H), 7.43 (dd, J=8.5, 2.4 Hz, 1H), 7.18 (d, J=7.8 Hz, 1H), 7.14 (d, J=8.5 Hz, 1H), 7.08-7.06 (m, 2H), 6.85 (br s, 1H), 5.58 (br s, 1H), 4.07-4.00 (m, 1H), 3.85-3.78 (m, 3H), 3.47-3.34 (m, 2H), 2.59 (t, J=8.1 Hz, 2H), 2.33 (s, 3H), 2.23 (s, 3H), 2.18-2.10 (m, 2H), 2.06 (s, 3H).

Example 14: Preparation of 1-(3,5-difluoro-phenyl)-7-oxo-6-[2-methyl-4-(2-oxo-pyrrolidin-1-yl)phenyl]-4,5,6,7-tetrahydro-1H-pyrazolo[3,4-c]pyridine-3-carboxamide

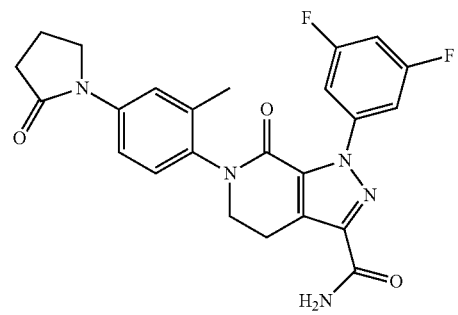 [SMILES: Cc1cc(N2CCCC2=O)ccc1N1CCc2c(C(N)=O)nn(-c3cc(F)cc(F)c3)c2C1=O]

Preparation scheme is shown below:

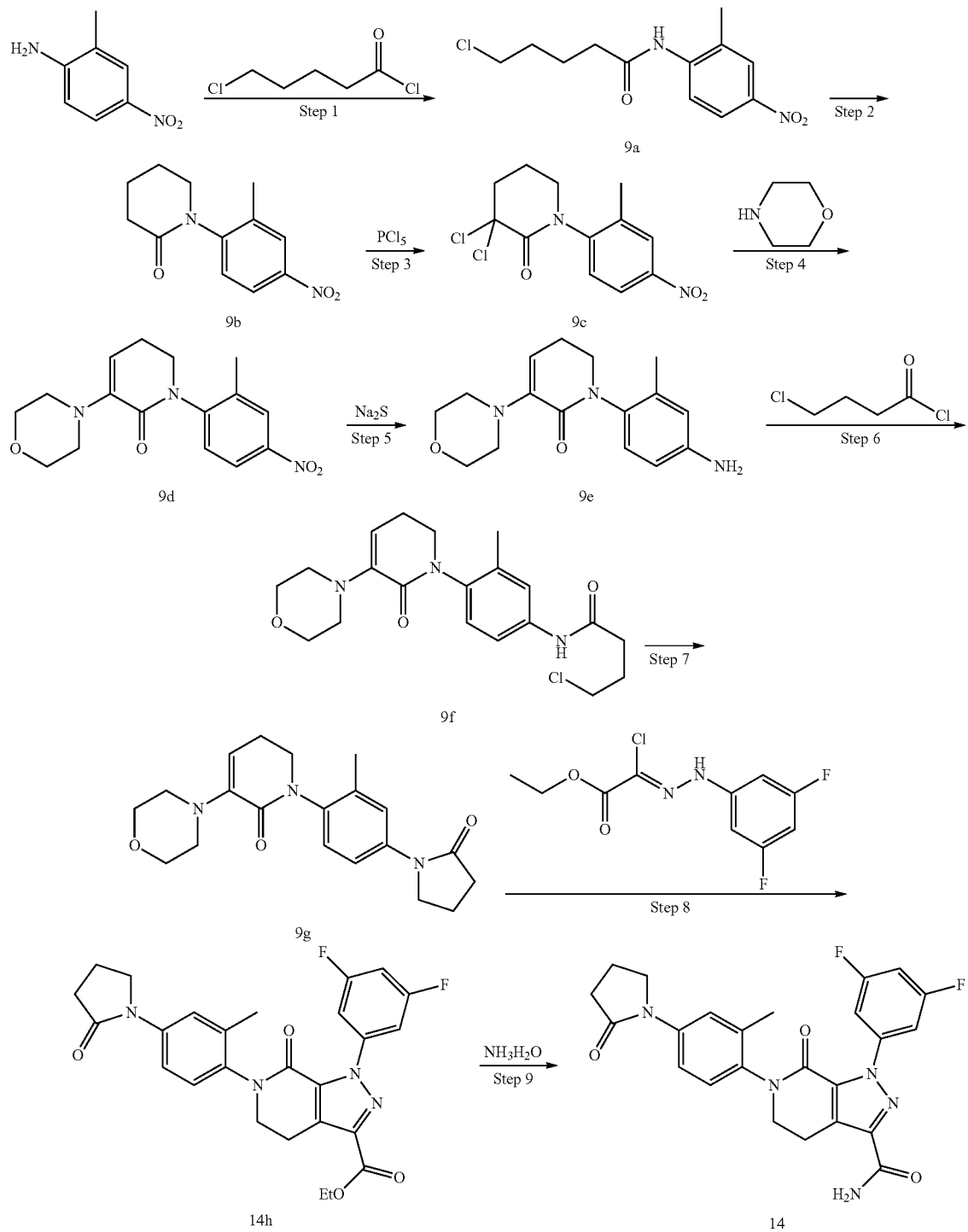

Step 1 was carried out in the same manner as the step 1 in Example 9;
Step 2 was carried out in the same manner as the step 2 in Example 9;
Step 3 was carried out in the same manner as the step 3 in Example 9;
Step 4 was carried out in the same manner as the step 4 in Example 9;
Step 5 was carried out in the same manner as the step 5 in Example 9;
Step 6 was carried out in the same manner as the step 6 in Example 9;
Step 7 was carried out in the same manner as the step 7 in Example 9;

Step 8: Preparation of Compound 14h

The compound 9 g (350 mg, 0.98 mmol) was dissolved in toluene (20 ml). Ethyl [(3,5-difluoro-phenyl)hydrazino]chloroacetate (310 mg, 1.18 mmol) and triethylamine (300 mg, 2.97 mmol) were added at room temperature to give a reaction mixture, which was refluxed overnight at 120° C. TLC was used to monitor the reaction progress. After the reaction was completed, toluene was removed by distillation under reduced pressure. The residue was dissolved by dichloromethane (20 ml). Trifluoroacetic acid (1.5 ml) was added at room temperature to obtain a reaction mixture, which was reacted overnight at room temperature. TLC was used to monitor the reaction progress. After the reaction was completed, the reaction mixture was purified by column chromatography to give compound 14h (431 mg, yellow solid), yield: 88.5%.

MS m/z (ES): 495.2 [M+1]

Step 9: Preparation of 1-(3,5-difluoro-phenyl)-7-oxo-6-[2-methyl-4-(2-oxo-pyrrolidin-1-yl)phenyl]-4,5,6,7-tetrahydro-1H-pyrazolo[3,4-c]pyridine-3-carboxamide The compound 14h (431 mg, 0.87 mmol) was dissolved in methanol (6 ml). Aqueous ammonia (4 ml) was added to give a reaction mixture, which was refluxed overnight at 70° C. TLC was used to monitor the reaction progress. After the reaction was completed, the reaction mixture was purified by column chromatography to give compound 14 (235 mg, light yellow solid), yield: 57.9%.

MS m/z (ES): 466.2 [M+1]

$^1$H NMR (400 MHz, CDCl$_3$) δ 7.53-7.50 (m, 2H), 7.28-7.23 (m, 2H), 7.19 (d, J=8.3 Hz, 1H), 6.88-6.83 (m, 2H), 5.61 (br s, 1H), 4.10-4.03 (m, 1H), 3.86-3.80 (m, 3H), 3.48-3.31 (m, 2H), 2.61 (t, J=8.1 Hz, 2H), 2.27 (s, 3H), 2.20-2.12 (m, 2H).

Example 15: Preparation of 1-(3-fluoro-4-methoxy-phenyl)-7-oxo-6-[2-methyl-4-(2-oxo-pyrrolidin-1-yl)phenyl]-4,5,6,7-tetrahydro-1H-pyrazolo[3,4-c]pyridine-3-carb oxamide

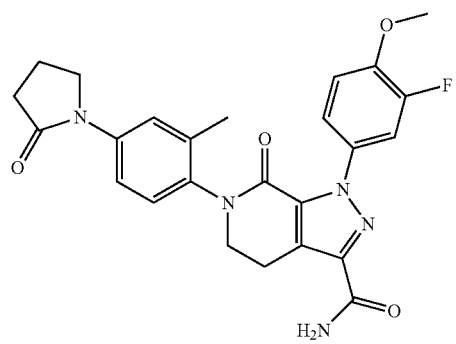 [SMILES: COc1ccc(-n2nc(C(N)=O)c3c2C(=O)N(c2ccc(N4CCCC4=O)cc2C)CC3)cc1F]

Preparation scheme is shown below:

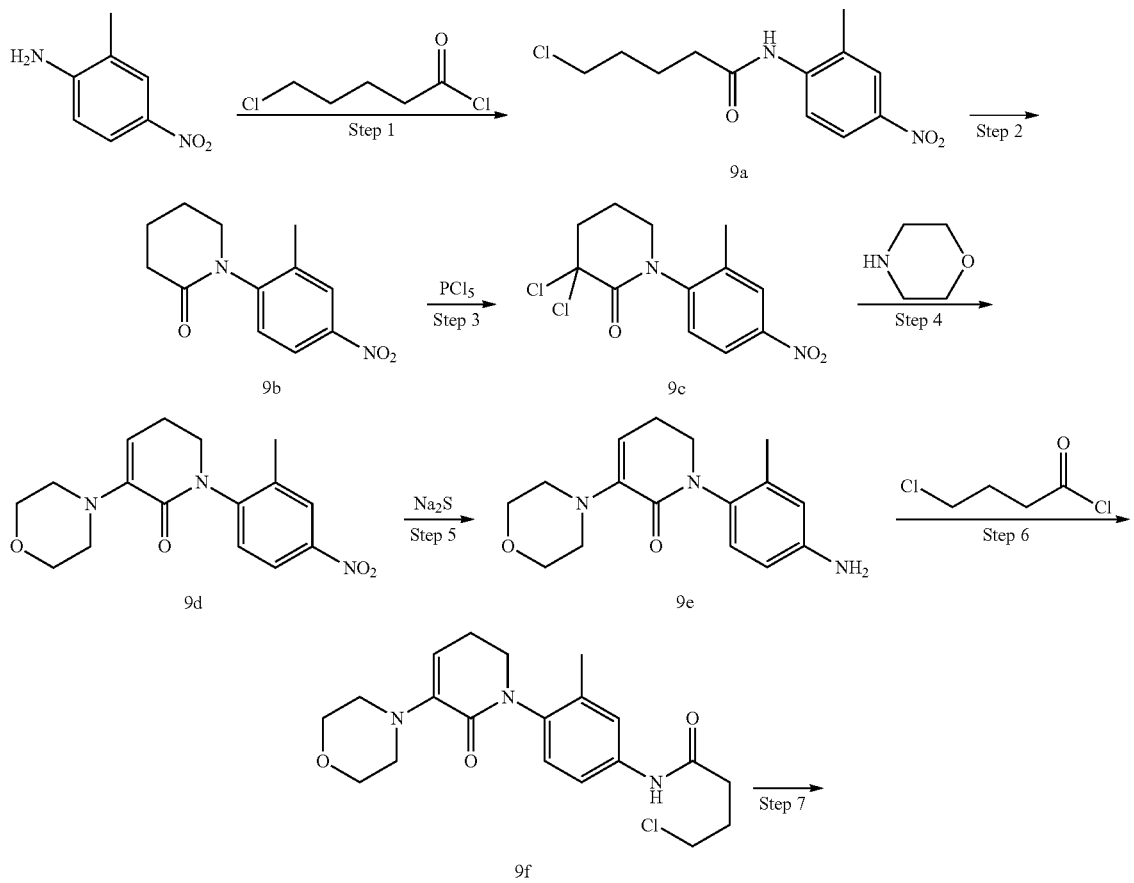

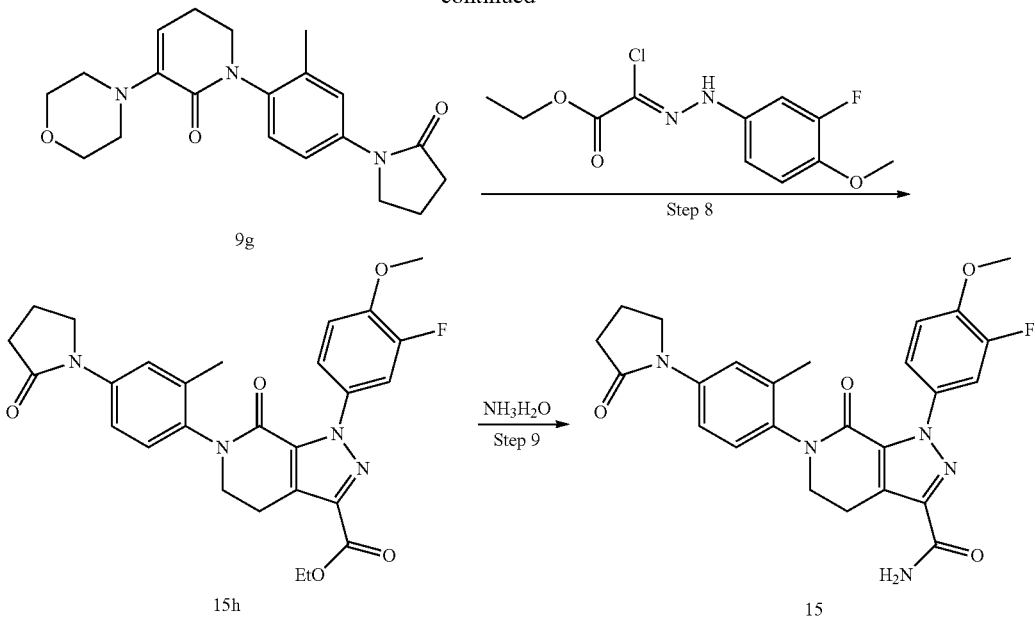

Step 1 was carried out in the same manner as the step 1 in Example 9;
Step 2 was carried out in the same manner as the step 2 in Example 9;
Step 3 was carried out in the same manner as the step 3 in Example 9;
Step 4 was carried out in the same manner as the step 4 in Example 9;
Step 5 was carried out in the same manner as the step 5 in Example 9;
Step 6 was carried out in the same manner as the step 6 in Example 9;
Step 7 was carried out in the same manner as the step 7 in Example 9;

Step 8: Preparation of Compound 15h

The compound 9 g (350 mg, 0.98 mmol) was dissolved in toluene (20 ml). Ethyl [(3-fluoro-4-methoxyphenyl)hydrazino]chloroacetate (324 mg, 1.18 mmol) and triethylamine (300 mg, 2.97 mmol) were added at room temperature to give a reaction mixture, which was refluxed overnight at 120° C. TLC was used to monitor the reaction progress. After the reaction was completed, toluene was removed by distillation under reduced pressure. The residue was dissolved by dichloromethane (20 ml). Trifluoroacetic acid (1.5 ml) was added at room temperature to obtain a reaction mixture, which was reacted overnight at room temperature. TLC was used to monitor the reaction progress. After the reaction was completed, the reaction mixture was purified by column chromatography to give compound 15h (427 mg, yellow solid), yield: 85.6%.

MS m/z (ES): 507.2 [M+1]

Step 9: Preparation of 1-(3-fluoro-4-methoxyphenyl)-7-oxo-6-[2-methyl-4-(2-oxo-pyrrolidin-1-yl)phenyl]-4,5,6,7-tetrahydro-1H-pyrazolo[3,4-c]pyridine-3-carboxamide The compound 15h (427 mg, 0.84 mmol) was dissolved in methanol (7 ml). Aqueous ammonia (5 ml) was added to give a reaction mixture, which was refluxed overnight at 70° C. TLC was used to monitor the reaction progress. After the reaction was completed, the reaction mixture was purified by column chromatography to give compound 15 (255 mg, light yellow solid), yield: 63.3%.

MS m/z (ES): 478.2 [M+1]

$^1$H NMR (400 MHz, CDCl$_3$) δ 7.51 (d, J=2.3 Hz, 1H), 7.49 (dd, J=8.5, 2.5 Hz, 1H), 7.40-7.34 (m, 2H), 7.18 (d, J=8.5 Hz, 1H), 6.97 (t, J=8.9 Hz, 1H), 6.86 (br s, 1H), 5.59 (br s, 1H), 4.09-4.02 (m, 1H), 3.90 (s, 3H), 3.85-3.78 (m, 3H), 3.47-3.30 (m, 2H), 2.61 (t, J=8.1 Hz, 2H), 2.26 (s, 3H), 2.20-2.12 (m, 2H).

Example 16: Preparation of 1-(4-methoxyphenyl)-7-oxo-6-[3-methyl-4-(2-oxo-pyrrolidin-1-yl)phenyl]-4,5,6,7-tetrahydro-1H-pyrazolo[3,4-c]pyridine-3-carboxamide

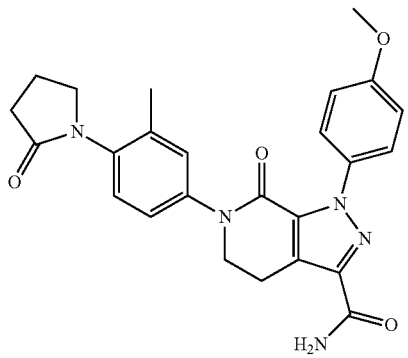 [SMILES: COc1ccc(-n2nc(C(N)=O)c3c2C(=O)N(c2ccc(N4CCCC4=O)c(C)c2)CC3)cc1]

Preparation scheme is shown below:

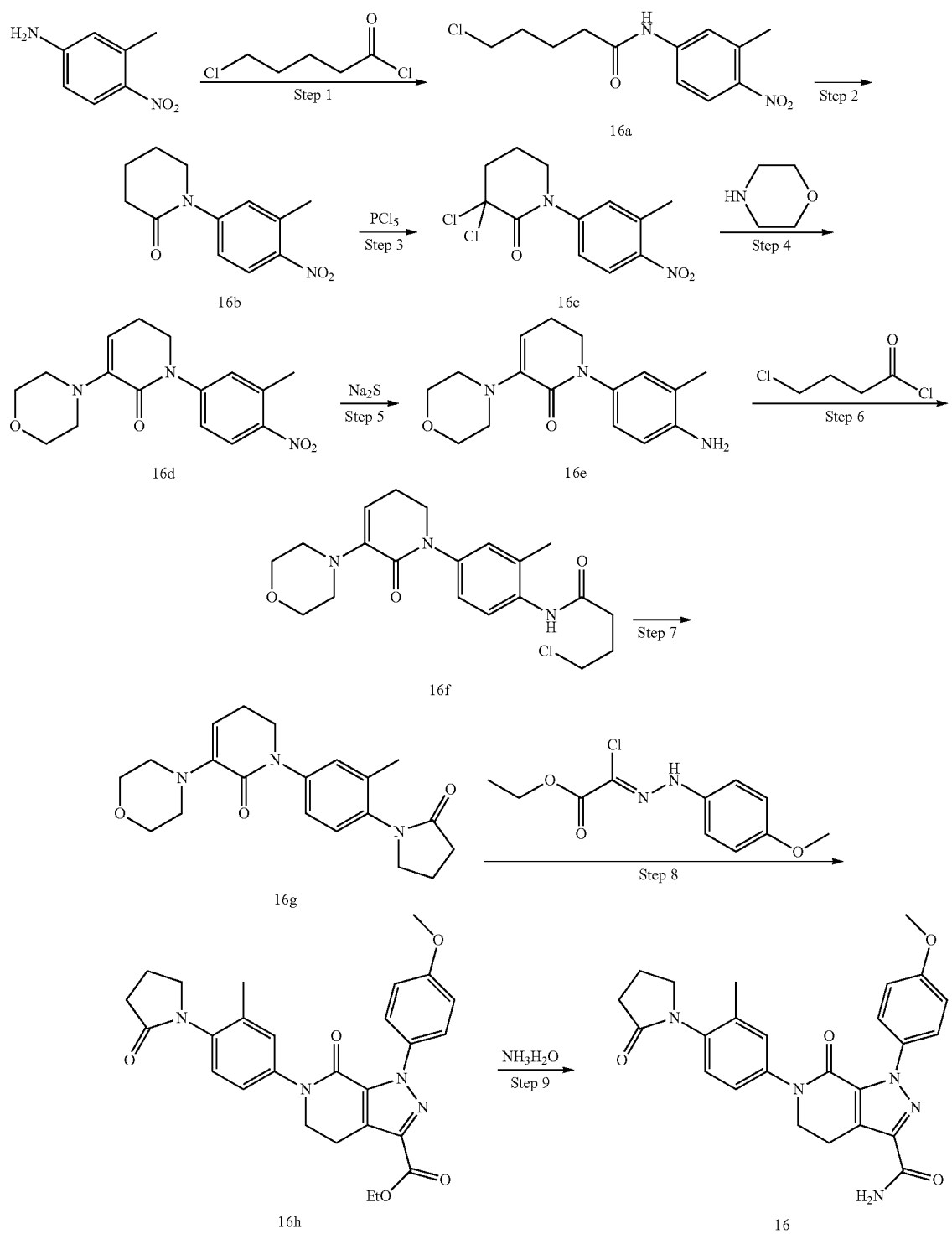

Step 1: Preparation of Compound 16a

The 3-methyl-4-nitroaniline (3 g, 19.7 mmol) was dissolved in dichloromethane (60 ml). N,N-diisopropylethylamine (5.1 g, 39.5 mmol) was added, cooled in ice bath to 5° C. or lower. 5-chlorovaleryl chloride (3.7 g, 23.9 mmol) was added dropwise to obtain a reaction mixture. The reaction mixture was reacted overnight at room temperature. TLC was used to monitor the reaction progress. After the reaction was completed, water was poured into the reaction solution, then the reaction mixture was separated and washed with water for three times, dried over anhydrous magnesium sulfate, filtered, and the solvent was distilled off under reduced pressure to give compound 16a (4.4 g, yellow solid), yield: 82.4%.

MS m/z (ES): 271.1 [M+1]

Step 2: Preparation of Compound 16b

The compound 16a (4.4 g, 16.3 mmol) was dissolved in tetrahydrofuran (80 ml). Sodium hydride (0.78 g, 32.6 mmol) was added portion-wise under an ice bath to obtain a reaction mixture. Then the reaction mixture was reacted overnight at room temperature. TLC was used to monitor the reaction progress. After the reaction was completed, ice-water was added into the reaction solution under an ice bath to quench sodium hydride. After removing tetrahydrofuran by distillation under reduced pressure, the residue was extracted twice by ethyl acetate, dried over anhydrous magnesium sulfate, filtered, and the solvent was distilled off under reduced pressure. The residue was purified by column chromatography to give compound 16b (3.4 g, yellow solid), yield: 89.2%.

MS m/z (ES): 235.1 [M+1]

Step 3: Preparation of Compound 16c

The compound 16b (3.4 g, 14.5 mol) was dissolved in dichloromethane (100 ml). Phosphorus pentachloride (9.05 g, 43.5 mmol) was added portion-wise under an ice bath to obtain a reaction mixture. The reaction mixture was refluxed at 40° C. When the reaction solution generated little bubble, TLC was used to monitor the reaction progress. After the reaction was completed, ice-water was added into the reaction mixture under an ice bath to quench phosphorus pentachloride. The reaction solution was separated, washed with water for three times, dried over anhydrous magnesium sulfate, filtered, and the solvent was removed by distillation under reduced pressure to give compound 16c (4 g, yellow solid), yield: 90.9%.

MS m/z (ES): 303.0, 305.0 [M+1]

Step 4: Preparation of Compound 16d

The compound 16c (4 g, 13.2 mmol) was dissolved in morpholine (40 ml) to obtain a reaction mixture, which was refluxed at 120° C. for 2 hours, TLC was used to monitor the reaction progress. After the reaction was completed, ethyl acetate was added, the obtained solution was washed with water for three times, dried over anhydrous magnesium sulfate, filtered, and the solvent was removed by distillation under reduced pressure to give compound 16d (3.7 g, black solid), yield: 88.6%.

MS m/z (ES): 318.1 [M+1]

Step 5: Preparation of Compound 16e

The compound 16d (3.7 g, 11.7 mmol) was dissolved in ethanol (50 ml). Sodium sulfide nonahydrate (8.4 g, 35.1 mmol) was added, and then water (20 ml) was added to obtain a reaction mixture, which was refluxed overnight at 50° C. TLC was used to monitor the reaction progress. After the reaction was completed, ethanol was removed by distillation under reduced pressure, the residue was extracted by ethyl acetate for three times, the combined organic phases were dried over anhydrous magnesium sulfate, filtered, and the solvent was removed by distillation under reduced pressure to give compound 16e (3.1 g, yellow solid) yield: 92.3%.

MS m/z (ES): 288.2 [M+1]

Step 6: Preparation of Compound 16f

The compound 16e (3.1 g, 10.8 mmol) was dissolved in dichloromethane (50 ml). N,N-diisopropylethylamine (3.5 g, 27.1 mmol) was added, cooled in ice bath, 4-chlorobutyryl chloride (2.3 g, 16.2 mmol) was added dropwise to obtain a reaction mixture. The reaction mixture was reacted overnight at room temperature. TLC was used to monitor the reaction progress. After the reaction was completed, water was added into the reaction solution, which was separated and washed with water for three times, dried over anhydrous magnesium sulfate, filtered, and the solvent was distilled off under reduced pressure to give compound 16f (3.6 g, yellow solid), yield: 85.2%.

MS m/z (ES): 392.2 [M+1]

Step 7: Preparation of Compound 16 g

The compound 16f (3.6 g, 9.2 mmol) was dissolved in tetrahydrofuran (50 ml). Sodium hydride (0.6 g, 25 mmol) was added portion-wise under an ice bath to obtain a reaction mixture. Then the reaction mixture was reacted overnight at room temperature. TLC was used to monitor the reaction progress. After the reaction was completed, ice-water was added into the reaction solution under an ice bath to quench sodium hydride. After removing tetrahydrofuran by distillation under reduced pressure, the residue was extracted twice with dichloromethane, the combined organic phases were dried over anhydrous magnesium sulfate, filtered, and the solvent was distilled off under reduced pressure. The residue was purified by column chromatography to give compound 16 g (2.7 g, yellow solid), yield: 82.6%.

MS m/z (ES): 356.2 [M+1]

Step 8: Preparation of Compound 16h

The compound 16 g (300 mg, 0.84 mmol) was dissolved in toluene (10 ml). Ethyl [(4-methoxyphenyl)hydrazino]chloroacetate (258 mg, 1.01 mmol) and triethylamine (254 mg, 2.5 mmol) were added at room temperature to give a reaction mixture, which was refluxed overnight at 120° C. TLC was used to monitor the reaction progress. After the reaction was completed, toluene was removed by distillation under reduced pressure. The residue was dissolved by dichloromethane (20 ml). Trifluoroacetic acid (2 ml) was added at room temperature to obtain a reaction mixture, which was reacted overnight at room temperature. TLC was used to monitor the reaction progress. After the reaction was completed, the reaction mixture was purified by column chromatography to give compound 16h (320 mg, yellow solid), yield: 77.7%.

MS m/z (ES): 489.2 [M+1]

Step 9: Preparation of 1-(4-methoxyphenyl)-7-oxo-6-[3-methyl-4-(2-oxo-pyrrolidin-1-yl)phenyl]-4,5,6,7-tetrahydro-1H-pyrazolo[3,4-c]pyridine-3-carboxamide 16

The compound 16h (320 mg, 0.66 mmol) was dissolved in methanol (4 ml). Aqueous ammonia (2 ml) was added to give a reaction mixture, which was refluxed overnight at 70° C. TLC was used to monitor the reaction progress. After the reaction was completed, the reaction mixture was purified by column chromatography to give compound 16 (220 mg, light yellow solid), yield: 73.1%.

MS m/z (ES): 460.2 [M+1]

$^1$H NMR (400 MHz, CDCl$_3$) δ 7.49-7.45 (m, 2H), 7.23 (d, J=2.1 Hz, 1H), 7.19-7.13 (m, 2H), 6.95-6.91 (m, 2H), 6.86 (br s, 1H), 5.60 (br s, 1H), 4.09 (t, J=6.7 Hz, 2H), 3.82 (s, 3H), 3.67 (t, J=7.0 Hz, 2H), 3.37 (t, J=6.7 Hz, 2H), 2.57 (t, J=8.1 Hz, 2H), 2.25-2.18 (m, 5H).

Example 17: Preparation of 1-(3,5-difluoro-phenyl)-7-oxo-6-[3-methyl-4-(2-oxo-pyrrolidin-1-yl)phenyl]-4,5,6,7-tetrahydro-1H-pyrazolo[3,4-c]pyridine-3-carb oxamide
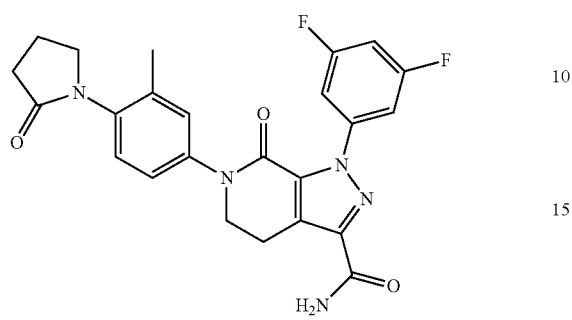
Preparation scheme is shown below:
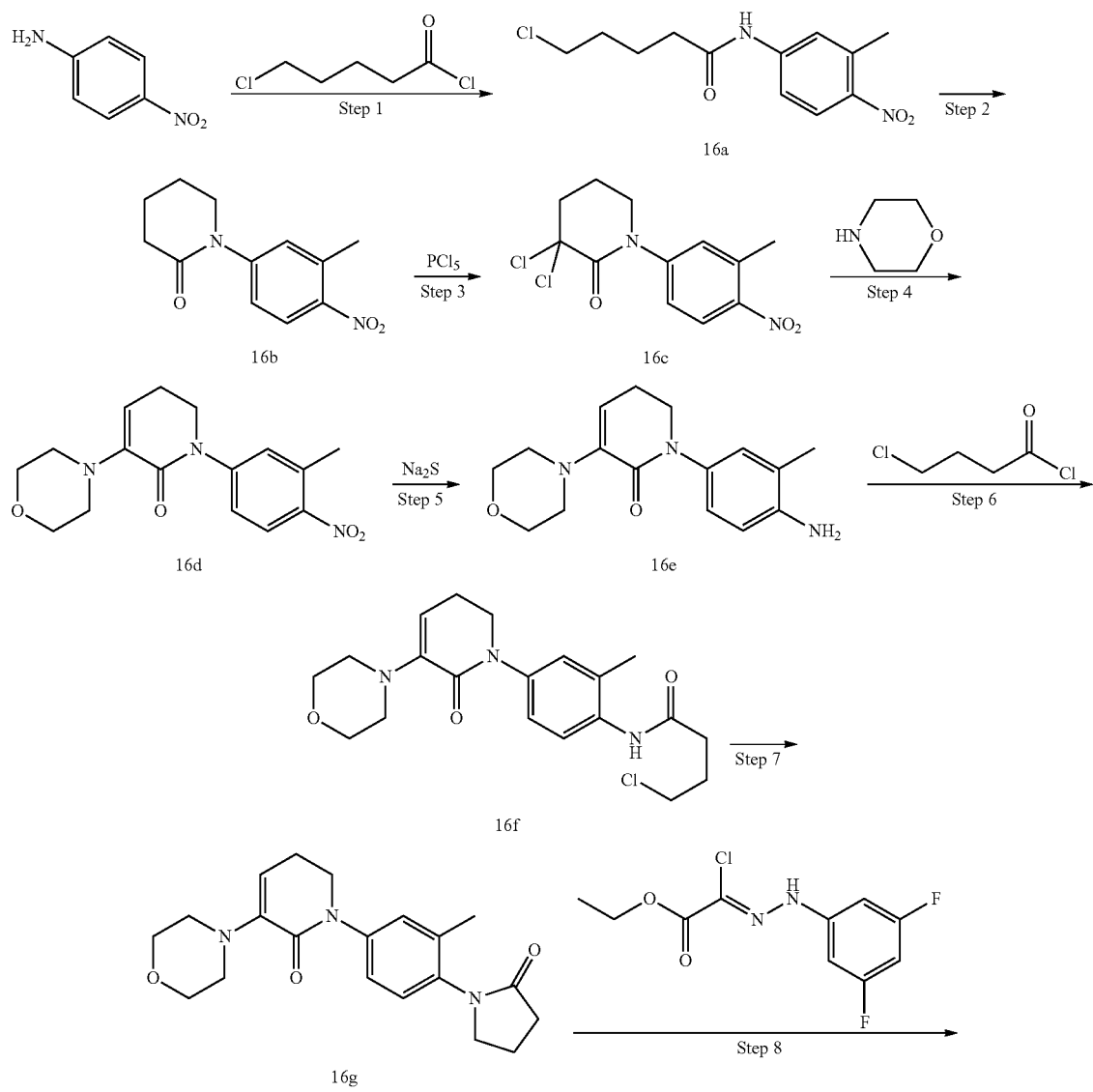

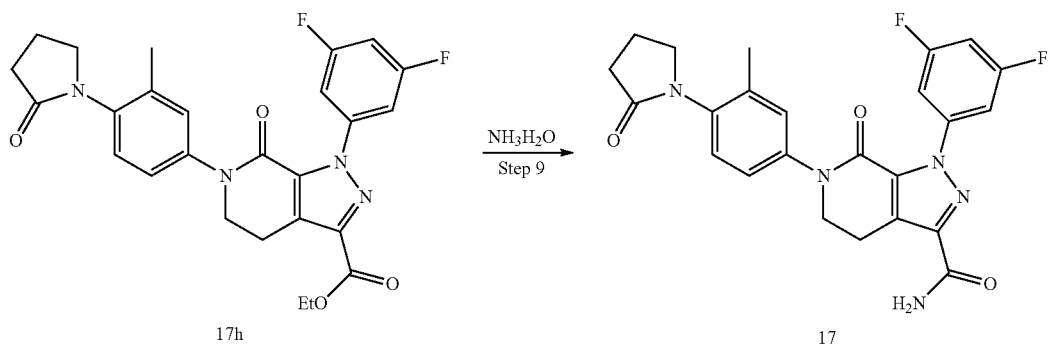

Step 1 was carried out in the same manner as the step 1 in Example 16;
Step 2 was carried out in the same manner as the step 2 in Example 16;
Step 3 was carried out in the same manner as the step 3 in Example 16;
Step 4 was carried out in the same manner as the step 4 in Example 16;
Step 5 was carried out in the same manner as the step 5 in Example 16;
Step 6 was carried out in the same manner as the step 6 in Example 16;
Step 7 was carried out in the same manner as the step 7 in Example 16;

Step 8: Preparation of Compound 17h

The compound 16 g (300 mg, 0.84 mmol) was dissolved in toluene (10 ml). Ethyl [(3,5-difluoro-phenyl)hydrazino] chloroacetate (265 mg, 1.01 mmol) and triethylamine (254 mg, 2.5 mmol) were added at room temperature to give a reaction mixture, which was refluxed overnight at 120° C. TLC was used to monitor the reaction progress. After the reaction was completed, toluene was removed by distillation under reduced pressure. The residue was dissolved by dichloromethane (20 ml). Trifluoroacetic acid (2 ml) was added at room temperature to obtain a reaction mixture, which was reacted overnight at room temperature. TLC was used to monitor the reaction progress. After the reaction was completed, the reaction mixture was purified by column chromatography to give compound 17h (342 mg, yellow solid), yield: 81.9%.

MS m/z (ES): 495.2 [M+1]

Step 9: Preparation of 1-(3,5-difluoro-phenyl)-7-oxo-6-[3-methyl-4-(2-oxo-pyrrolidin-1-yl)phenyl]-4,5,6,7-tetrahydro-1H-pyrazolo[3,4-c]pyridine-3-carboxamide The compound 17h (342 mg, 0.69 mmol) was dissolved in methanol (4 ml). Aqueous ammonia (3 ml) was added to give a reaction mixture, which was refluxed overnight at 70° C. TLC was used to monitor the reaction progress. After the reaction was completed, the reaction mixture was purified by column chromatography to give compound 17 (197 mg, light yellow solid), yield: 61.2%.

MS m/z (ES): 466.2 [M+1]

$^1$H NMR (400 MHz, CDCl$_3$) δ 7.24-7.18 (m, 5H), 6.90-6.84 (m, 2H), 5.68 (br s, 1H), 4.10 (t, J=6.7 Hz, 2H), 3.70 (t, J=7.0 Hz, 2H), 3.37 (t, J=6.7 Hz, 2H), 2.58 (t, J=8.1 Hz, 2H), 2.27-2.20 (m, 5H).

Example 18: Preparation of 1-(3-fluoro-4-methoxy-phenyl)-7-oxo-6-[3-methyl-4-(2-oxo-pyrrolidin-1-yl)phenyl]-4,5,6,7-tetrahydro-1H-pyrazolo[3,4-c]pyridine-3-carb oxamide

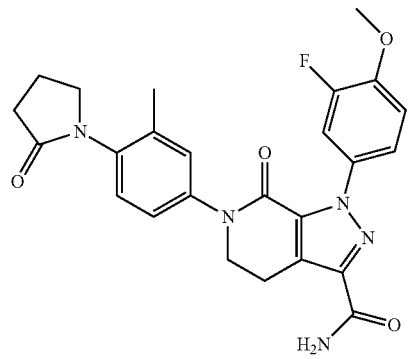 [SMILES: COc1ccc(-n2nc(C(N)=O)c3c2C(=O)N(c2ccc(N4CCCC4=O)c(C)c2)CC3)cc1F]

Preparation scheme is shown below:

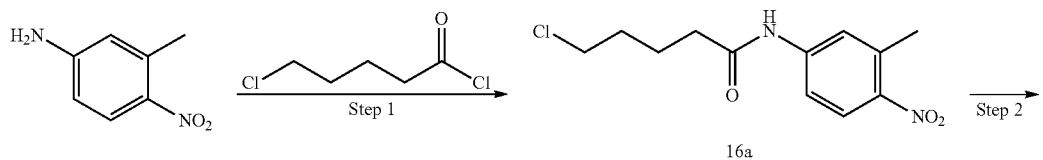

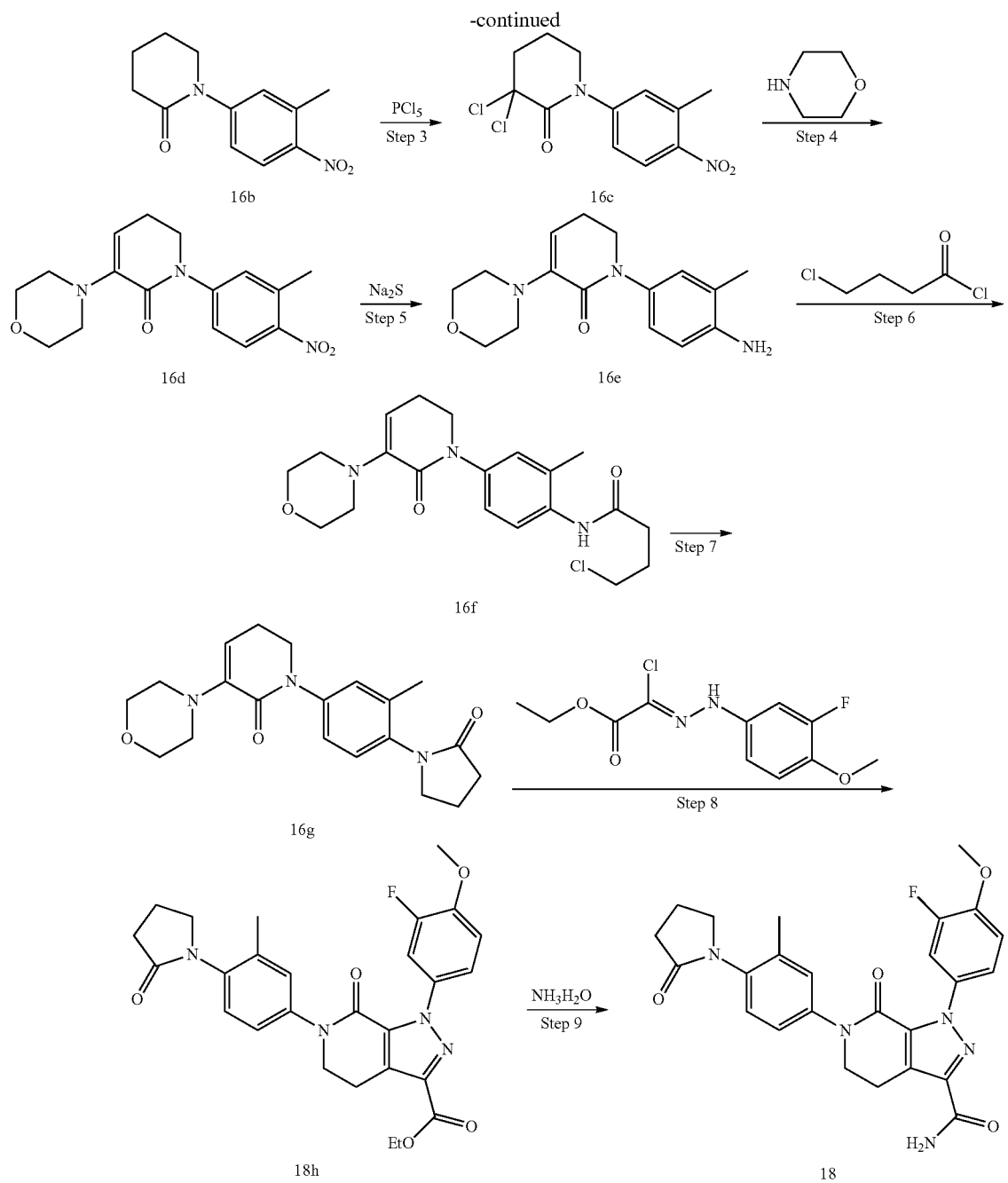

Step 1 was carried out in the same manner as the step 1 in Example 16;
Step 2 was carried out in the same manner as the step 2 in Example 16;
Step 3 was carried out in the same manner as the step 3 in Example 16;
Step 4 was carried out in the same manner as the step 4 in Example 16;
Step 5 was carried out in the same manner as the step 5 in Example 16;
Step 6 was carried out in the same manner as the step 6 in Example 16;
Step 7 was carried out in the same manner as the step 7 in Example 16;

Step 8: Preparation of Compound 18h

The compound 16 g (300 mg, 0.84 mmol) was dissolved in toluene (10 ml). Ethyl [(3-fluoro-4-methoxyphenyl)hydrazino]chloroacetate (277 mg, 1.01 mmol) and triethylamine (254 mg, 2.5 mmol) were added at room temperature to give a reaction mixture, which was refluxed overnight at 120° C. TLC was used to monitor the reaction progress. After the reaction was completed, toluene was removed by distillation under reduced pressure. The residue was dissolved by dichloromethane (20 ml). Trifluoroacetic acid (2 ml) was added at room temperature to obtain a reaction mixture, which was reacted overnight at room temperature. TLC was used to monitor the reaction progress. After the reaction was completed, the reaction mixture was purified by column chromatography to give compound 18h (355 mg, yellow solid), yield: 83.0%.

MS m/z (ES): 507.2 [M+1]

Step 9: Preparation of 1-(3-fluoro-4-methoxyphenyl)-7-oxo-6-[3-methyl-4-(2-oxo-pyrrolidin-1-yl)phenyl]-4,5,6,7-tetrahydro-1H-pyrazolo[3,4-c]pyridine-3-carboxamide The compound 18h (342 mg, 0.70 mmol) was dissolved in methanol (4 ml). Aqueous ammonia (3 ml) was added to give a reaction mixture, which was refluxed overnight at 70° C. TLC was used to monitor the reaction progress. After the reaction was completed, the reaction mixture was purified by column chromatography to give compound 18 (209 mg, light yellow solid), yield: 62.4%.

MS m/z (ES): 478.2 [M+1]

$^1$H NMR (400 MHz, CDCl$_3$) δ 7.37-7.31 (m, 2H), 7.23-7.15 (m, 3H), 6.98 (t, J=8.7 Hz, 1H), 6.84 (br s, 1H), 5.64 (br s, 1H), 4.09 (t, J=6.7 Hz, 2H), 3.91 (s, 3H), 3.68 (t, J=7.0 Hz, 2H), 3.37 (t, J=6.7 Hz, 2H), 2.57 (t, J=8.1 Hz, 2H), 2.26-2.18 (m, 5H).

Example 19: Preparation of 1-(4-methoxyphenyl)-7-oxo-6-[2-methyl-4-(2-oxo-piperidin-1-yl)phenyl]-4,5,6,7-tetrahydro-1H-pyrazolo[3,4-c]pyridine-3-carboxamide

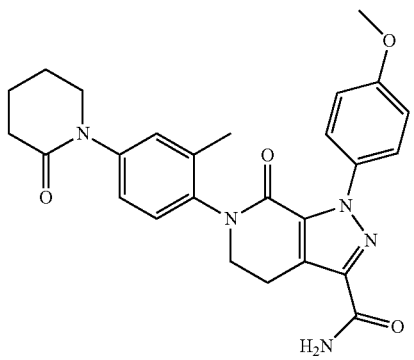 [SMILES: COc1ccc(-n2nc(C(N)=O)c3c2C(=O)N(c2ccc(N4CCCCC4=O)cc2C)CC3)cc1]

Preparation scheme is shown below:

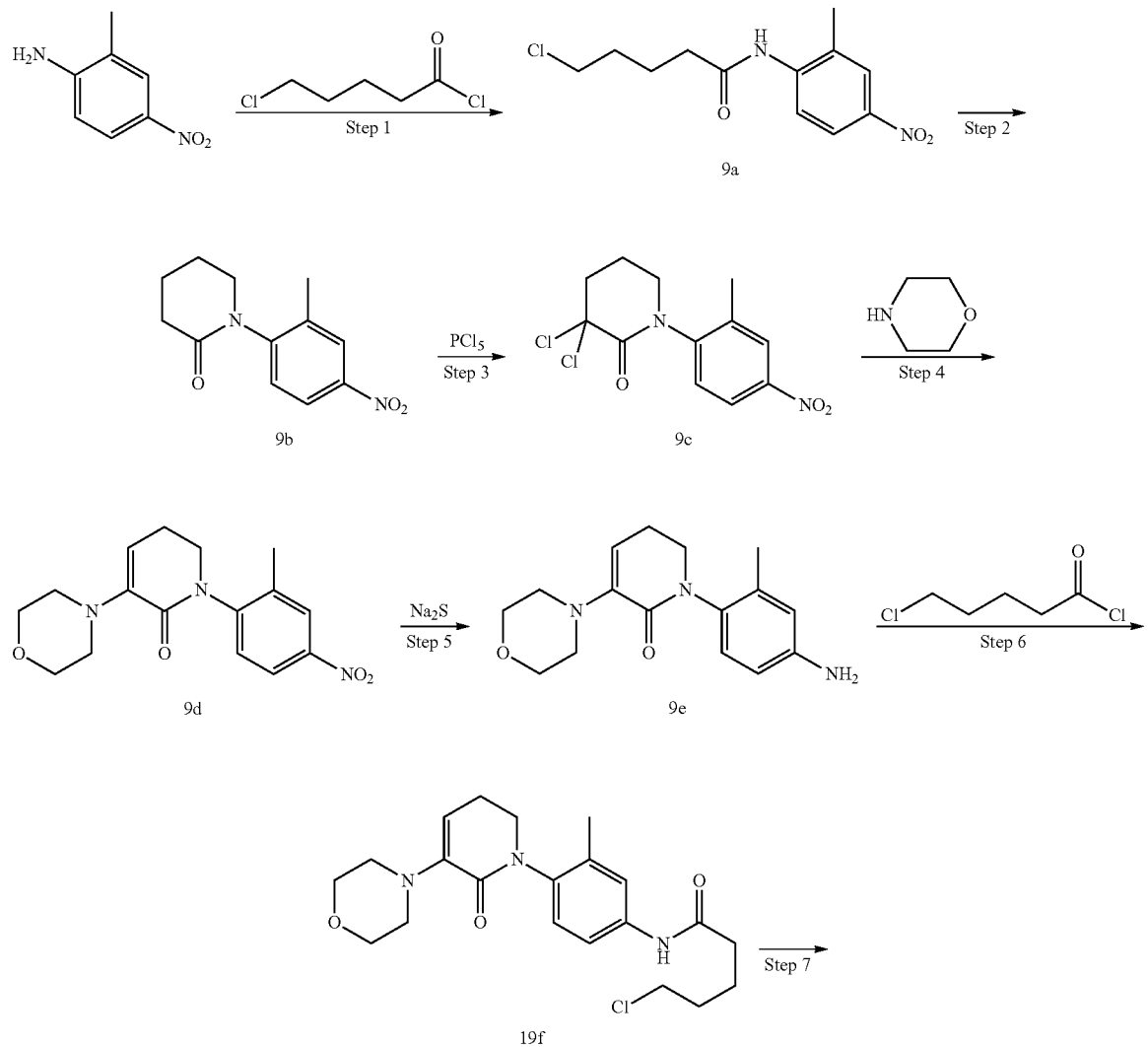

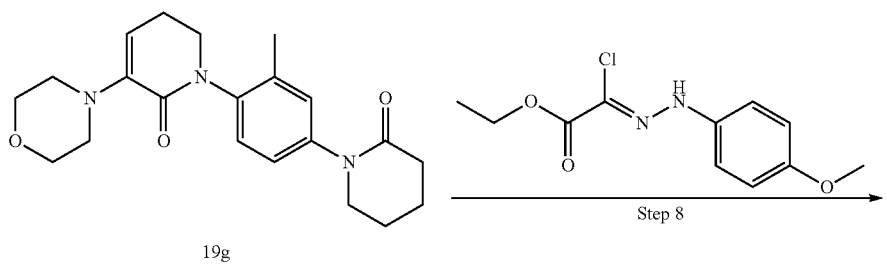

19g

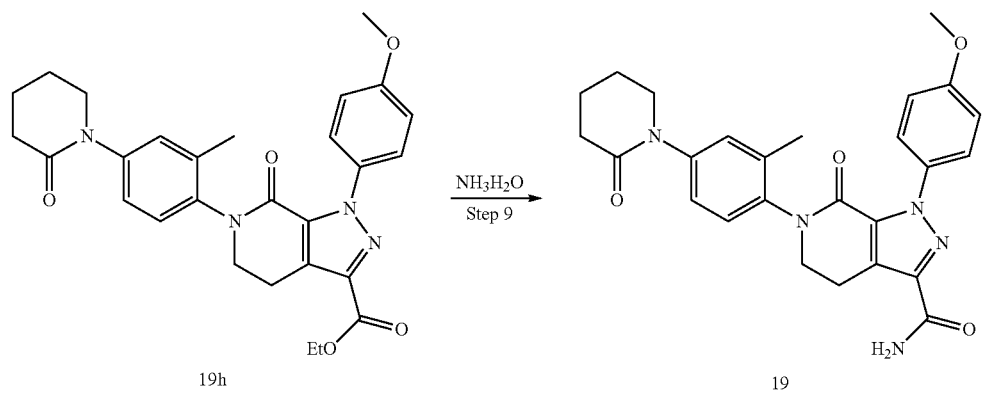

Step 1 was carried out in the same manner as the step 1 in Example 9;

Step 2 was carried out in the same manner as the step 2 in Example 9;

Step 3 was carried out in the same manner as the step 3 in Example 9;

Step 4 was carried out in the same manner as the step 4 in Example 9;

Step 5 was carried out in the same manner as the step 5 in Example 9;

Step 6: Preparation of Compound 19f

The compound 9e (4 g, 13.9 mmol) was dissolved in dichloromethane (60 ml). N,N-diisopropylethylamine (5.4 g, 41.8 mmol) was added, cooled in ice bath, 5-chlorovaleryl chloride (3.24 g, 20.9 mmol) was added dropwise to obtain a reaction mixture. The reaction mixture was reacted overnight at room temperature. TLC was used to monitor the reaction progress. After the reaction was completed, water was added into the reaction solution, which was separated and washed with water for three times, dried over anhydrous magnesium sulfate, filtered, and the solvent was distilled off under reduced pressure to give compound 19f (5.5 g, yellow solid), yield: 97.3%.

MS m/z (ES): 406.2 [M+1]

Step 7: Preparation of Compound 19 g

The compound 19f (5.5 g, 13.6 mmol) was dissolved in tetrahydrofuran (80 ml). Sodium hydride (0.80 g, 33.3 mmol) was added portion-wise under an ice bath to obtain a reaction mixture. Then the reaction mixture was reacted overnight at room temperature. TLC was used to monitor the reaction progress. After the reaction was completed, ice-water was added into the reaction solution to quench sodium hydride. After removing tetrahydrofuran by distillation under reduced pressure, the residue was extracted twice by dichloromethane, the combined organic phases were dried over anhydrous magnesium sulfate, filtered, and the solvent was distilled off under reduced pressure. The residue was purified by column chromatography to give compound 19 g (4.7 g, yellow solid), yield: 94.0%.

MS m/z (ES): 370.2 [M+1]

Step 8: Preparation of Compound 19h

The compound 19 g (591 mg, 1.6 mmol) was dissolved in toluene (20 ml). Ethyl [(4-methoxyphenyl)hydrazino]chloroacetate (490 mg, 1.9 mmol) and triethylamine (483 mg, 4.8 mmol) were added at room temperature to give a reaction mixture, which was refluxed overnight at 120° C. TLC was used to monitor the reaction progress. After the reaction was completed, toluene was removed by distillation under reduced pressure. The residue was dissolved by dichloromethane (40 ml). Trifluoroacetic acid (4 ml) was added at room temperature to obtain a reaction mixture, which was reacted overnight at room temperature. TLC was used to monitor the reaction progress. After the reaction was completed, the reaction mixture was purified by column chromatography to give compound 19h (630 mg, yellow solid), yield: 78.4%.

MS m/z (ES): 503.2 [M+1]

Step 9: Preparation of 1-(4-methoxyphenyl)-7-oxo-6-[2-methyl-4-(2-oxo-piperidin-1-yl)phenyl]-4,5,6,7-tetrahydro-1H-pyrazolo[3,4-c]pyridine-3-carboxamide The compound 19h (630 mg, 1.3 mmol) was dissolved in methanol (10 ml). Aqueous ammonia (8 ml) was added to give a reaction mixture, which was refluxed overnight at 70° C. TLC was used to monitor the reaction progress. After the reaction was completed, the reaction mixture was purified by column chromatography to give compound 19 (406 mg, light yellow solid), yield: 68.4%.

MS m/z (ES): 474.2 [M+1]

$^1$H NMR (400 MHz, CDCl$_3$) δ 7.50 (d, J=8.9 Hz, 2H), 7.21-7.10 (m, 3H), 6.93 (d, J=8.9 Hz, 2H), 6.87 (br s, 1H), 5.60 (br s, 1H), 4.10-4.04 (m, 1H), 3.87-3.81 (m, 4H), 3.58-3.56 (m, 2H), 3.47-3.31 (m, 2H), 2.56-2.53 (m, 2H), 2.24 (s, 3H), 1.93-1.91 (m, 4H).

Example 20: Preparation of 1-(3-fluorophenyl)-7-oxo-6-[2-methyl-4-(2-oxo-piperidin-1-yl)phenyl]-4,5,6,7-tetrahydro-1H-pyrazolo[3,4-c]pyridine-3-carboxamide

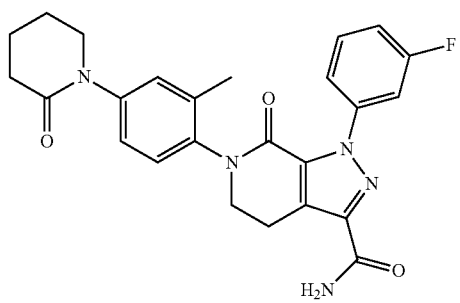 [SMILES: Cc1cc(N2CCCCC2=O)ccc1N1CCc2c(C(N)=O)nn(-c3cccc(F)c3)c2C1=O]

Preparation scheme is shown below:

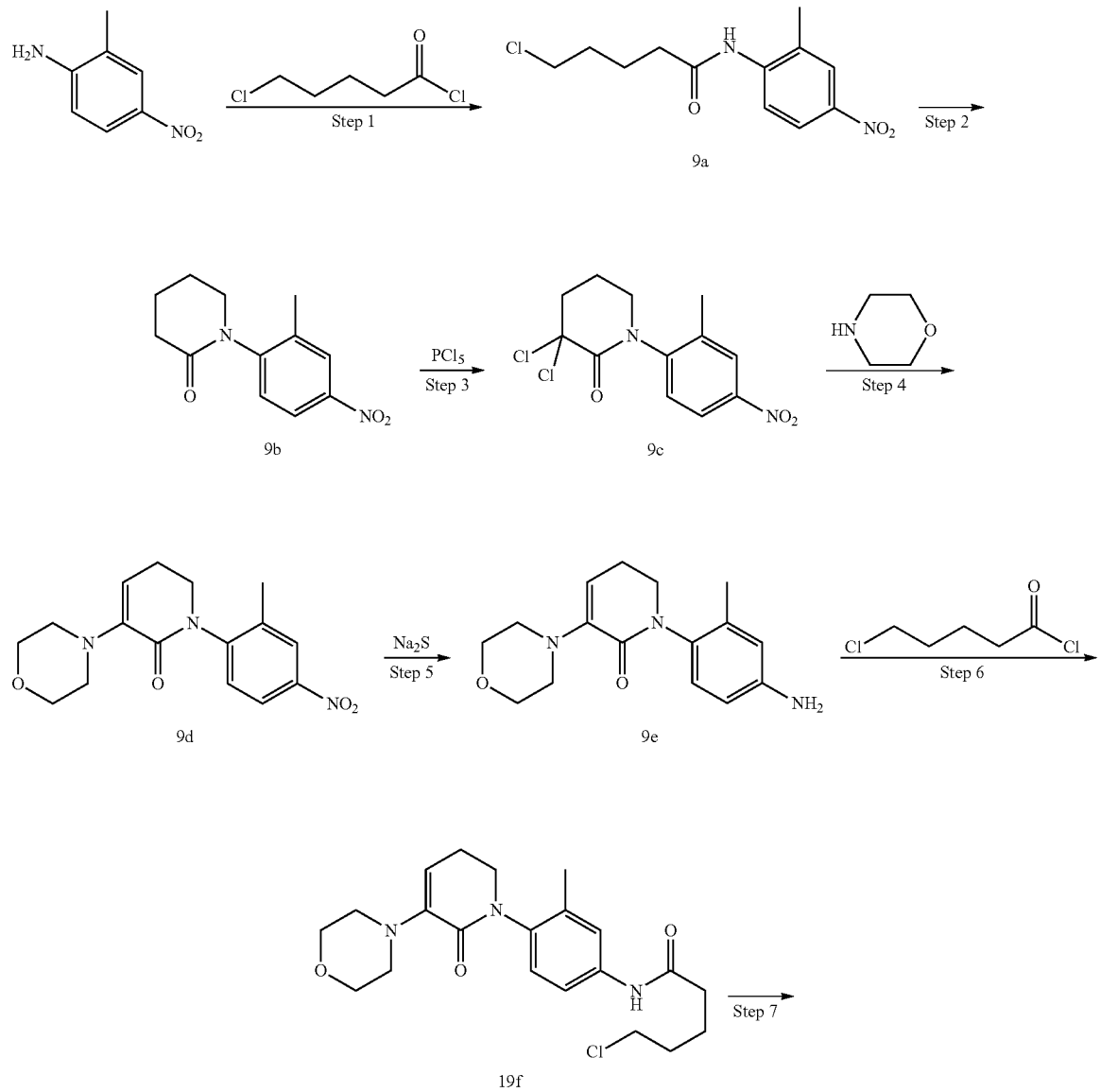

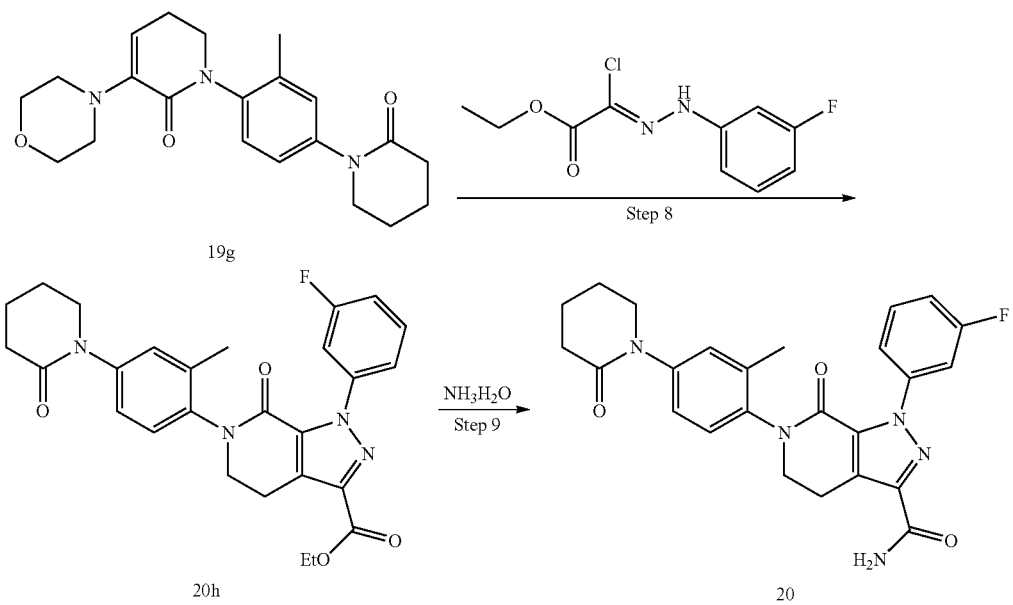

Step 1 was carried out in the same manner as the step 1 in Example 9;
Step 2 was carried out in the same manner as the step 2 in Example 9;
Step 3 was carried out in the same manner as the step 3 in Example 9;
Step 4 was carried out in the same manner as the step 4 in Example 9;
Step 5 was carried out in the same manner as the step 5 in Example 9;
Step 6 was carried out in the same manner as the step 6 in Example 19;
Step 7 was carried out in the same manner as the step 7 in Example 19;

Step 8: Preparation of Compound 20h

The compound 19 g (530 mg, 1.4 mmol) was dissolved in toluene (20 ml). Ethyl [(3-fluorophenyl)hydrazino]chloroacetate (557 mg, 2.2 mmol) and triethylamine (440 mg, 4.35 mmol) were added at room temperature to give a reaction mixture, which was refluxed overnight at 120° C. TLC was used to monitor the reaction progress. After the reaction was completed, toluene was removed by distillation under reduced pressure. The residue was dissolved by dichloromethane (20 ml). Trifluoroacetic acid (2 ml) was added at room temperature to obtain a reaction mixture, which was reacted overnight at room temperature. TLC was used to monitor the reaction progress. After the reaction was completed, the reaction mixture was purified by column chromatography to give compound 20h (525 mg, yellow solid), yield: 74.6%.

MS m/z (ES): 491.2 [M+1]

Step 9: Preparation of 1-(3-fluorophenyl)-7-oxo-6-[2-methyl-4-(2-oxo-piperidin-1-yl)phenyl]-4,5,6,7-tetrahydro-1H-pyrazolo[3,4-c]pyridine-3-carboxamide 20

The compound 20h (525 mg, 1.1 mmol) was dissolved in methanol (8 ml). Aqueous ammonia (6 ml) was added to give a reaction mixture, which was refluxed overnight at 70° C. TLC was used to monitor the reaction progress. After the reaction was completed, the reaction mixture was purified by column chromatography to give compound 20 (321 mg, light yellow solid), yield: 65.0%.

MS m/z (ES): 462.2 [M+1]

$^1$H NMR (400 MHz, CDCl$_3$) δ 7.44-7.36 (m, 3H), 7.22-7.10 (m, 4H), 6.85 (br s, 1H), 5.56 (br s, 1H), 4.12-4.05 (m, 1H), 3.89-3.83 (m, 1H), 3.60-3.58 (m, 2H), 3.48-3.30 (m, 2H), 2.57-2.54 (m, 2H), 2.25 (s, 3H), 1.94-1.92 (m, 4H).

Example 21: Preparation of 1-(4-methoxyphenyl)-7-oxo-6-[2-methoxy-4-(2-oxo-piperidin-1-yl)phenyl]-4,5,6,7-tetrahydro-1H-pyrazolo[3,4-c]pyridine-3-carboxamide

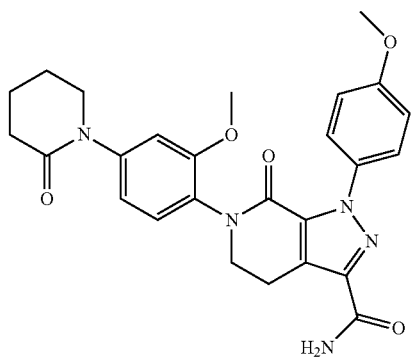 [SMILES: COc1ccc(-n2nc(C(N)=O)c3c2C(=O)N(c2ccc(N4CCCCC4=O)cc2OC)CC3)cc1]

Preparation scheme is shown below:

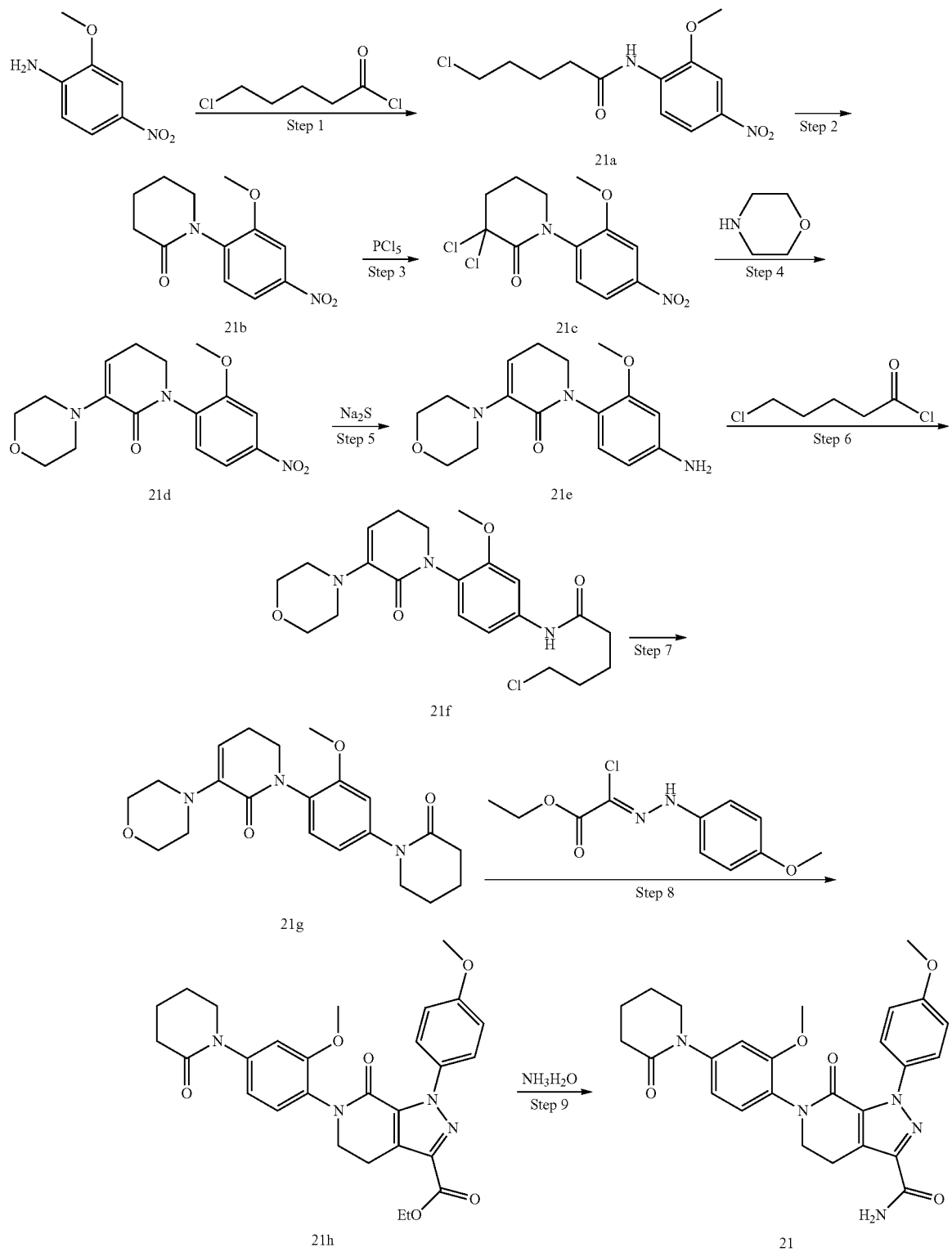

Step 1: Preparation of Compound 21a

The 2-methoxy-4-nitroaniline (5 g, 29.7 mmol) was dissolved in tetrahydrofuran (50 ml). N,N-diisopropylethylamine (9.6 g, 74.3 mmol) was added, cooled in ice bath to 5° C. or lower. 5-chlorovaleryl chloride (5.58 g, 36.0 mmol) was added dropwise to obtain a reaction mixture. The reaction mixture was reacted overnight at room temperature. TLC was used to monitor the reaction progress. After the reaction was completed, tetrahydrofuran was removed by distillation under reduced pressure, the residue was dissolved in ethyl acetate and washed with water for three times, dried over anhydrous magnesium sulfate, filtered, and the solvent was distilled off under reduced pressure to give compound 21a (7.6 g, yellow solid), yield: 89.4%.

MS m/z (ES): 287.1 [M+1]

Step 2: Preparation of Compound 21b

The compound 21a (7.6 g, 26.5 mmol) was dissolved in tetrahydrofuran (40 ml). Sodium hydride (1.42 g, 59.2 mmol) was added portion-wise under an ice bath to obtain a reaction mixture. Then the reaction mixture was reacted overnight at room temperature. TLC was used to monitor the reaction progress. After the reaction was completed, ice-water was added into the reaction solution under an ice bath to quench sodium hydride. After removing tetrahydrofuran by distillation under reduced pressure, the residue was extracted twice by ethyl acetate, dried over anhydrous magnesium sulfate, filtered, and the solvent was distilled off under reduced pressure. The residue was purified by column chromatography to give compound 21b (6.2 g, brown solid), yield: 93.4%.

MS m/z (ES): 251.1 [M+1]

Step 3: Preparation of Compound 21c

The compound 21b (6.2 g, 24.8 mmol) was dissolved in dichloromethane (180 ml). Phosphorus pentachloride (15.5 g, 74.4 mmol) was added portion-wise under an ice bath to obtain a reaction mixture. The reaction mixture was refluxed at 40° C. When the reaction solution generated little bubble, TLC was used to monitor the reaction progress. After the reaction was completed, ice-water was added into the reaction mixture under an ice bath to quench phosphorus pentachloride. The reaction solution was separated, washed with water for three times, dried over anhydrous magnesium sulfate, filtered, and the solvent was removed by distillation under reduced pressure to give compound 21c (7.5 g, yellow solid), yield: 94.9%.

MS m/z (ES): 319.0, 321.0 [M+1]

Step 4: Preparation of Compound 21d

The compound 21c (7.5 g, 23.5 mmol) was dissolved in morpholine (30 ml) to obtain a reaction mixture, which was refluxed at 120° C. for 2 hours, TLC was used to monitor the reaction progress. After the reaction was completed, most morpholine was removed by distillation under reduced pressure to give the residue as a yellow solid. Water was added to wash by stirring for 1 hour. The mixture was filtered, and the filter cake was washed by water for three times and then was air-dried for 24 hours to give compound 21d (7.2 g, yellow solid), yield: 92.3%.

MS m/z (ES): 334.1 [M+1]

Step 5: Preparation of Compound 21e

The compound 21d (7.2 g, 21.6 mmol) was dissolved in ethanol (90 ml). Sodium sulfide nonahydrate (10.4 g, 43.3 mmol) was added, and then water (30 ml) was added to obtain a reaction mixture, which was refluxed overnight at 50° C. TLC was used to monitor the reaction progress. After the reaction was completed, ethanol was removed by distillation under reduced pressure, the residue was extracted by ethyl acetate for three times, the combined organic phases were dried over anhydrous magnesium sulfate, filtered, and the solvent was removed by distillation under reduced pressure to give compound 21e (5.3 g, yellow solid) yield: 80.3%.

MS m/z (ES): 304.2 [M+1]

Step 6: Preparation of Compound 21f

The compound 21e (1 g, 3.3 mmol) was dissolved in tetrahydrofuran (50 ml). N,N-diisopropylethylamine (1.1 g, 8.5 mmol) was added, cooled in ice bath, 5-chlorovaleryl chloride (0.64 g, 4.1 mmol) was added dropwise to obtain a reaction mixture. The reaction mixture was reacted overnight at room temperature. TLC was used to monitor the reaction progress. After the reaction was completed, water was added into the reaction solution, which was separated and washed with water for three times, dried over anhydrous magnesium sulfate, filtered, and the solvent was distilled off under reduced pressure to give compound 21f (1.3 g, yellow solid), yield: 92.8%.

MS m/z (ES): 422.2 [M+1]

Step 7: Preparation of Compound 21 g

The compound 21f (1.3 g, 3.1 mmol) was dissolved in tetrahydrofuran (50 ml). Sodium hydride (0.2 g, 8.3 mmol) was added portion-wise under an ice bath to obtain a reaction mixture. Then the reaction mixture was reacted overnight at room temperature. TLC was used to monitor the reaction progress. After the reaction was completed, ice-water was added into the reaction solution to quench sodium hydride. After removing tetrahydrofuran by distillation under reduced pressure, the residue was extracted twice by dichloromethane, the combined organic phases were dried over anhydrous magnesium sulfate, filtered, and the solvent was distilled off under reduced pressure. The residue was purified by column chromatography to give compound 21 g (1.05 g, yellow solid), yield: 87.5%.

MS m/z (ES): 386.2 [M+1]

Step 8: Preparation of Compound 21h

The compound 21 g (309 mg, 0.8 mmol) was dissolved in ethyl acetate (10 ml). Ethyl [(4-methoxyphenyl)hydrazino]chloroacetate (247 mg, 0.96 mmol) and triethylamine (252 mg, 2.4 mmol) were added at room temperature to give a reaction mixture, which was refluxed overnight at 80° C. TLC was used to monitor the reaction progress. After the reaction was completed, 4N HCl (1.6 ml) was added slowly to give a reaction mixture, which was reacted overnight at room temperature. TLC was used to monitor the reaction progress. After the reaction was completed, the reaction mixture was purified by column chromatography to give compound 21h (311 mg, brown solid), yield: 74.8%.

MS m/z (ES): 519.2 [M+1]

Step 9: Preparation of 1-(4-methoxyphenyl)-7-oxo-6-[2-methoxy-4-(2-oxo-piperidin-1-yl)phenyl]-4,5,6,7-tetrahydro-1H-pyrazolo[3,4-c]pyridine-3-carboxamide The compound 21h (311 mg, 0.6 mmol) was dissolved in methanol (6 ml). Aqueous ammonia (4 ml) was added to give a reaction mixture, which was refluxed overnight at 55° C. TLC was used to monitor the reaction progress. After the reaction was completed, the reaction mixture was purified by column chromatography to give compound 21 (220 mg, white powder), yield: 75.0%.

MS m/z (ES): 490.2 [M+1]

$^1$H NMR (400 MHz, CDCl$_3$) δ 7.50 (d, J=8.9 Hz, 2H), 7.25 (d, J=8.3 Hz, 1H), 6.93 (d, J=9.0 Hz, 2H), 6.88-6.86 (m, 2H), 6.80 (dd, J=8.2, 1.9 Hz, 1H), 5.60 (br s, 1H), 3.99-3.81 (m, 8H), 3.60-3.58 (m, 2H), 3.37-3.35 (m, 2H), 2.57-2.54 (m, 2H), 1.94-1.92 (m, 4H).

Example 22: Preparation of 1-(3-fluorophenyl)-7-oxo-6-[2-methoxy-4-(2-oxo-piperidin-1-yl)phenyl]-4,5,6,7-tetrahydro-1H-pyrazolo[3,4-c]pyridine-3-carboxamide

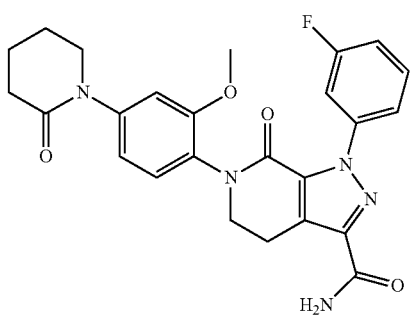 [SMILES: COc1cc(N2CCCCC2=O)ccc1N1CCc2c(C(N)=O)nn(-c3cccc(F)c3)c2C1=O]

Preparation scheme is shown below:

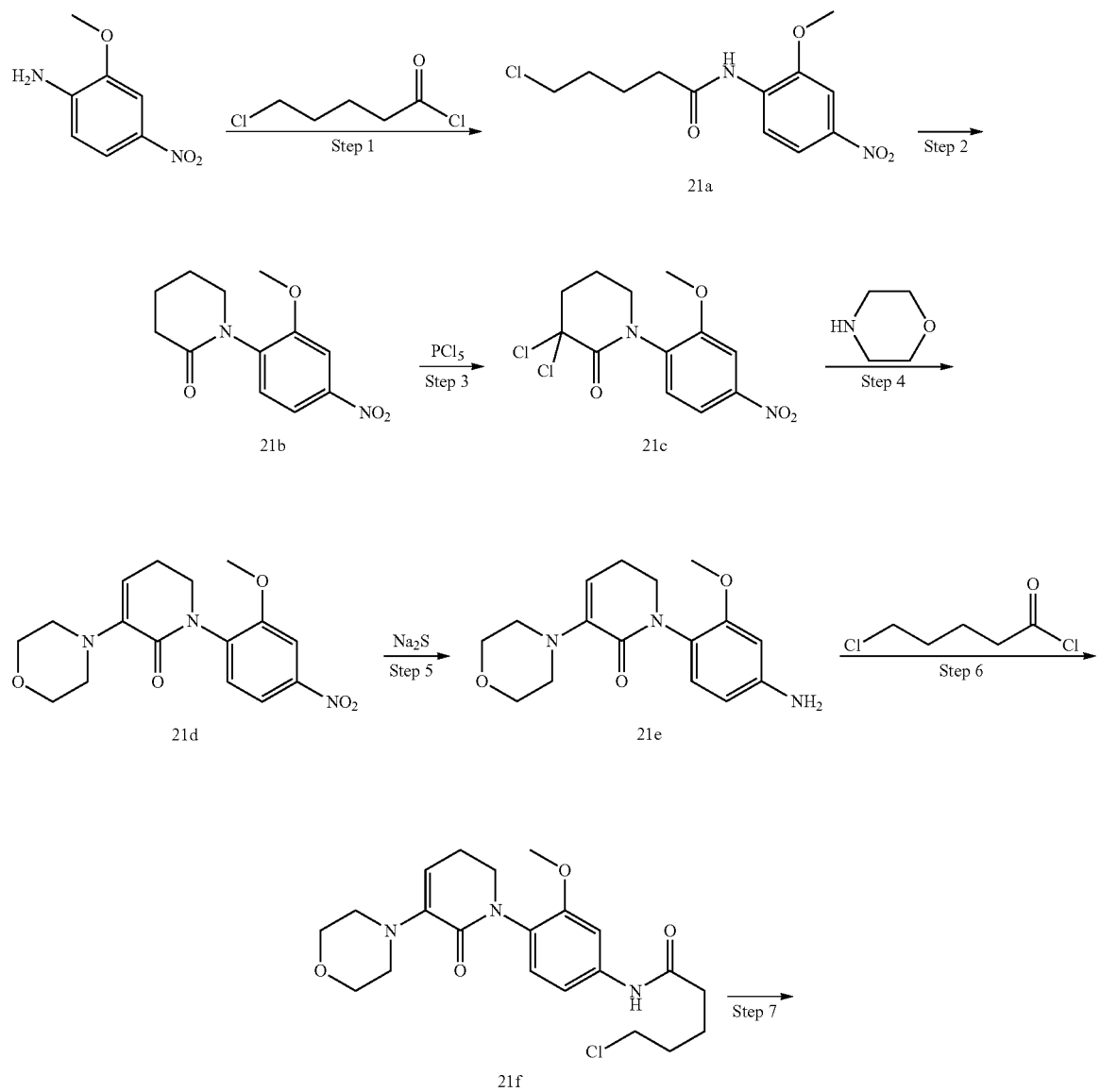

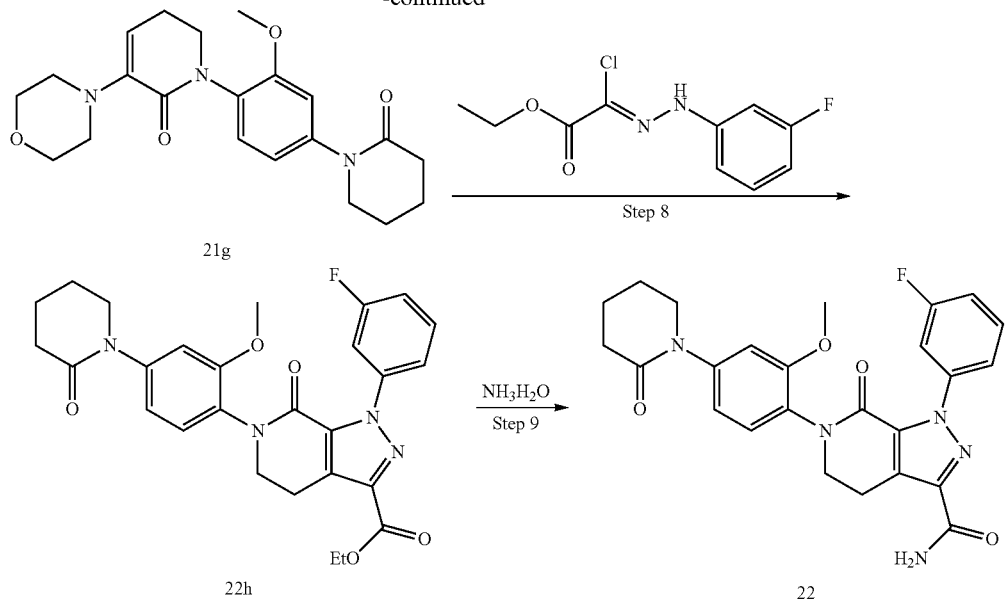

Step 1 was carried out in the same manner as the step 1 in Example 21;
Step 2 was carried out in the same manner as the step 2 in Example 21;
Step 3 was carried out in the same manner as the step 3 in Example 21;
Step 4 was carried out in the same manner as the step 4 in Example 21;
Step 5 was carried out in the same manner as the step 5 in Example 21;
Step 6 was carried out in the same manner as the step 6 in Example 21;
Step 7 was carried out in the same manner as the step 7 in Example 21;

Step 8: Preparation of Compound 22h

The compound 21 g (309 mg, 0.8 mmol) was dissolved in ethyl acetate (10 ml). Ethyl [(3-fluorophenyl)hydrazino]chloroacetate (235 mg, 0.96 mmol) and triethylamine (252 mg, 2.4 mmol) were added at room temperature to give a reaction mixture, which was refluxed overnight at 80° C. TLC was used to monitor the reaction progress. After the reaction was completed, 4N HCl (1.6 ml) was added slowly to give a reaction mixture, which was reacted overnight at room temperature. TLC was used to monitor the reaction progress. After the reaction was completed, the reaction mixture was purified by column chromatography to give compound 22h (320 mg, brown solid), yield: 78.8%.
MS m/z (ES): 507.2 [M+1]

Step 9: Preparation of 1-(3-fluorophenyl)-7-oxo-6-[2-methoxy-4-(2-oxo-piperidin-1-yl)phenyl]-4,5,6,7-tetrahydro-1H-pyrazolo[3,4-c]pyridine-3-carboxamide 22

The compound 22h (320 mg, 0.6 mmol) was dissolved in methanol (6 ml). Aqueous ammonia (4 ml) was added to give a reaction mixture, which was refluxed overnight at 55° C. TLC was used to monitor the reaction progress. After the reaction was completed, the reaction mixture was purified by column chromatography to give compound 22 (190 mg, yellow solid), yield: 63.0%.
MS m/z (ES): 478.2 [M+1]
$^1$H NMR (400 MHz, CDCl$_3$) δ 7.45-7.42 (m, 1H), 7.41-7.36 (m, 2H), 7.26 (d, J=8.1 Hz, 1H), 7.10 (tdd, J=8.2, 2.5, 1.2 Hz, 1H), 6.90 (d, J=2.1 Hz, 1H), 6.86 (br s, 1H), 6.82 (dd, J=8.3, 2.2 Hz, 1H), 5.63 (br s, 1H), 4.00-3.83 (m, 5H), 3.62-3.59 (m, 2H), 3.37-3.35 (m, 2H), 2.56 (t, J=5.6 Hz, 2H), 1.95-1.93 (m, 4H).

Experimental Example I: The Effects on APTT of Healthy Mice

1. The Purpose of the Experiment:
Test for four coagulation parameters (including prothrombin time (PT), activated partial thromboplastin time (APTT), thrombin time (TT) and fibrinogen (FIB)) belongs to one of clinical inspection items, and is necessary to thrombotic disease inspections or before the surgery. APTT mainly reflects whether the intrinsic coagulation system status is normal or not. Accordingly, the APTT value is used as a detection indicator in this test of the present invention. The anticoagulant effects of the compounds prepared in the Examples of the present invention were evaluated through the effects thereof on APTT of mice.
2. Experimental Materials:
  2.1 Tested Drugs:
  Positive drug: Apixaban, provided by Shanghai Haoyuan Chemical Technology Co., Ltd. white solid, Lot No.: HM-038_13-20130427; purity: 99.67%.
  Investigational drug: the compound of Example 2, provided by the Synthetic Laboratory of Chengdu Easton Pharmaceutical Co., Ltd., light yellow solid, Lot No.: 20130628; purity: 99.32%.
  Investigational drug: the compound of Example 3, provided by the Synthetic Laboratory of Chengdu Easton Pharmaceutical Co., Ltd., light yellow solid, Lot No.: 20130710; purity: 99.29%.
  Investigational drug: the compound of Example 4, provided by the Synthetic Laboratory of Chengdu Easton Pharmaceutical Co., Ltd., light yellow solid, Lot No.: 20130717; purity: 99.60%.

Investigational drug: the compound of Example 6, provided by the Synthetic Laboratory of Chengdu Easton Pharmaceutical Co., Ltd., light yellow solid, Lot No.: 20130717; purity: 97.56%.

Investigational drug: the compound of Example 8, provided by the Synthetic Laboratory of Chengdu Easton Pharmaceutical Co., Ltd., light yellow solid, Lot No.: 20130718; purity: 97.28%.

Investigational drug: the compound of Example 9, provided by the Synthetic Laboratory of Chengdu Easton Pharmaceutical Co., Ltd., light yellow solid, Lot No.: 20130719; purity: 99.22%.

Investigational drug: the compound of Example 10, provided by the Synthetic Laboratory of Chengdu Easton Pharmaceutical Co., Ltd., light yellow solid, Lot No.: 20130719; purity: 97.19%.

Investigational drug: the compound of Example 13, provided by the Synthetic Laboratory of Chengdu Easton Pharmaceutical Co., Ltd., light yellow solid, Lot No.: 20130722; purity: 98.27%.

Investigational drug: the compound of Example 15, provided by the Synthetic Laboratory of Chengdu Easton Pharmaceutical Co., Ltd., light yellow solid, Lot No.: 20130723; purity: 98.89%.

Investigational drug: the compound of Example 16, provided by the Synthetic Laboratory of Chengdu Easton Pharmaceutical Co., Ltd., light yellow solid, Lot No.: 20130723; purity: 99.45%.

Investigational drug: the compound of Example 17, provided by the Synthetic Laboratory of Chengdu Easton Pharmaceutical Co., Ltd., light yellow solid, Lot No.: 20130726; purity: 99.61%.

Investigational drug: the compound of Example 18, provided by the Synthetic Laboratory of Chengdu Easton Pharmaceutical Co., Ltd., light yellow solid, Lot No.: 20130801; purity: 98.62%.

Investigational drug: the compound of Example 19, provided by the Synthetic Laboratory of Chengdu Easton Pharmaceutical Co., Ltd., light yellow solid, Lot No.: 20130807; purity: 99.44%.

Investigational drug: the compound of Example 20, provided by the Synthetic Laboratory of Chengdu Easton Pharmaceutical Co., Ltd., light yellow solid, Lot No.: 20130805; purity: 97.78%.

Investigational drug: the compound of Example 21, provided by the Synthetic Laboratory of Chengdu Easton Pharmaceutical Co., Ltd., white solid, Lot No.: 20130809; purity: 99.77%.

2.2 Testing Equipment:

Sysmex CA7000 automatic coagulation analyzer, manufactured by Japan Sysmex Corporation;

Roche C501 automatic biochemical analyzer, manufactured by Roche;

ophthalmic tweezers, gavage needle, mortar, vacuum blood-collection tube, syringe, etc.

2.3 Testing Animals:

KM mice, weighing 28-30 g, male, 170 mice, provided by Chengdu Dashuo Biological Technology Co., Ltd.; Production facility license: SCXK (Chuan) 2008-24. Animals were housed in the animal room after purchased, adaptively observed for at least three days, and used for assays unless they were qualified for the quarantine standard.

3. Experimental Method:

(1) Grouping: mice were grouped and tested according to Table 1, wherein there were 10 mice in each group.

TABLE 1

| | assay grouping and dosing regimen | | | | |
|---|---|---|---|---|---|
| Groups | Investigational compounds | Administration route | Drug concentration (mg/ml) | Volume of administration (ml/10 g) | Dosage of administration (mg/kg) |
| Control group | normal saline | i.g | 0.25 | 0.2 | — |
| Positive group | Apixaban | i.g | 0.25 | 0.2 | 5 |
| Ex.2 group | Compound of Ex.2 | i.g | 0.25 | 0.2 | 5 |
| Ex.3 group | Compound of Ex.3 | i.g | 0.25 | 0.2 | 5 |
| Ex.4 group | Compound of Ex.4 | i.g | 0.25 | 0.2 | 5 |
| Ex.6 group | Compound of Ex.6 | i.g | 0.25 | 0.2 | 5 |
| Ex.8 group | Compound of Ex.8 | i.g | 0.25 | 0.2 | 5 |
| Ex.9 group | Compound of Ex.9 | i.g | 0.25 | 0.2 | 5 |
| Ex.10 group | Compound of Ex.10 | i.g | 0.25 | 0.2 | 5 |
| Ex.13 group | Compound of Ex.13 | i.g | 0.25 | 0.2 | 5 |
| Ex.15 group | Compound of Ex.15 | i.g | 0.25 | 0.2 | 5 |
| Ex.16 group | Compound of Ex.16 | i.g | 0.25 | 0.2 | 5 |
| Ex.17 group | Compound of Ex.17 | i.g | 0.25 | 0.2 | 5 |
| Ex.18 group | Compound of Ex.18 | i.g | 0.25 | 0.2 | 5 |
| Ex.19 group | Compound of Ex.19 | i.g | 0.25 | 0.2 | 5 |

TABLE 1-continued assay grouping and dosing regimen

| Groups | Investigational compounds | Administration route | Drug concentration (mg/ml) | Volume of administration (ml/10 g) | Dosage of administration (mg/kg) |
|---|---|---|---|---|---|
| Ex.20 group | Compound of Ex.20 | i.g | 0.25 | 0.2 | 5 |
| Ex.21 group | Compound of Ex.21 | i.g | 0.25 | 0.2 | 5 |

Measurement of APTT:

Mice in each group were administered with the corresponding investigational drugs (mice in control group were administered with the normal saline). At 1 hour after administration, blood was collected into 0.5 ml vacuum blood-collection tube containing sodium citrate from mice orbit. APTT values of animals were measured after collecting the blood samples.

4. Statistical Method:

Excel was used for statistics, experimental data were expressed as ($\bar{x}\pm SD$), and two-sided T-test method was used to statistically compare the experimental data among multiple groups.

5. Experimental Results

TABLE 2

Effect of compounds in the examples on APTT of mice ($\bar{x} \pm SD$)

| Groups | Number of animals | Dosage (mg/kg) | APTT (sec) |
|---|---|---|---|
| Control group | 10 | — | 17.66 ± 1.10 |
| Positive group | 10 | 5 | 21.46 ± 2.32 ** |
| Ex.2 group | 10 | 5 | 24.50 ± 2.50 ** $^\Delta$ |
| Ex.3 group | 10 | 5 | 27.81 ± 3.42 ** $^{\Delta\Delta}$ |
| Ex.4 group | 10 | 5 | 24.78 ± 2.64 ** $^\Delta$ |
| Ex.6 group | 10 | 5 | 27.32 ± 3.12 ** $^{\Delta\Delta}$ |
| Ex.8 group | 10 | 5 | 27.82 ± 2.71 ** $^{\Delta\Delta}$ |
| Ex.9 group | 10 | 5 | 31.29 ± 2.80 ** $^{\Delta\Delta}$ |
| Ex.10 group | 10 | 5 | 24.67 ± 2.37 ** $^\Delta$ |
| Ex.13 group | 10 | 5 | 24.78 ± 2.67 ** $^\Delta$ |
| Ex.15 group | 10 | 5 | 27.97 ± 2.32 ** $^{\Delta\Delta}$ |
| Ex.16 group | 10 | 5 | 29.89 ± 2.72 ** $^{\Delta\Delta}$ |
| Ex.17 group | 10 | 5 | 30.79 ± 2.91 ** $^{\Delta\Delta}$ |
| Ex.18 group | 10 | 5 | 28.96 ± 2.42 ** $^{\Delta\Delta}$ |
| Ex.19 group | 10 | 5 | 26.73 ± 3.12 ** $^{\Delta\Delta}$ |
| Ex.20 group | 10 | 5 | 24.71 ± 3.20 ** $^\Delta$ |
| Ex.21 group | 10 | 5 | 24.65 ± 2.18 ** $^\Delta$ |

Note:
compared with the control group, * $P < 0.05$, ** $P < 0.01$;
compared with positive group, $^\Delta P < 0.05$, $^{\Delta\Delta} P < 0.01$.

6. Conclusion

Table 2 indicated that compared with the control group, at 1 h after administration, APTT values of positive group and all of the investigational groups are significantly increased (**$P<0.01$), showing that Apixaban and the compounds of examples of the present invention can significantly increase the APTT value of mice at 1 h after administration;

Compared with the positive group Apixaban, at 1 h after administration, the APTT values of the compounds of Ex. 2, Ex. 4, Ex. 10, Ex. 13, Ex. 20 and Ex. 21 groups have significant difference ($^\Delta P<0.05$), showing that anticoagulant effect of the compound in each example is superior to positive drug Apixaban; wherein the anticoagulant effect of Ex. 3, Ex. 6, Ex. 8, Ex. 9, Ex. 15, Ex. 16, Ex. 17, Ex. 18, Ex. 19 groups are more outstanding ($^{\Delta\Delta}P<0.01$), and significantly better than positive drug Apixaban at the same dose.

Experimental Example 2: Pharmacokinetic Studies on Healthy Rats

The Purpose of the Experiment:

SD rats were used as test animals, and LC/MS/MS method was applied for measuring the drug concentrations of rats at different time after administrating the compounds of the present invention by gavage, respectively. Pharmacokinetic behaviors of the compounds of the present invention on rats were studied, so as to evaluate the pharmacokinetic characteristics thereof.

Experimental Materials:

2.1 Drugs:

Positive drug: Apixaban, provided by Shanghai Haoyuan Chemical Technology Co., Ltd. white solid, Lot No.: HM-038_13-20130427; purity: 99.67%.

Investigational drug: the compound of Example 6, provided by the Synthetic Laboratory of Chengdu Easton Pharmaceutical Co., Ltd., light yellow solid, Lot No.: 20130717; purity: 97.56%.

Investigational drug: the compound of Example 8, provided by the Synthetic Laboratory of Chengdu Easton Pharmaceutical Co., Ltd., light yellow solid, Lot No.: 20130718; purity: 97.28%.

Investigational drug: the compound of Example 9, provided by the Synthetic Laboratory of Chengdu Easton Pharmaceutical Co., Ltd., light yellow solid, Lot No.: 20130719; purity: 99.22%.

Investigational drug: the compound of Example 15, provided by the Synthetic Laboratory of Chengdu Easton Pharmaceutical Co., Ltd., light yellow solid, Lot No.: 20130723; purity: 98.89%.

Investigational drug: the compound of Example 16, provided by the Synthetic Laboratory of Chengdu Easton Pharmaceutical Co., Ltd., light yellow solid, Lot No.: 20130723; purity: 99.45%.

Investigational drug: the compound of Example 17, provided by the Synthetic Laboratory of Chengdu Easton Pharmaceutical Co., Ltd., light yellow solid, Lot No.: 20130726; purity: 99.61%.

Investigational drug: the compound of Example 18, provided by the Synthetic Laboratory of Chengdu Easton Pharmaceutical Co., Ltd., light yellow solid, Lot No.: 20130801; purity: 98.62%.

2.2 Testing equipment:

Agilent 1100-AB API4000 LC/MS/MS, manufactured by Agilent Technologies;

vacuum blood-collection tube, blood collection needle, filter paper, syringe, etc.

2.3 Testing Animals:

SD rats, weighing 180-220 g, male, 40 rats, 5 rats in each group, provided by Chengdu Dashuo Biological Technology Co., Ltd.; Production facility license: SCXK (Chuan) 2008-24. Animals were housed in the animal room after purchased, adaptively observed for at least three days, and used for assays unless they were qualified for the quarantine standard.

Experimental Method:

3.1 Grouping: the rats were randomly grouped according to Table 3, with no significant difference among the groups;

TABLE 3 assay grouping and dosing regimen

| Groups | Investigational compounds | Administration route | Drug concentration (mg/ml) | Volume of administration (ml/100 g) | Dosage of administration (mg/kg) |
|---|---|---|---|---|---|
| Positive group | Apixaban | i.g | 1 | 1 | 10 |
| Ex.6 group | Compound of Ex.6 | i.g | 1 | 1 | 10 |
| Ex.8 group | Compound of Ex.8 | i.g | 1 | 1 | 10 |
| Ex.9 group | Compound of Ex.9 | i.g | 1 | 1 | 10 |
| Ex.15 group | Compound of Ex.15 | i.g | 1 | 1 | 10 |
| Ex.16 group | Compound of Ex.16 | i.g | 1 | 1 | 10 |
| Ex.17 group | Compound of Ex.17 | i.g | 1 | 1 | 10 |
| Ex.18 group | Compound of Ex.18 | i.g | 1 | 1 | 10 |

3.2 Collection and measurement of blood samples:

Rats in each group was administrated by gavage with the corresponding investigational drugs according to Table 3, at 5 min, 10 min, 20 min, 30 min, 1 h, 2 h, 4 h, 6 h, 8 h, 10 h, 12 h, 24 h after administration, 0.5 ml of blood was taken into the vacuum blood-collection tubes containing heparin sodium, and centrifuged at 5,000 rpm to obtain plasma which was stored at −20° C.

3.3 Analysis Method:

50 μL plasma at each time after administration was taken, then 150 μL of acetonitrile was added, which was subjected to vortex at 1500 rpm for 2 minutes. Solution was centrifuged for 15 minutes (3500 r/min), after that 10 μL supernatant was analyzed by HPLC/MS/MS.

4. Calculation of the Pharmacokinetic Parameters:

The pharmacokinetic behaviors of the investigational compounds were subjected to compartmental model fitting, and DAS 2.0 software was used to calculate the main pharmacokinetic parameters.

5. Experimental Results

TABLE 4 pharmacokinetic parameters of compounds in the examples

| Groups | Cmax (μg/ml) | Tmax (h) | $T_{1/2}$ (h) | $AUC_{0-24}$ (μg/ml · h) |
|---|---|---|---|---|
| Positive group | 6850 | 0.50 | 5.20 | 12871 |
| Ex.6 group | 7560 | 0.30 | 5.80 | 19760 |
| Ex.8 group | 7860 | 0.30 | 6.20 | 20140 |
| Ex.9 group | 9360 | 0.20 | 6.40 | 36447 |
| Ex.15 group | 8750 | 0.25 | 6.50 | 32430 |
| Ex.16 group | 9450 | 0.25 | 6.20 | 37653 |
| Ex.17 group | 9670 | 0.25 | 6.80 | 38560 |
| Ex.18 group | 8970 | 0.25 | 6.80 | 35480 |

As can be seen from the test results in Table 4, compared with positive group, the compounds in Example 6 group, Example 8 group, Example 9 group, Example 15 group, Example 16 group, Example 17 group and Example 18 group are significantly better than Apixaban in $C_{max}$ (maximum concentration), $T_{max}$ (time of maximum concentration), $T_{1/2}$ (elimination half-life) and AUC (area under the curve), showing that compared with Apixaban, the pharmacokinetics and bioavailabilities of compounds prepared in Examples 6, 8, 9, 15, 16, 17 and 18 are significantly improved.

Experimental Example 3: Human FXa Inhibitor Effects of the Compounds of the Present Invention The Purpose of the Experiment:

Inhibitory effects of the compounds of the present invention on human FXa were studied, to measure $IC_{50}$ values thereof on human FXa.

Experimental Materials:

2.1 Drugs:

Positive drug: Apixaban, provided by Shanghai Haoyuan Chemical Technology Co., Ltd. white solid, Lot No.: HM-038_13-20130427; purity: 99.67%.

Investigational drug: the compound of Example 9, provided by the Synthetic Laboratory of Chengdu Easton Pharmaceutical Co., Ltd., light yellow solid, Lot No.: 20130719; purity: 99.22%.

Investigational drug: the compound of Example 15, provided by the Synthetic Laboratory of Chengdu Easton Pharmaceutical Co., Ltd., light yellow solid, Lot No.: 20130723; purity: 98.89%.

Investigational drug: the compound of Example 16, provided by the Synthetic Laboratory of Chengdu Easton Pharmaceutical Co., Ltd., light yellow solid, Lot No.: 20130723; purity: 99.45%.

Investigational drug: the compound of Example 17, provided by the Synthetic Laboratory of Chengdu Easton Pharmaceutical Co., Ltd., light yellow solid, Lot No.: 20130726; purity: 99.61%.

Investigational drug: the compound of Example 18, provided by the Synthetic Laboratory of Chengdu Easton Pharmaceutical Co., Ltd., light yellow solid, Lot No.: 20130801; purity: 98.62%.

2.2 Testing Equipment:

EnVision Multiple-tag detector (Perkin Elmer Corporation);

human FXa enzyme (Sekisui Diagnostics, REF 526);

Fluorogenic substrate for the FXa assay (American diagnostic, Product No. 222F);

384-well assay plate (Corning, Cat. 3573);

Buffer: 20 mM Tris-HCl, 200 mM NaCl, 2.5 mM $CaCl_2$, pH 8.0.

2.3 Experimental Method:

(1) Prior to use, the compounds in Examples and Apixaban were dissolved in DMSO to 10 mM, respectively;

(2) 10 mM of each compound was 5-fold diluted serially with buffer to different concentrations (from 40 μM to 0.00002048 μM);

(3) 6 μL of the above diluted solutions of Step (2) were added into each well of 384-well plate to make a final volume of 60 μL, and the final concentration of the compound ranged from 4 μM to 0.000002048 nM;

(4) 30 μL of human FXa enzyme (2 nM) was added into each well, with a final concentration of 1 nM;

(5) 24 μL human FXa fluorescent enzyme substrate (266.7 μM) was added into each well, with a final concentration of 106.7 μM;

(6) the plate was gently shaked for 5 minutes and then incubated for 30 minutes at room temperature, with avoidance from light;

(7) fluorescence signal was read at 360/440 nm, the inhibition percentage was measured, and 4 Parameter Logistic Model in Xlfit software was employed to calculate $IC_{50}$.

Experimental Results

TABLE 5

Human FXa inhibitory effects of compounds in the examples

| Example | Compounds | $IC_{50}$ (nM) |
| --- | --- | --- |
| Example 9 | Compound of Ex.9 | 0.078 |
| Example 15 | Compound of Ex.15 | 0.124 |
| Example 16 | Compound of Ex.16 | 0.023 |
| Example 17 | Compound of Ex.17 | 0.015 |
| Example 18 | Compound of Ex.18 | 0.091 |
| Positive control | Apixaban | 0.925 |

It can be seen from Table 5 of human FXa inhibitory effect of the compounds in the examples that: compared with positive drug Apixaban, the compounds of the present invention have significant FXa inhibitory activities.

The above test results show that the compounds in the examples of the present invention exhibit significant FXa inhibitory activity, coagulating activity and excellent pharmacokinetic properties, which can be used for preparing Factor Xa inhibitors, further may be used for preparing anticoagulants, and still further may be used for preparing a medicament for preventing or treating thrombosis or embolism.

The above results show that the compounds in the examples of the present invention exhibit excellent anticoagulant effects and pharmacokinetic behaviors. It is apparent for the ordinary skilled persons in the art that, without departing from the spirit or scope of the present invention, various modifications and variations can be made to the compounds, compositions and the methods of the present invention, therefore, the scope of the present invention encompasses various modifications and variations made thereto, as long as the modifications and variations fall within the scope encompassed by the claims and equivalent embodiments thereof.

What is claimed is:

1. A compound as shown in general formula I:

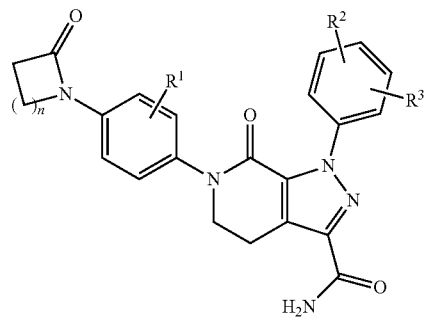

wherein $R^1$ is selected from hydrogen atom or methyl;

$R^2$ is selected from methyl, methoxy or fluorine atom;

$R^3$ is selected from hydrogen atom, methyl, methoxy or fluorine atom;

n=2.

2. The compound according to claim 1, characterized in that, $R^1$ is selected from methyl;

$R^2$ is selected from methyl, methoxy or fluorine atom;

$R^3$ is selected from hydrogen atom, methyl, methoxy or fluorine atom;

n=2.

3. The compound according to claim 1, characterized in that said compound is selected from:

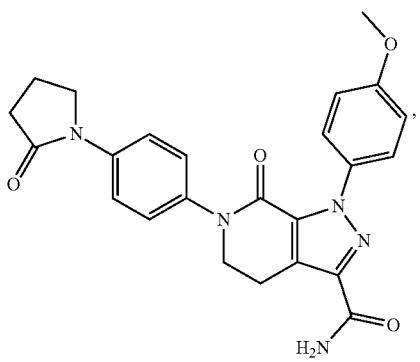

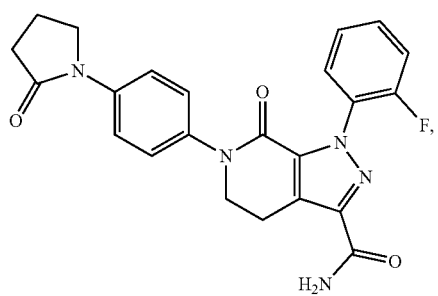

123
-continued
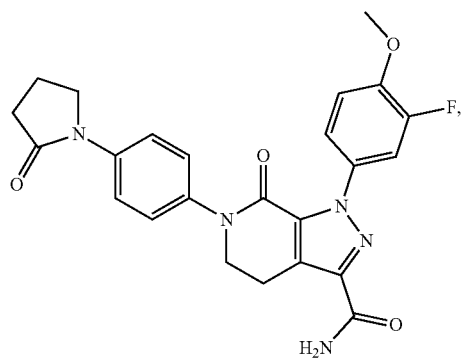
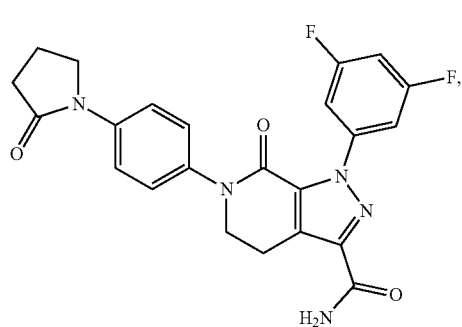
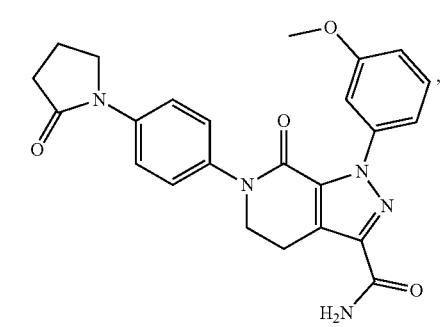
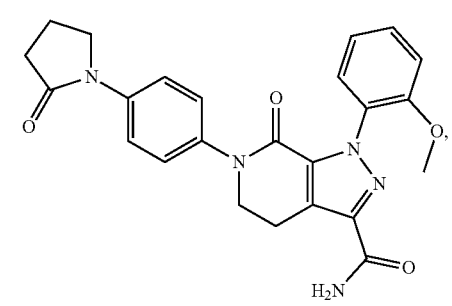
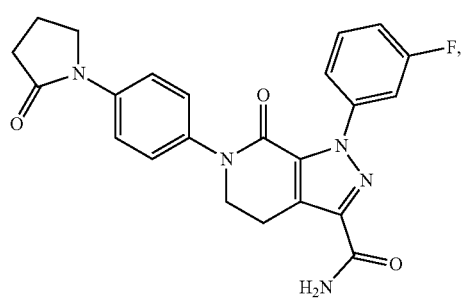
124
-continued
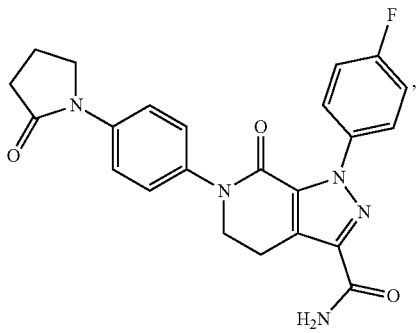
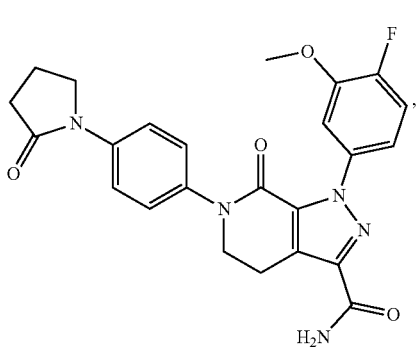
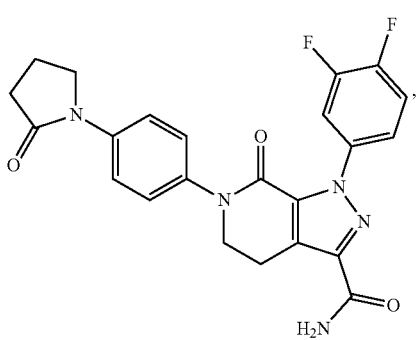
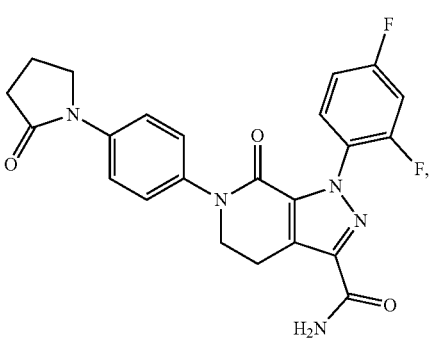
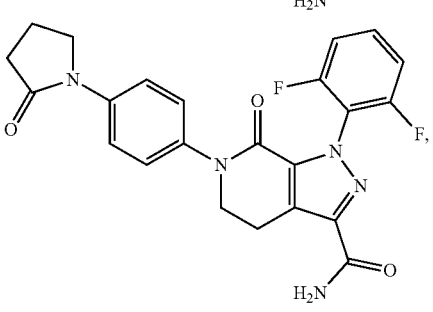

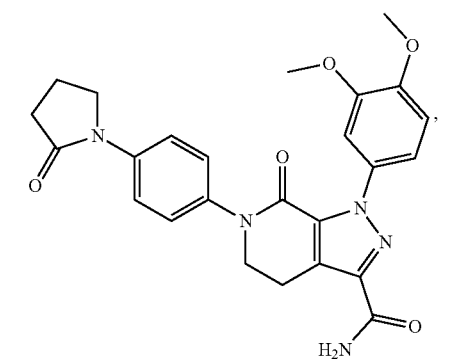
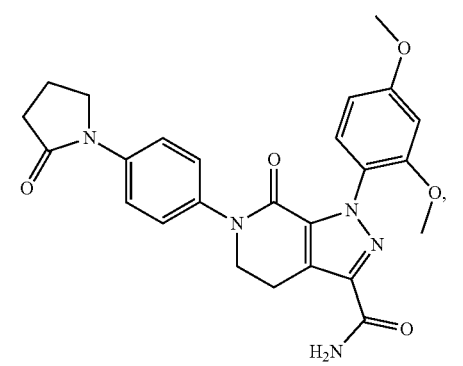
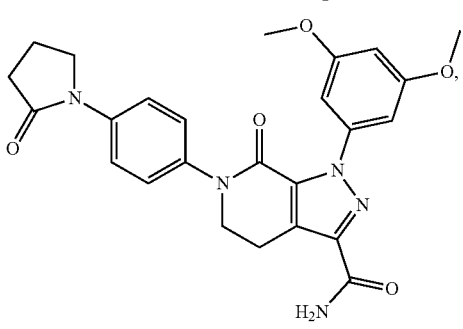
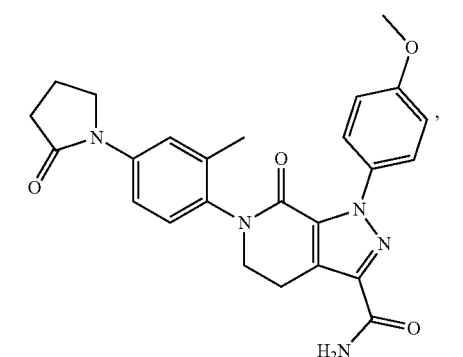
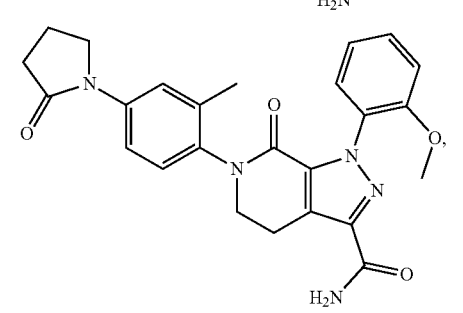
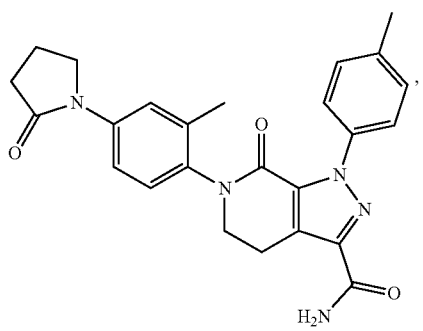
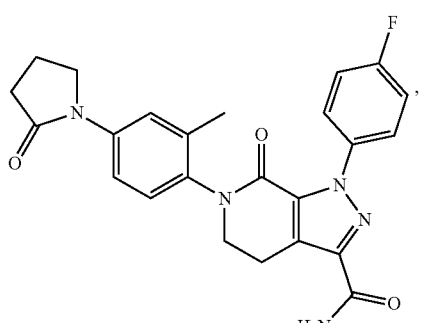
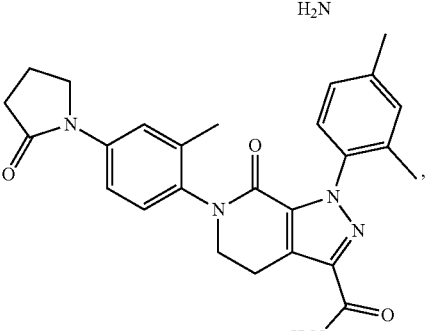
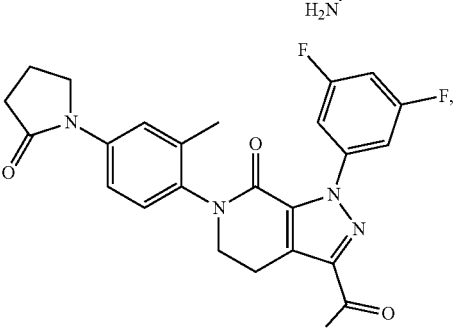
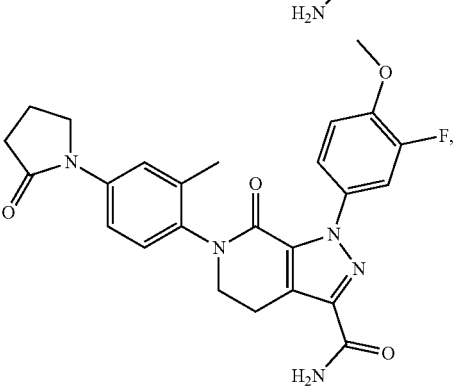

127
-continued
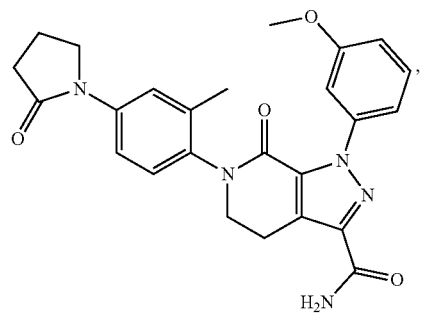
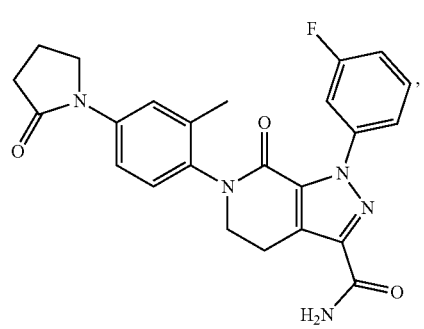
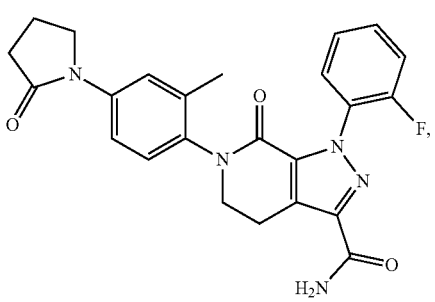
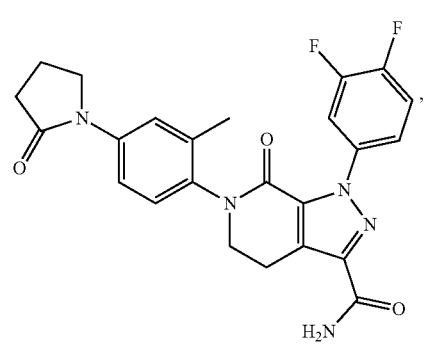
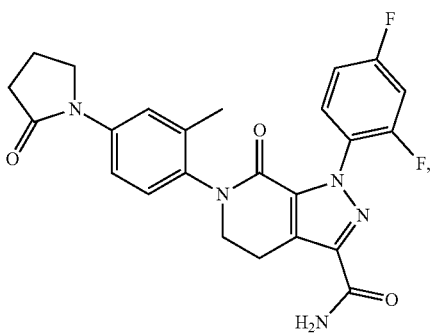
128
-continued
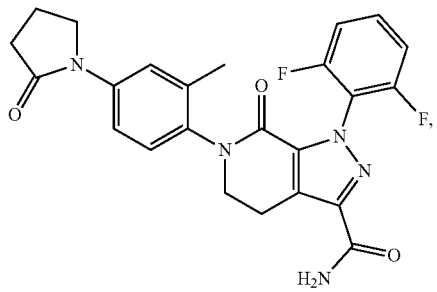
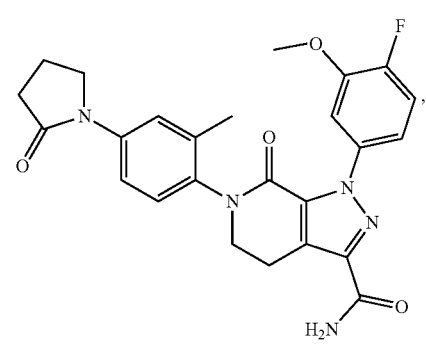
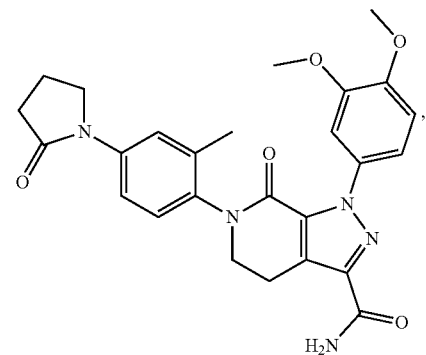
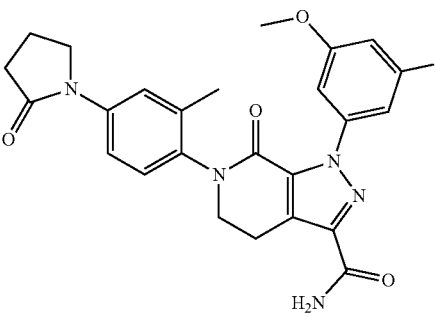
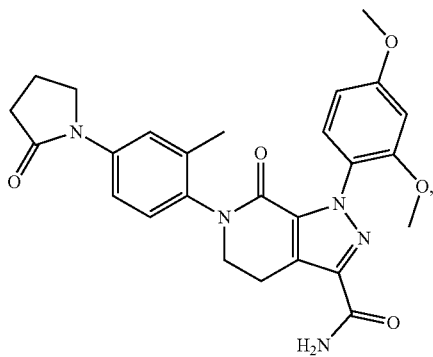

129
-continued
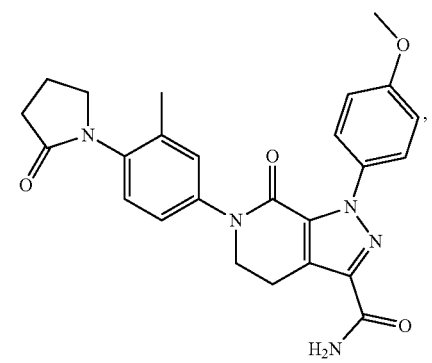
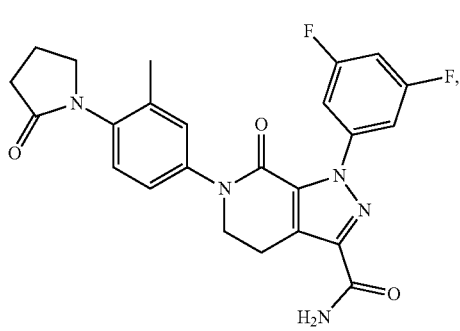
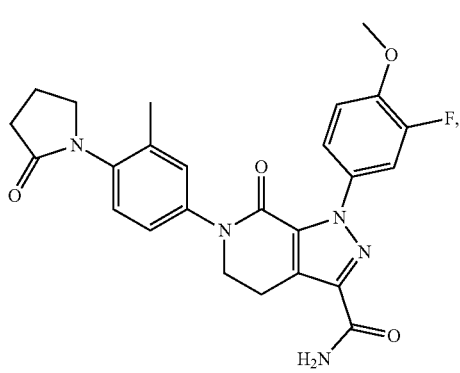
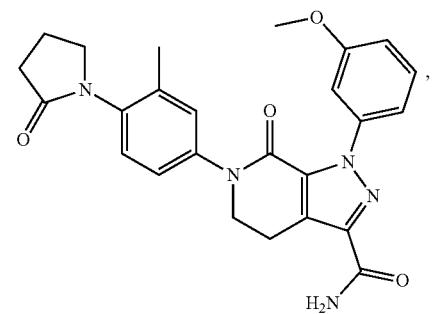
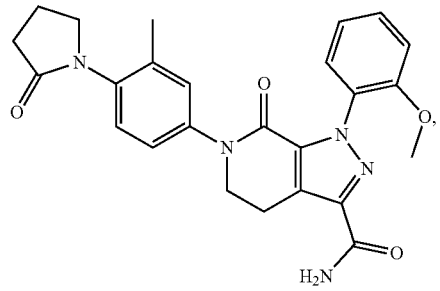
130
-continued
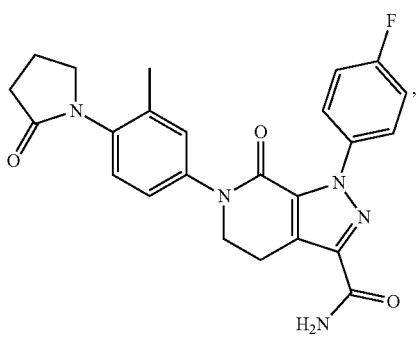
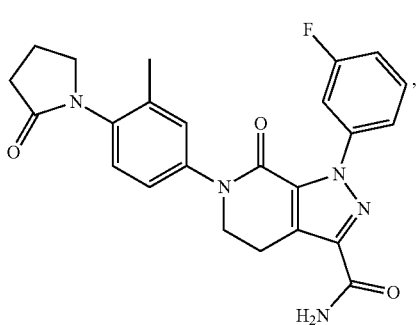
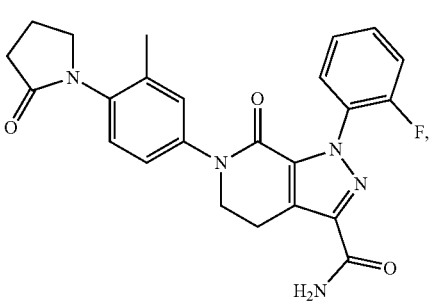
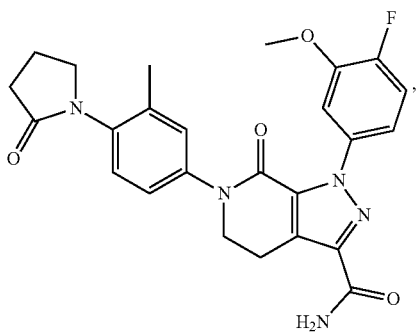
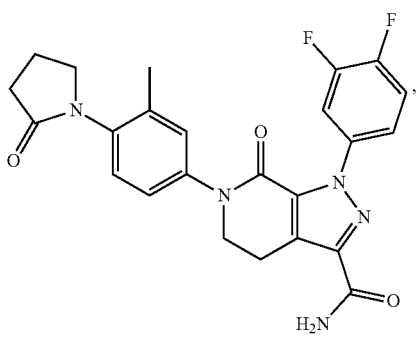

-continued

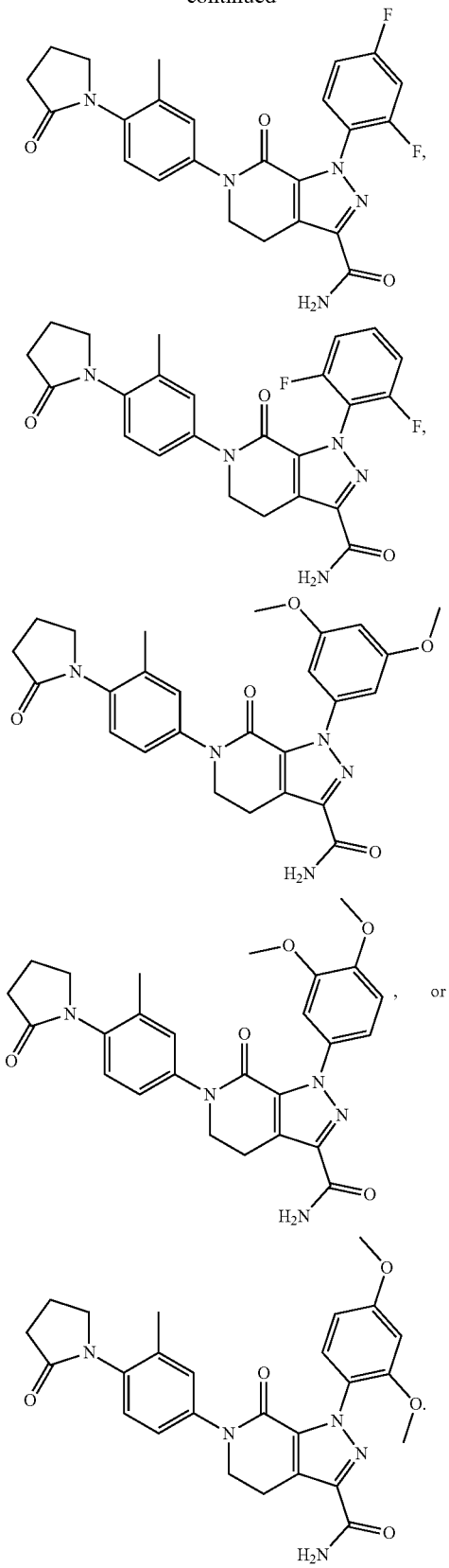

4. The compound according to claim 3, characterized in that said compound is:

1-(4-methoxyphenyl)-7-oxo-6-[4-(2-oxo-pyrrolidin-1-yl)phenyl]-4,5,6,7-tetrahydro-1H-pyrazolo[3,4-c]pyridine-3-carboxamide;
1-(2-fluorophenyl)-7-oxo-6-[4-(2-oxo-pyrrolidin-1-yl)phenyl]-4,5,6,7-tetrahydro-1H-pyrazolo[3,4-c]pyridine-3-carboxamide;
1-(3-fluoro-4-methoxyphenyl)-7-oxo-6-[4-(2-oxo-pyrrolidin-1-yl)phenyl]-4,5,6,7-tetrahydro-1H-pyrazolo[3,4-c]pyridine-3-carboxamide;
1-(3,5-difluoro-phenyl)-7-oxo-6-[4-(2-oxo-pyrrolidin-1-yl)phenyl]-4,5,6,7-tetrahydro-1H-pyrazolo[3,4-c]pyridine-3-carboxamide;
1-(4-methoxyphenyl)-7-oxo-6-[2-methyl-4-(2-oxo-pyrrolidin-1-yl)phenyl]-4,5,6,7-tetrahydro-1H-pyrazolo[3,4-c]pyridine-3-carboxamide;
1-(2-methoxyphenyl)-7-oxo-6-[2-methyl-4-(2-oxo-pyrrolidin-1-yl)phenyl]-4,5,6,7-tetrahydro-1H-pyrazolo[3,4-c]pyridine-3-carboxamide;
1-(4-methylphenyl)-7-oxo-6-[2-methyl-4-(2-oxo-pyrrolidin-1-yl)phenyl]-4,5,6,7-tetrahydro-1H-pyrazolo[3,4-c]pyridine-3-carboxamide;
1-(4-fluorophenyl)-7-oxo-6-[2-methyl-4-(2-oxo-pyrrolidin-1-yl)phenyl]-4,5,6,7-tetrahydro-1H-pyrazolo[3,4-c]pyridine-3-carboxamide;
1-(2,4-dimethyl-phenyl)-7-oxo-6-[2-methyl-4-(2-oxo-pyrrolidin-1-yl)phenyl]-4,5,6,7-tetrahydro-1H-pyrazolo[3,4-c]pyridine-3-carboxamide;
1-(3,5-difluoro-phenyl)-7-oxo-6-[2-methyl-4-(2-oxo-pyrrolidin-1-yl)phenyl]-4,5,6,7-tetrahydro-1H-pyrazolo[3,4-c]pyridine-3-carboxamide;
1-(3-fluoro-4-methoxyphenyl)-7-oxo-6-[2-methyl-4-(2-oxo-pyrrolidin-1-yl)phenyl]-4,5,6,7-tetrahydro-1H-pyrazolo[3,4-c]pyridine-3-carboxamide;
1-(4-methoxyphenyl)-7-oxo-6-[3-methyl-4-(2-oxo-pyrrolidin-1-yl)phenyl]-4,5,6,7-tetrahydro-1H-pyrazolo[3,4-c]pyridine-3-carboxamide;
1-(3,5-difluorophenyl)-7-oxo-6-[3-methyl-4-(2-oxo-pyrrolidin-1-yl)phenyl]-4,5,6,7-tetrahydro-1H-pyrazolo[3,4-c]pyridine-3-carboxamide; or
1-(3-fluoro-4-methoxyphenyl)-7-oxo-6-[3-methyl-4-(2-oxo-pyrrolidin-1-yl)phenyl]-4,5,6,7-tetrahydro-1H-pyrazolo[3,4-c]pyridine-3-carboxamide.

5. A compound as shown in general formula I:

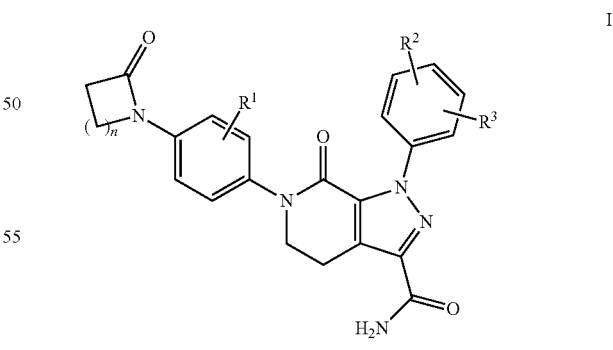

I wherein $R^1$ is methyl;
$R^2$ is selected from methoxy or fluorine atom;
$R^3$ is selected from hydrogen atom, methoxy or fluorine atom;
n=2.

6. The compound according to claim 5, characterized in that said compound is selected from:

1-(4-methoxyphenyl)-7-oxo-6-[2-methyl-4-(2-oxo-pyrrolidin-1-yl)phenyl]-4,5,6,7-tetrahydro-1H-pyrazolo[3,4-c]pyridine-3-carboxamide;

1-(3-fluoro-4-methoxyphenyl)-7-oxo-6-[2-methyl-4-(2-oxo-pyrrolidin-1-yl)phenyl]-4,5,6,7-tetrahydro-1H-pyrazolo[3,4-c]pyridine-3-carboxamide;

1-(4-methoxyphenyl)-7-oxo-6-[3-methyl-4-(2-oxo-pyrrolidin-1-yl)phenyl]-4,5,6,7-tetrahydro-1H-pyrazolo[3,4-c]pyridine-3-carboxamide;

1-(3,5-difluorophenyl)-7-oxo-6-[3-methyl-4-(2-oxo-pyrrolidin-1-yl)phenyl]-4,5,6,7-tetrahydro-1H-pyrazolo[3,4-c]pyridine-3-carboxamide; or 1-(3-fluoro-4-methoxyphenyl)-7-oxo-6-[3-methyl-4-(2-oxo-pyrrolidin-1-yl)phenyl]-4,5,6,7-tetrahydro-1H-pyrazolo[3,4-c]pyridine-3-carboxamide.

7. A method for treating or preventing Factor Xa related disease, which comprises administrating the compound according to claim 1 as a Factor Xa inhibitor to a subject in need thereof.

8. The method according to claim 7, characterized in that the Factor Xa inhibitors are anticoagulants.

9. The method according to claim 8, characterized in that the Factor Xa related disease is thrombosis or embolism.

* * * * *